(12) United States Patent
Hockensmith et al.

(10) Patent No.: US 6,573,060 B1
(45) Date of Patent: Jun. 3, 2003

(54) METHODS AND COMPOSITIONS FOR TARGETING DNA METABOLIC PROCESSES USING AMINOGLYCOSIDE DERIVATIVES

(75) Inventors: Joel W. Hockensmith, Charlottesville, VA (US); Rohini Muthuswami, Denver, CO (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/722,708

(22) Filed: Nov. 28, 2000

Related U.S. Application Data

(60) Division of application No. 09/179,558, filed on Oct. 27, 1998, now Pat. No. 6,180,612, which is a continuation-in-part of application No. 09/060,470, filed on Apr. 15, 1998, now abandoned.
(60) Provisional application No. 60/063,898, filed on Oct. 31, 1997.

(51) Int. Cl.$^7$ .............................. C12Q 1/48; C12Q 1/34; C07H 15/22; C07H 15/232; C07H 15/234
(52) U.S. Cl. ........................... 435/15; 435/18; 536/4.1; 536/13.2; 536/13.3; 536/13.6; 536/13.7
(58) Field of Search ............................... 435/4, 18, 15; 536/13.2, 13.3, 13.6, 4.1, 13.7

(56) References Cited

FOREIGN PATENT DOCUMENTS

WO    WO 94/06439    3/1994

OTHER PUBLICATIONS

Abdel–Monem, M. and Hoffman–Berling,H. (1976). Enzymic Unwinding of DNA, *Eur. J. Biochem.*, 65: 431–440.
Arai,K., Yasuda S.., and Kornberg,A. (1981). Mechanism of dnaB Protein Action, *J. Biol. Chem.*, 256: 5247–5252.
Assairi, L.M. and Johnston,I.R. (1979). A DNA–Dependent ATPase of Calf–Thymus, *Eur. J. Biochem.*, 99: 71–79.
Auble,D.T., Hansen,K.E., Mueller,C.G., Lane,W.S., Thorner,J., and Hahn,S. (1994). Mot1, a global repressor of RNA polymerase II transcription, inhibits TBP binding to DNA by an ATP–dependent mechanism, *Genes & Dev.*, 8: 1920–1934.
Ausubel F.M. et al., eds., (1989), *Current Protocols in Molecular Biology*, Greene Publishing Associates, Inc., and John Wiley & sons, Inc., New York, at vol. I,. 2,.10,.3.
Bean,D.W., Kallam,W.E., Jr., and Matson,S.W. (1993). Purification and characterization of a DNA helicase from *Saccharomyces cerevisia, J. Biol. Chem.* 268: 21783–21790.
Beaucaire (1995, abstract) Journal of Chemotherapy. vol. 7, Suppl 2, pp. 111–123.
Biamonti,G., Cobianchi,F., Falaschi,A., and Riva,S. (1983). Total Purification of a DNA–dependent ATPase and of a DNA–Binding Protein from Human Cells, *EMBO J.*, 2: 161–165.

Biswas et al., (1986), The dnaB Protein of *Escherichia coli*: Mechanism of Nucleotide Binding, Hydrolysis and Modulation by dnaC Protein, *Biochemistry*, 25–23:7368–7374, Fig.3.
Bork,P. and Koonin,E.V. (1993). An Expanding Family of Helicases Within the 'DEAD/H' Superfamily, *Nucleic Acids Res.*, 21: 751–752.
Boxer,L.M. and Korn,D. (1980). Structural and Enzymological Characterization of a Deoxyribonucleic Acid Dependent Adenosine Triphosphatase from KB Cell Nuclei, *Biochemistry*, 19: 2623–2633.
Brewer,B.J., Martin,S.R., and Champoux,J.J. (1983). A Cellular Single–Stranded DNA–dependent ATPase Associated with Simian Virus 40 Chromatin, *J. Biol. Chem.*, 258: 4496–4502.
Bryan et al., (1975), The relationship of Aminoglycoside permeability to Streptomycin and Gentamycin susceptibility of Pseudomonas Aeruginosa, Mitsuhashi, S. and Hashimoto, J. Eds., Microbial Drug Resistance, Baltimore University Park Press pp 475–490.
Bunz,F., Kobayashi,R., and Stillman,B. (1993). cDNAs Encoding the Large Subunit of Human Replication Factor C, *Proc. Natl. Acad. Sci. U.S.A.*, 90: 11014–11018.
Cairns,B.R., Kim,Y.J., Sayre,M.H., Laurent,B.C., and Kornberg,R.D. (1994). A multisubunit complex containing the SWI1/ADR6, SWI2/SNF2, SWI3, SNF5, and SNF6 gene products isolated from yeast, *Proc. Natl. Acad. Sci. U.S.A.*, 91: 1950–1954.
Cao,Q.P., Pitt,S., Leszyk,J., and Baril,E.F. (1994). DNA–dependent ATPase form HeLa cells is related to human Ku autoantigen, *Biochemistry*, 33: 8548–8557.
Capson,T.L., Benkovic,S.J., and Nossal,N.G. (1991). Protein–DNA Cross–Linking Demonstrates Stepwise ATP–dependent Assembly of T4 DNA Polymerase and Its Accessory Proteins on the Primer–Template, *Cell* 65: 249–258.
Carlson,M. and Laurent,B.C. (1994). The SNF/SWI family of global transcriptional activators. [Review]. Curr. Opin, *Cell Biol.*, 6: 396–402.
Chan,D.W. and Lees–Miller,S.P. (1996). The DNA–dependent protein kinase is inactivated by autophosphorylation of the catalytic subunit, *J. Biol. Chem.*, 271: 8936–8941.

(List continued on next page.)

Primary Examiner—Elizabeth Slobodyansky
(74) Attorney, Agent, or Firm—John P. Breen

(57) ABSTRACT

Protein targets for disease intervention through inhibition of nucleic acid metabolism are disclosed. Novel polypeptides for one such target, DNA-dependent ATPase A, and novel polynucleotides encoding DNA-dependent ATPase A are disclosed. Phosphoaminoglycoside compounds which act on such protein targets to inhibit nucleic acid metabolism. In addition, screening assays for identifying compounds that inhibit nucleic acid-dependent ATPase activity, including, but not limited to, DNA-dependent ATPase A, are disclosed. Such compounds are useful in the treatment of diseases, including but not limited to cancer and infectious disease, through disruption of nucleic acid metabolism and induction of apoptosis. Moreover, methods for prevention and treatment of diseases including, but not limited to cancer and infectious disease are disclosed.

12 Claims, 23 Drawing Sheets

OTHER PUBLICATIONS

Figure 5A:
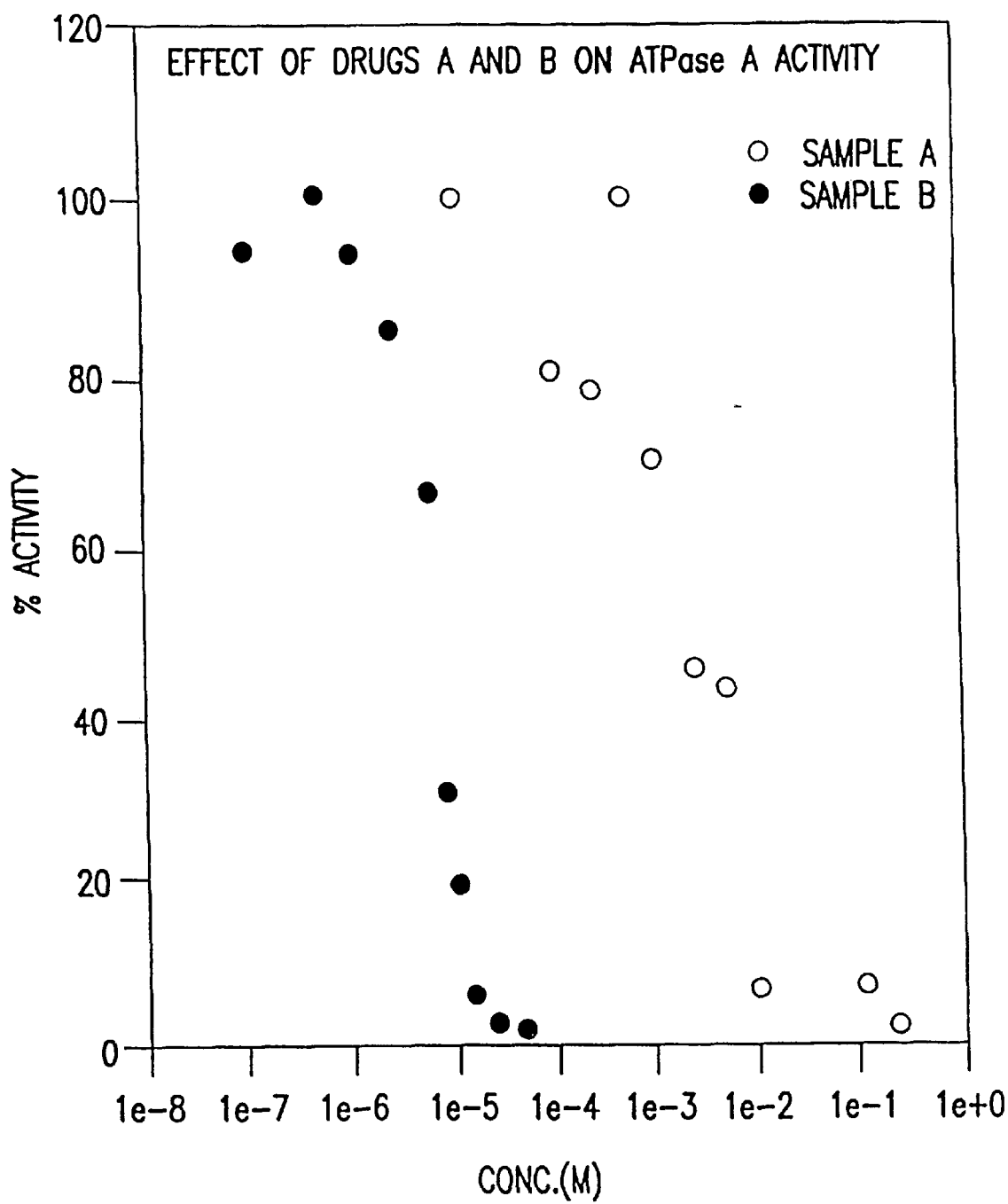

Côté,J., Quinn,J., Workman,J.L., and Peterson,C.L. (1994). Stimulation of GAL4 derivative binding to nucleosomal DNA by the yeast SWI/SNF complex, *Science*, 265: 53–60.

Creighton, (1983), "Proteins: Structures and Molecular Principles", W.H. Freeman & Co., N.Y., pp. 34–49, 50–60.

De Jong,P.J., Tommassen,J.P.M., van der Vliet,P.C., and Jansz,H.S. (1981). Purification and Characterization of DNA–dependent ATP Phosphohydrolases from KB Cells, *Eur. J. Biochem.*, 117: 179–186.

Drapkin,R., Sancar,A., and Reinberg,D. (1994). Where transcription meets repair. [Review], *Cell*, 77: 9–12.

Ebisuzaki et al., (1981), Postinfection Control in T4 Bacteriophage infection: Inhibition of the Rep. Function, *J. Virol.*, 37–3:893–898.

Eisen,J.A., Sweder,K.S., and Hanawalt,P.C. (1995). Evolution of the SNF2 family of proteins: subfamilies with distinct sequences and functions. [Review], *Nucleic Acids Res.*, 23: 2715–2723.

Falzon,M., Fewell,J.W., and Kuff,E.L. (1993). EBP–80, a transcription factor closely resembling the human autoantigen Ku, recognizes single– to double–strand transitions in DNA., *J. Biol. Chem.*, 268: 10546–10552.

Finer et al. (1992, abstract) Journal of the Royal Society of Medicine, vol. 85(9), pp. 530–533.

Froelich–Ammon,S.J., Gale,K.C., and Osheroff,N. (1994). Site–specific cleavage of a DNA hairpin by topoisomerase II. DNA secondary structure as a determinant of enzyme recognition/cleavage, *J. Biol. Chem.*, 269: 7719–7725.

Gates, C.A. and Northrop,D.B. (1988). Substrate specificities and structure–activity relationships for the nucleotidylation of antibiotics catalyzed by aminoglycoside nucleotidyltransferase 2"–I, *Biochemistry*, 27: 3820–3825.

George et al., (1992), Inhibition of DNA Helicase II Unwinding and ATPase Activities by DNA–Interacting Ligands, *J.Biol. Chem.*, 267–15:10683–10689.

Giacherio,D. and Hager,L.P. (1979). A Poly(dT)–stimulated ATPase Activity Associated with Simian Virus 40 Large T Antigen, *J. Biol. Chem.*, 254: 8113–8116.

Hachmann,H.J. and Lezius,A.G. (1976). An ATPase depending on the Prescence of Single–Stranded DNA From Mouse Myeloma, *Eur. J. Biochem.*, 61: 325–330.

Henikoff,S. (1993). Transcriptional Activator Components and Poxvirus DNA–dependent ATPases Comprise a Single Family, *TIBS*, 18: 291–292.

Herendeen,D.R., Kassavetis,G.A., Barry,J., Alberts,B.M., and Geiduschek,E.P. (1989). Enhancement of bacteriophage T4 late transcription by components of the T4 DNA replication apparatus, *Science*, 245: 952–958.

Hockensmith,J.W., Kubasek,W.L., Evertsz,E.M., Mesner, L.D., and von Hippel,P.H. (1993). Laser cross–linking of proteins to nucleic acids. II. Interactions of the bacteriophage T4 DNA replication polymerase accessory proteins complex with DNA, *J. Biol. Chem.*, 268: 15721–15730.

Hockensmith,J.W., Wahl,A.F., Kowalski,S., and Bambara, R.A. (1986). Purification of a Calf Thymus DNA–Dependent Adenosinetriphosphatase That Prefers a Primer–Template Junction Effector, *Biochemistry*, 25: 7812–7821.

Hotta,Y. and Stern,H. (1978). DNA Unwinding Protein From Meiotic Cells of Lilium, *Biochemistry*, 17: 1872–1880.

Hu, Guo–Fu, (1998), Neomycin Inhibits Angiogenin–Induced Angiogenesis, *Proc. Natl. Acad. Sci. U.S.A.*, 95:9791–9795, Abstract.

Hu et al., (1997), Accumulation and Dissociation of Human Angiogenin in the Nucleus of Human Endothelial Cells, *Faseb Journal*, II:A319, abstract.

Imbalzano,A.N., Kwon,H., Green,M.R., and Kingston,R.E. (1994). Facilitated binding of TATA–binding protein to nucleosomal DNA., *Nature*, 370: 481–485.

Jarvis,T.C., Paul,L.S., Hockensmith,J.W., and von Hippel, P.H. (1989). Structural and Enzymatic Studies of the T4 DNA Replication System II. ATPase Properties of the Polymerase Accessory Protein Complex, *J. Biol. Chem.*, 264: 12717–12729.

Kolstø,A.–B., Bork,P., Kvaloy,K., Lindback,T., Gronstadt, A., Kristensen,T., and Sander,C. (1993). Prokaryotic Members of a New Family of Putative Helicases with Similarity to Transcriptional Activator SNF2, *J. Mol. Biol.*, 230: 684–688.

Koo,H.S., Claassen,L., Grossman,L., and Liu,L.F. (1991). ATP–dependent partitioning of the DNA template into supercoiled domains by *Escherichia coli* UvrAB, *Proc. Natl. Acad. Sci. U.S.A.*, 88: 1212–1216.

Kunzi,M.S. and Traktman,P. (1989). Genetic Evidence for Involvement of Vaccinia Virus DNA–Dependent ATPase I in Intermediate and Late Gene Expression, *J. Virol.*, 63: 3999–4010.

Kuriyan,J. and O'Donnell,M. (1993). Sliding clamps of DNA polymerases, [Review]. *J. Mol. Biol.*, 234: 915–925.

Kwon,H., Imbalzano,A.N., Khavari,P.A., Kingston,R.E., and Green,M.R. (1994). Nucleosome disruption and enhancement of activator binding by a human SW1/SNF complex, *Nature*, 370: 477–481.

Laemmli,U.K. (1970). Cleavage of Structural Proteins during the Assembly of the Head of Bacteriophage T4, *Nature*, 227: 680–685.

Laurent,B.C., Treich,I., and Carlson,M. (1993). The yeast SNF2/SW12 protein has DNA–stimulated ATPase activity required for transcriptional activation, *Genes Dev.*, 7: 583–591.

Laurent,B.C., Yang,X., and Carlson,M. (1992). An Essential *Saccharomyces cerevisiae* Gene Homologous to SNF2 Encodes a Helicase–Related Protein in a New Family, *Mol. Cell. Biol.*, 12: 1893–1902.

Li,X. and Burgers,P.M.J. (1994). Molecular Cloning and Expression of the *Saccharomyces cerevisiae* RFC3 Gene, an Essential Component of Replication Factor C, *Proc. Natl. Acad. Sci. U. S. A.*, 91: 868–872.

Lohman,T.M., Chao,K., Green,J.M., Sage,S., and Runyon, G.T. (1989). Large–scale Purification and Characterization of the *Escherichia coli* rep Gene Product, *J. Biol. Chem.*, 264: 10139–10147.

Lohman,T.M. and Ferrari,M.E. (1994). *Escherichia coli* single–stranded DNA–binding protein: multiple DNA–binding modes and cooperativities, [Review]. *Annu. Rev. Biochem.*, 63: 527–570.

Lun et al., (1997), Helicase Blockade by CI–958, a drug for Prostate Cancer, *Proc. Annu. Meet. Am. Assoc. Cancer Res.*, 38: A2068.

Lun et al., (1995), DNA Helicase Blockade by Anthracycline Antibiotics, *Proc. Annu. Meet. Am. Assoc. Cancer Res.*, 36: A2091, Abstract.

Matson,S.W. and Kaiser–Rogers,K.A. (1990). DNA Helicases, *Annu. Rev. Biochem.*, 59: 289–329.

Maurin et al., (1996), Bartonella (Rochalimaea) Quintana Infections, *Clinical Microbiology Reviews*, 9(3): 273–292, Summary.

McKay,G.A., Thompson,P.R., and Wright,G.D. (1994). Broad spectrum aminoglycoside phosphotransferase type III from Enterococcus: overexpression, purification, and substrate specificity, *Biochemistry*, 33: 6936–6944.

McKay,G.A. and Wright,G.D. (1995). Kinetic mechanism of aminoglycoside phosphotransferase type IIIa. Evidence for a Theorell–Chance mechanism, *J Biol Chem.*, 270: 24686–24692.

Mesner,L.D., Sutherland,W.M., and Hockensmith,J.W. (1991). DNA–Dependent Adenosinetriphosphatase A Is the Eukaryotic Analogue of the Bacteriophage T4 Gene 44 Protein: Immunological Identity of DNA Replication–Associated ATPases, *Biochemistry*, 30: 11490–11494.

Mesner,L.D., Truman,P.A., and Hockensmith,J.W. (1993). DNA–dependent adenosinetriphosphatase A: immunoaffinity purification and characterization of immunological reagents, *Biochemistry*, 32: 7772–7778.

Meyer,R.R., Brown,C.L., and Rein,D.C. (1984). A New DNA–dependent ATPase from *Escherichia coli*, *J. Biol. Chem.*, 259: 5093–5099.

Morita et al.,1993, DNA packaging ATPase of Bacteriophage T3, *Virology*, 193: 748–752.

Morozov,V.E., Falzon,M., Anderson,C.W., and Kuff,E.L. (1994). DNA–dependent protein kinase is activated by nicks and larger single–stranded gaps, *J. Biol. Chem.*, 269: 16684–16688.

Müller,B., Tsaneva,I.R., and West,S.C. (1993). Branch migration of Holliday junctions promoted by the *Escherichia coli* RuvA and RuvB proteins. II. Interaction of RuvB with DNA, *J. Biol. Chem.*, 268: 17185–17189.

Munn,M.M. and Alberts,B.M. (1991). DNA Footprinting Studies of the Complex Formed by the T4 DNA Polymerase Holoenzyme at a Primer–Template Junction, *J. Biol. Chem.*, 266: 20034–20044.

Munn,M.M. and Alberts,B.M. (1991). The T4 DNA Polymerase Accessory Proteins Form an ATP–dependent Complex on a Primer–Template Junction, *J. Biol. Chem.*, 266: 20024–20033.

Neu, H. C., (1989), Overview of Mechanisms of Bacterial Resistance, *Diagnostic Microbiology and Infectious Diseases*, 12:109S–116S.

Nobile,V., Russo,N., Hu,G., and Riordan,J.F. (1998). Inhibition of human angiogenin by DNA aptamers: nuclear colocalization of an angiogenin–inhibitor complex, *Biochemistry*, 37: 6857–6863.

Ochem et al., (1997), Functional Properties of the Separate Subunits of Human DNA Helicase II/Ku Autoantigen, *J. Biol. Chem.*, 272: 29919–29926.

Oh,E.Y. and Grossman,L. (1989). Characterization of the helicase activity of the *Escherichia coli* UvrAB protein complex, *J. Biol. Chem.*, 264: 1336–1343.

Okabe,I., Bailey,L.C., Attree,O., Srinivasan,S., Perkel,J.M., Laurent,B.C., Carlson,M., Nelson,D.L., and Nussbaum,R.L. (1992). Cloning of Human and Bovine Homologs of SNF2/SWI2: a Global Activator of Transcription in Yeast *S. cerevisiae*, *Nucleic Acids Res.*, 20: 4649–4655.

Pabo,C.O. and Sauer,R.T. (1992). Transcription Factors: Structural Families and Principles of DNA Recognition. *Annu. Rev., Biochem.*, 61: 1053–1095.

Parsons,C.A., Tsaneva,I., Lloyd,R.G., and West,S.C. (1992). Interaction of *Escherichia coli* RuvA and RuvB proteins with synthetic Holliday junctions. *Proc. Natl. Acad. Sci. U.S.A.*, 89: 5452–5456.

Pearson,W.R. and Lipman,D.J. (1988). Improved tools for biological sequence comparison, *Proc. Natl. Acad. Sci. U.S.A.*, 85: 2444–2448.

Pedersen,L.C., Benning,M.M., and Holden,H.M. (1995). Structural investigation of the antibiotic and ATP–binding sites in kanamycin nucleotidyltransferase, *Biochemistry*, 34: 13305–13311.

Peterson,C.L., Dingwall,A., and Scott,M.P. (1994). Five SWI/SNF gene products are components of a large multisubunit complex required for transcriptional enhancement [see comments], *Proc. Natl. Acad. Sci. U.S. A.*, 91: 2905–2908.

Peterson,C.L. and Herskowitz,I. (1992). Characterization of the Yeast SWI1, SWI2, and SWI3 Genes, Which Encode a Global Activator of Transcription, *Cell*, 68: 573–583.

Ratner,D. (1974). The Interaction of Bacterial and Phage Proteins with Immobilized *Escherichia coli* RNA Polymerase, *J. Mol. Biol.*, 88: 373–383.

Richet,E. and Kohiyama,M. (1976). Purification and Characterization of a DNA–dependent ATPase from *Escherichia coli*, *J. Biol. Chem.*, 251: 808–812.

Romaniuk,P.J. (1985). Characterization of the RNA binding properties of transcription factor IIIA of *Xenopus laevis* oocytes, *Nucleic Acids Res.*, 13: 5369–5387.

Roy et al., (1994), The DNA–dependent ATPase Activity Associated with the Class II Basic Transcription Factor BTF2/TFIIH, *Biol. Chem.*, 269: 9826–9832.

Ryan,P.C. and Draper,D.E. (1989). Thermodynamics of Protein–RNA Recognition in a Highly Conserved Region of the Large–Subunit Ribosomal RNA, *Biochemistry*, 28: 9949–9956.

Ryan,P.C., Lu,M., and Draper,D.E. (1991). Recognition of the highly conserved GTPase center of 23 S ribosomal RNA by ribosomal protein L11 and the antibiotic thiostrepton, *J. Mol. Biol.*, 221: 1257–1268.

Sambrook et al., (1989), Molecular Cloning, A Laboratory Manual, Cold Springs Harbor Press, N.Y.

Sancar,A. and Hearst,J.E. (1993). Molecular Matchmakers, *Science*, 259: 1415–1420.

Saxena et al., (1990), Excision repair of UV–damaged plasmid DNA in Xenopus oocytes is mediated by DNA polymerase α (and or δ), *Nucleic Acids Res.*, 18: 7425–7432.

Schägger,H. and Von Jagow,G. (1987). Tricine–Sodium Dodecyl Sulfate–Polyacrylamide Gel Electrophoresis for the Separation of Proteins in the Range from 1 to 100 kDa, *Anal. Biochem.*, 166: 368–379.

Schultz,C., Vajanaphanich,M., Harootunian,A.T., Sammak, P.J., Barrett,K.E., and Tsien,R.Y. (1993). Acetoxymethyl esters of phosphates, enhancement of the permeability and potency of cAMP, *J. Biol. Chem.*, 268: 6316–6322.

Seki,M., Enomoto,T., Eki,T., Miyajima,A., Murakami,Y., Hanaoka,F., and Ui,M. (1990). DNA Helicase and Nucleoside–5'–triphosphatase Activities of Polyoma Virus Large Tumor Antigen, *Biochemistry*, 29: 1003–1009.

Seki,M., Enomoto,T., Watanabe,Y., Tawaragi,Y., Kawasaki, K., Hanaoka,F., and Yamada,M. (1986). Purification and Characterization of a Deoxyribonucleic Acid Dependent Adenosinetriphosphatase From Mouse FM3A Cells: Effects of Ribonucleoside Triphosphates on the Interaction of the Enzyme with Single–Stranded DNA, *Biochemistry*, 25: 3239–3245.

Selby,C.P. and Sancar,A. (1993). Molecular mechanism of transcription–repair coupling, *Science*, 260: 53–58.

Serizawa et al., (1993), Multifunctional RNA Polymerase II Initiation Factor Delta from Rat Liver, *J.Biol. Chem.*, 268–23:17300–17308, Figs. 8 and 9.

Sharp,P.M., Cowe,E., Higgins,D.G., Shields,D.C., Wolfe, K.H., and Wright,F. (1988). Codon Usage Patterns in *Escherichia coli, Bacillus subtilis, Saccharomyces cerevisiae, Schizosaccharomyces pombe, Drosophila melanogaster* and *Homo sapiens*: a review of the considerable within–species diversity, *Nucleic Acids Res.*, 16: 8207–8211.

Shaw,K.J., Rather,P.N., Hare,R.S., and Miller,G.H. (1993). Molecular genetics of aminoglycoside resistance genes and familial relationships of the aminoglycoside–modifying enzymes, *Microbiol.*, Rev 57: 138–163.

Sheridan,P.L., Schorpp,M., Voz,M.L., and Jones,K.A. (1995). Cloning of an SNF2/SWI2–related Protein That Binds Specifically to the SPH Motifs of the SV40 Enhancer and to the HIV–1 Promoter, *J. Biol. Chem.*, 270: 4575–4587.

Simoneau et al., (1998), Helicase–Primase Inhibitors as Novel Anti–HSV Agents, *Book of Abstracts, 216th American Chemical Society*, National Meeting, Boston, Aug. 23–27, abstract.

Steinmetz,E.J. and Platt,T. (1994). Evidence supporting a tethered tracking model for helicase activity of *Escherichia coli* Rho factor, *Proc. Natl. Acad. Sci. U.S.A.*, 91: 1401–1405.

Steitz,T.A. (1990). Structural Studies of Protein–Nucleic Acid Interaction: The Sources of Sequence–Specific Binding, *Q. Rev. Biophys.*, 23: 205–280.

Studier et al., (1990), Use of T7 RNA Polymerase to Direct Expression of Cloned Genes, *Methods Enzymol.*, 185: 60–89.

Sugino,A., Ryu,B.H., Sugino,T., Naumovski,L., and Friedberg,E.C. (1986). A New DNA–dependent ATPase Which Stimulates Yeast DNA Polymerase I and has DNA–unwinding Activity, *J.Biol.Chem.*, 261: 11744–11750.

Sung,P., Prakash,L., Weber,S., and Prakash,S. (1987). The RAD3 gene of *Saccharomyces cerevisiae* encodes a DNA–dependent ATPase, *Proc. Natl. Acad. Sci. U.S.A.*, 84: 6045–6049.

Tawaragi,Y., Enomoto,T., Watanabe,Y., Hanaoka,F., and Yamada,M. (1984). Multiple Deoxyribonucleic Acid Dependent Adenosinetriphosphatases in FM3A Cells. Characterization of an Adenosinetriphosphatase that Prefers Poly [d(A–T)] as Cofactor, *Biochemistry*, 23: 529–533.

Thomas,D.C. and Meyer,R.R. (1982). DNA–dependent ATPases from the Novikoff Hepatoma. Characterization of a Homogeneous ATPase That Stimulates DNA Polymerase–beta, *Biochemistry*, 21: 5060–5068.

Thomas,D.C., Rein,D.C., and Meyer,R.R. (1988). Purification and enzymological characterization of DNA–dependent ATPase IV from the Novikoff hepatoma, 16: 6447–6464.

Tinker,R.L., Williams,K.P., Kassavetis,G.A., and Geiduschek,E.P. (1994). Transcriptional activation by a DNA–tracking protein: structural consequences of enhancement at the T4 late promoter, *Cell*, 77: 225–237.

Towbin,H., Staehelin,T., and Gordon,J. (1979). Electrophoretic Transfer of Proteins from Polyacrylamide gels to Nitrocellulose Sheets: Procedure and Some Applications, *Proc. Natl. Acad. Sci. U.S.A.*, 76: 4350–4354.

Tsuchihashi,Z. and Kornberg,A. (1989). ATP Interactions of the tau and gamma Subunits of DNA Polymerase III Holoenzyme of *Escherichia coli*, *J. Biol. Chem.*, 264: 17790–17795.

Tsuchiya,E., Uno,M., Kiguchi,A., Masuoka,K., Kanemori, Y., Okabe,S., and Mikayawa,T. (1992). The *Saccharomyces cerevisiae* NPS1 Gene, a Novel CDC Gene Which Encodes a 160 kDa Nuclear Protein Involved in G2 Phase Control, *EMBO J.*, 11: 4017–4026.

Tujeta et al., (1997), Inhibition of DNA Unwinding and ATPase activities of Human DNA Helicase II by Chemotherapeutic Agents, *Biochem. Biophys. Res. Comm.*, 236–3:636–640.

Tujeta et al., (1994), Human DNA Helicase II: A Novel DNA Unwinding Enzyme Identified as the Ku Autoantigen, *Embo J.*, 13:4991–5001.

U.S.P. D1 vol. III: Approved Drug Products & Legal Requirements, (1997), 17$^{th}$ Ed., pp. 278–279, Rand McNally, Massachusetts.

Villani et al., (1994), Effect of Major DNA Adduct of the antitumor Drug Cis–Diamminedichloroplatinum (II) on the activity of a Helicase Essential for the DNA Replication, the Herpes Simplex Virus Type–1 origin–binding Protein, *J. Biol. Chem.*, 269–34:21676–21681, Abstract, Fig.5 and Discussion.

Vishwanatha et al., (1995), Characterization of the Hela cell Single Stranded DNA–Dependent ATPase/DNA Helicase II, Mol. and Cell, *Biochem.*, 146:121–126.

Wickens,M. (1990). How the Messenger Got Its Tail: Addition of poly(A) in the Nucleus, *TIBS*, 15: 277–281.

Wickner,S. (1984). DNA–dependent ATPase Activity Associated with Phage P22 Gene 12 Protein, *J. Biol. Chem.*, 259: 14038–14043.

Winston,F. and Carlson,M. (1992). Yeast SNF/SWI Transcriptional Activators and the SPT/SIN Chromatin Connection, *Trends Genet.*, 8: 387–391.

Wong,I. and Lohman,T.M. (1992), Allosteric effects of nucleotide cofactors on *Escherichia coli* Rep helicase–DNA binding, *Science*, 256, 350–355.

Wood,E.R. and Matson,S.W. (1987). Purification and Characterization of a New DNA–dependent ATPase with Helicase Activity from *Escherichia coli.*, *J. Biol. Chem.*, 262: 15269–15276.

Wu,R., Geiduschek,E.P., and Cascino,A. (1975). The Role of Replication Proteins in the Regulation of Bacteriophage T4 Transcription, *J. Mol. Biol.*, 96: 539–562.

Yaginuma,K. and Koike,K. (1981). Properties of a DNA–dependent ATPase From Rat Mitochondria, *Nucleic Acids Res.*, 9: 1949–1961.

Yanagisawa,J., Seki,M., Kohda,T., Enomoto,T., and Ui,M. (1992). DNA–dependent Adenosinetriphosphatase C1 from Mouse FM3A Cells Has DNA Helicase Activity, *J. Biol. Chem.*, 267: 3644–3649.

Yarranton,G.T., Das,R.H., and Gefter,M.L. (1979). Enzyme-Catalyzed DNA Unwinding: A DNA–dependent ATPase from *E. coli.*, *J. Biol. Chem.*, 254: 11997–12001.

Yarranton,G.T., Das,R.H., and Gefter,M.L. (1979). Enzyme-Catalyzed DNA Unwinding: Mechanism of Action of Helicase III, *J. Biol. Chem..*, 254: 12002–12006.

Zavitz,K.H. and Marians,K.J. (1993). Helicase–deficient Cysteine to Glycine Substitution Mutants of *Escherichia coli* Replication Protein PriA Retain Single–Stranded DNA–dependent ATPase Activity, *J Biol Chem.*, 268: 4337–4346.

Zhang,J., Chung,D.W., Tan,C.–K., Downey,K.M., Davie, E.W., and So,A.G., (1991), Primary Structure of the Catalytic Subunit of Calf Thymus DNA Polymerase Delta: Sequence Similarities with Other DNA Polymerases, *Biochemistry*, 30: 11742–11750.

```
   1 atgagcatct ccccattaaa atgtccttgc ctcttacaga ggagcagagg
  51 aaaaaaaatt gaagcaaatc ggcagaaggc tctggcccga agagctgaga
 101 aactattagc agaacagcat cagaaacctg cccagtccaa gcagggccca
 151 tcccaaaacc tcccccgaga tccttctaag tcagggagcc atggcatctt
 201 tttcaaacaa caaaatccca gcagttcatc tcatggtgac cagagacctc
 251 aaaatcccca cagttttcca cccaacacct ctgagcaggc gaaggggatg
 301 tggcagaggc cagaagagat gcccacagcc tgcccaagct accgcccacc
 351 aaatcaagtg actgtcgctg ggatctccct gcccctggca acagtcctc
 401 cagggtccc cagccaacag ctttggggtt gtgagttagg tcaaggtcat
 451 cctcaggctt cactcgagac ccagtcaaca cccttcgcta acacaactca
 501 cgagcctttg cgcaaagtga agaatttcca ggagacagca gcctcttcct 551 ctggacagcc tcctagggat cctgaattag aggccaggat cggaagacct
 601 tccacctctg ggcagaacat ttcggggagt gtgatgccca ggacagaagg
 651 aagactgcaa cagaaagcag ggaccccgat gcacagagtg gtaggctccc
 701 agcagggaag gtgtatccgg aacggagagc gattccaggt gaagattggg
 751 tacaatgagg cgctcatcgc agtgtttaag agtctgccca gcagaagtta
 801 cgatcctgcc accaagacgt ggaacttcag catgactgac tatggtcccc
 851 taatgaaagc agcccagcgc ctcccaggga tcaccctgca gcctttggaa
 901 ggagccgagg ccacatgga gtcaccctcc accagcagtg cattatagc
 951 caagaccggc cttcctgcag ctccctccct ggcctttgtc aaagggcagt
1001 gcgtgctcat ctcccgggcc cgcttcgagg cagacatcag ctattcagaa
1051 gacctgattg cactgtttaa acagatggat tccagaaaat atgatgtcaa
1101 gacccggaag tggagctttc tcctggaaga atacagtaaa ctcatggaaa
1151 gagtgcgcgg ccctccacaa gttcagctgg atcctctgcc caagaccctc
1201 accctytttc gcgctcagct ccagaagacg tctctctctc ctgtggcaga
1251 catccccgag gcagacctgt ccagggtgga ctccaagctt gtgtctagct
1301 tgctgccctt tcagagagct ggagtcaatt tcgctatagc acaaagaggc
1351 cgcctgctgc ttgccgatga catgggcctg gggaagacca tccaagccat
1401 ctgcatagcg gcctattacc ggaaggagtg gcccctcctg gtggtggtgc
1451 cgtcatctgt gcgcttcacc tgggagcagg ccttctgtcg gtggctgccg
```

FIG.1A

```
1501 tctctgaacc cattagacat caacgtcgtg gtaaccggga aggaccgcct
1551 gacagatggc ttggtcaaca ttgtcagttt tgatcttctg agcaagttag
1601 aaaagcagct aaaaccccca tttaaagttg tcatcattga tgaatcccac
1651 ttcctcaaaa acattaagac tgccgtgtgc gcagctatgc ccctcctcaa
1701 ggttgccaag agggtgatct tactgtcagg cacaccagca atgtcccggc
1751 cggcggagct ctacacgcag atcctcgccg tcaggccgac cttcttccct
1801 cagttccatg cctttggact tcgctactgt ggcgccaagc ggcagccctg
1851 gggatgggac tactcgggct cctccaacct gggggagctg aagctcctgc
1901 tagaggaggc ggtcatgctg cgacgcctca agggtgatgt cctctcccag
1951 ctcccagcca agcagccaag atggtggtgg tcgccccagg ccagatcaat
2001 gccaggacca gagccgccct ggatgccgcc cgccaaggag atgaccacca
2051 aggacaaaac taagcagcag caaaaagaag ccctcattct cttcttcaac
2101 agaacagctg aagctaaaat tccatctatc atcgaatata tcctggacct
2151 gctagaaagt ggacgagaga agtttcttgt gtttncgcac cataaggtgg
2201 ttctggatgc aattactaag gagcttgaga ggaagcgcgt gcagcacatc
2251 cgtatcgatg gctccacctc ctcggccgac cgcgagacct ctgccagcag
2301 tttcagttgt ccccgggccc tgcgtggcgt gctgtccatc accgccgcca
2351 acatgggcct caccttctcc tcggctgacc tggtggtgtt cggggagctg
2401 ttttggaacc cgggggtgct gatgcaggct gaggaccggg tgcaccgcat
2451 cggacaattg agctccgtga gcatccacta cctggtggcg agaggcacgg
2501 ctgatgacta cctctggccc ctgattcaag agaagattaa agttctgggt
2551 gaagccgggc tctctgagac caatttttca gaaatgacag aagccacaga
2601 ttacttctcc aaggactcaa agcagcagaa gatctacaac ctattccaga
2651 agtccttcga ggaagacgga aatgatatgg agctcctgga ggcagcagag
2701 tcctttgatc caggttccca ggacacggga gacaagctgg atgaaagcac
2751 attgacgggc agcccagtga agaagaagag atttgaattt tttgataact
2801 gggacagctt tacctctcct ctataagagg agggggaaaa agcattaaaa
2851 ataatggaat ttattactcg tgcc
```

FIG. 1B

```
  1 MSISPLKCPC LLQRSRGKKI EANRQKALAR REAKLLAEQH QKPAQSKQGP
 51 SQNLPRDPSK SGSHGIFFKQ QNPSSSSHGD QRPQNPHSFP PNTSEQAKGM
101 WQRPEEMPTA CPSYRPPNQV TVAGISLPLA NSPPGVPSQQ LWGCELGQGH
151 PQASLETQST PFANTTHEPL RKVKNFQETA ASSSGQPPRD PELEARIGRP
201 STSGQNISGS VMPRTEGRLQ QKAGTPMHRV VGSQQGRCIR NGERFQVKIG
251 YNEALIAVFK SLPSRSYDPA TKTWNFSMTD YGPLMKAAQR LPGITLQPLE
301 GAEGHMESPS TSSGIIAKTG LPAAPSLAFV KGQCVLISRA RFEADISYSE
351 DLIALFKQMD SRKYDVKTRK WSFLLEEYSK LMERVRGPPQ VQLDPLPKTL
401 TLFRAQLQKT SLSPVADIPE ADLSRVDSKL VSSLLPFQRA GVNFAIAQRG
451 RLLLADDMGL GKTIQAICIA AYYRKEWPLL VVVPSSVRFT WEQAFCRWLP
501 SLNPLDINVV VTGKDRLTDG LVNIVSFDLL SKLEKQLKPP FKVVIIDESH
551 FLKNIKTAVC AAMPLLKVAK RVILLSGTPA MSRPAELYTQ ILAVRPTFFP
601 QFHAFGLRYC GAKRQPWGWD YSGSSNLGEL KLLLEEAVML RRLKGDVLSQ
651 LPAKQPRWWW SPQARSMPGP EPPWMPPAKE MTTKDKTKQQ QKEALILFFN
701 RTAEAKIPSI IEYILDLLES GREKFLVFXH HKVVLDAITK ELERKRVQHI
751 RIDGSTSSAD RETSASSFSC PRALRGVLSI TAANMGLTFS SADLVVFGEL
801 FWNPGVLMQA EDRVHRIGQL SSVSIHYLVA RGTADDYLWP LIQEKIKVLG
851 EAGLSETNFS EMTEATDYFS KDSKQQKIYN LFQKSFEEDG NDMELLEAAE
901 SFDPGSQDTG DKLDESTLTG SPVKKKRFEF FDNWDSFTSP L*
```

FIG.2

```
201                TEGRLQ  QKAGTPMHRV  VGSQQGRCIR  NGERFQVKIG
251  YNEALIAVFK  SLPSRSYDPA  TKTWNFSMTD  YGPLMKAAQR  LPGITLQPLE
301  GAEGHMESPS  TSSGIIAKTG  LPAAPSLAFV  KGQCVLISRA  RFEADISYSE
351  DLIALFKQMD  SRKYDVKTRK  WSFLLEEYSK  LMERVRGPPQ  VQLDPLPKLT
401  TLFRAQLQKT  SLSPVADIPE  ADLSRVDSKL  VSSLLPFQRA  GVNFAIAQRG
451  RLLLADDMGL  GKTIQAICIA  AYYRKEWPLL  VVVPSSVRFT  WEQAFCRWLP
501  SLNPLDINVV  VTGKDRLTDG  LVNIVSFDLL  SKLEKQLKPP  FKVVIIDESH
551  FLKNIKTAVC  AAMPLLKVAK  RVILLSGTPA  MSRPAELYTQ  ILAVRPTFFP
601  QFHAFGLRYC  GAKRQPWGWD  YSGSSNLGEL  KLLLEEAVML  RRLKGDVLSQ
651  LPAKQPRWWW  SPQARSMPGP  EPPWMPPAKE  MTTKDKTKQQ  QKEALILFFN
701  RTAEAKIPSI  IEYILDLLES  GREKFLVFXH  HKVVLDAITK  ELERKRVQHI
751  RIDGSTSSAD  RETSASSFSC  PRALRGVLSI  TAANMGLTFS  SADLVVFGEL
801  FWNPGVLMQA  EDRVHRIGQL  SSVSIHYLVA  RGTADDYLWP  LIQEKIKVLG
351  EAGLSETNFS  EMTEATDYFS  KDSKQQKIYN  LFQKSFEEDG  NDMELLEAAE
901  SFDPGSQDTG  DKLDESTLTG  SPVKKKRFEF  FDNWDSFTSP  L*
```

FIG. 3

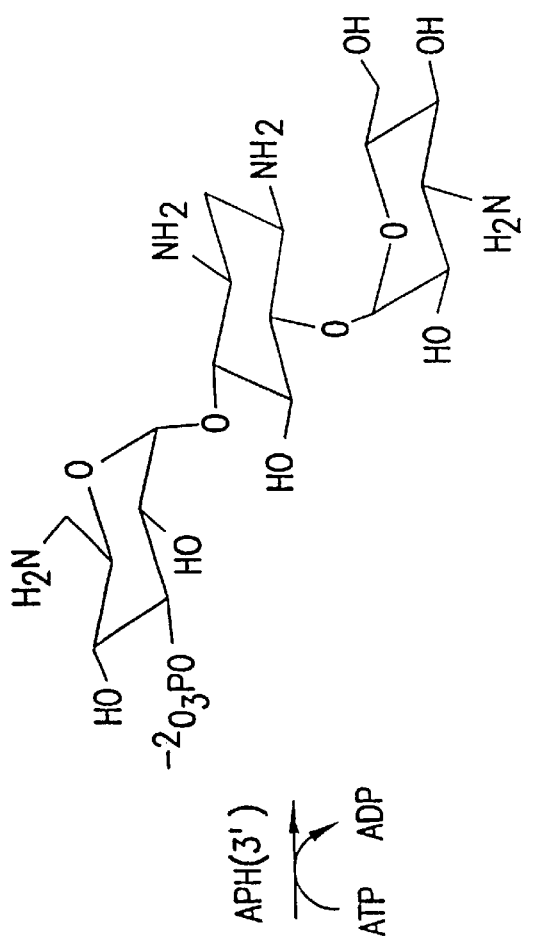
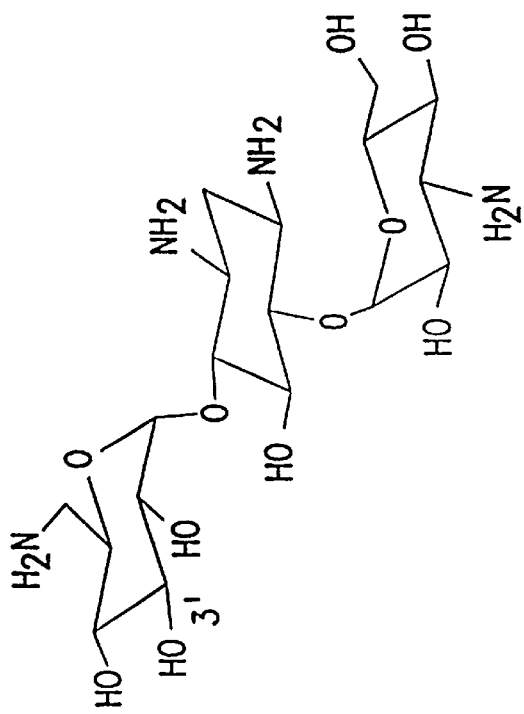
FIG. 4

```
  1 GAGCTGTACA CCCAGATCCT CGCCGTCAGG CCGACCTTCT
 51 TCCCTCAGTT CCATGCCTTT
```

```
  1 ELYTQILAVR PTFFPQFHAF
```

FIG.13

```
  1 CATGGGCCTG GGGAAGACCA TCCAAGCCAT CTGCATAGCG GCCTATTACC
 51 GGAAGGAGTG GCCCCTCCTG GTGGTGGTGC CGTCATCTGT GCGCTTCACC
101 TGGGAGCAGG CCTTCTGTCG GTGGCTGCCG TCTCTGAACC CATTAGACAT
151 CAACGTCGTG GTAACCGGGA AGGACCGCCT GACAGATGGC TTGGTCAACA
201 TTGTCAGTTT TGATCTTCTG AGCAAGTTAG AAAAGCAGCT AAAACCCCCA
251 TTTAAAGTTG TCATCATTGA TGAATCCCAC TTCCTCAAAA ACATTAAGAC
301 TGCCGTGTGC GCAGCTATGC CCCTCCTCAA GGTTGCCAAG AGGGTGATCT
351 TACTGTCAGG CACACCAGCA ATGTCCCGGC CGGCGGAGCT CTACACGCAG
401 ATCCTCGCCG TCAGGCCGAC CTTCTTCCCT
```

```
  1 MGLGKTIQAI CIAAYYRKEW PLLVVVPSSV RFTWEQAFCR WLPSLNPLDI
 51 NVVVTGKDRL TDGLVNIVSF DLLSKLEKQL KPPFKVVIID ESHFLKNIKT
101 AVCAAMPLLK VAKRVILLSG TPAMSRPAEL YTQILAVRPT
```

FIG.14 gtatgtttaa ttttaaaaga aattttaata tatcctttgt ttatactcct
tgtgcatttc ctgggacaaa agcttgttga aatcaaggta agcaaaaaaa
aattttttta attaatgtct atttccatgt tgtttttcct ttctcagctt
ttgccaagtt tccgattaca gactgacatt cctgc

```
   1 ATGAGCATCT CCCCATTAAA ATGTCCTTGC CTCTTACAGA GGAGCAGAGG
  51 AAAAAAAATT GAAGCAAATC GGCAGAAGGC TCTGGCCCGA AGAGCTGAGA
 101 AACTATTAGC AGAACAGCAT CAGAAACCTG CCCAGTCCAA GCAGGGCCCA
 151 TCCCAAAACC TCCCCCGAGA TCCTTCTAAG TCAGGGAGCC ATGGCATCTT
 201 TTTCAAACAA CAAAATCCCA GCAGTTCATC TCATGGTGAC CAGAGACCTC
 251 AAAATCCCCA CAGTTTTCCA CCCAACACCT CTGAGCAGGC GAAGGGGATG
 301 TGGCAGAGGC CAGAAGAGAT GCCCACAGCC TGCCCAAGCT ACCGCCACCC
 351 AAATCAAGTG ACTGTCGCTG GGATCTCCCT GCCCCTGGCA AACAGTCCTC
 401 CAGGGGTCCC CAGCCAACAG CTTTGGGGTT GTGAGTTAGG TCAAGGTCAT
 451 CCTCAGGCTT CACTCGAGAC CCAGTCAACA CCCTTCACTA ACACAACTCA
 501 CGAGCCTTTG CGCAAAGTGA AGAATTTCCA GGAGACAGCA GCCTCTTCCT
 551 GTGGACAGCC TCCTAGGGAT CCTGAATTAG AGGCCAGGAT CGGAAGACCT
 601 TCCACCTCTG GGCAGAACAT TCGGGGAGT GTGATGCCCA GGACAGAAGG
 651 AAGACTGCAA CAGAAAGCAG GGACCCCGCT GCACAGAGTG GTAGGCTCCC
 701 AGCAGGGAAG GTGTATCCGG AACGGAGAGC GATTCCAGGT GAAGATTGGG
 751 TACAATGAGG CGCTCATCGC AGTGTTTAAG AGTCTGCCCA GCAGAAGTTA
 801 CGATCCTGCC ACCAAGACGT GGAACTTCAG CATGACTGAC TATGGTCCCC
 851 TAATGAAAGC AGCCCAGCGC CTCCCAGGGA TCACCCTGCA GCCTTTGGAA
 901 GGAGCCGAGG GCCACATGGA GTCACCCTCC ACCAGCAGTG GCATTATAGC
 951 CAAGACCGGC CTTCCTGCAG CTCCCTCCCT GGCCTTTGTC AAAGGGCAGT
1001 GCGTGCTCAT CTCCCGGGCC CGCTTCGAGG CAGACATCAG CTATTCAGAA
1051 GACCTGATTG CACTGTTTAA ACAGATGGAT TCCAGAAAAT ATGATGTCAA
1101 GACCCGGAAG TGGAGCTTTC TCCTGGAAGA ATACAGTAAA CTCATGGAAA
1151 GAGTGCGCGG CCCTCCACAA GTTCAGCTGG ATCCTCTGCC CAAGACCCTC
1201 ACCCTYTTTC GCGCTCAGCT CCAGAAGACG TCTCTCTCTC CTGTGGCAGA
1251 CATCCCCGAG GCAGACCTGT CCAGGGTGGA CTCCAAGCTT GTGTCTAGCT
1301 TGCTGCCCTT TCAGAGAGCT GGAGTCAATT TCGCTATAGC ACAAAGAGGC
1351 CGCCTGCTGC TTGCCGATGA CATGGGCCTG GGGAAGACCA TCCAAGCCAT
1401 CTGCATAGCG GCCTATTACC GGAAGGAGTG GCCCCTCCTG GTGGTGGTGC
1451 CGTCATCTGT GCGCTTCACC TGGGAGCAGG CCTTCTGTCG GTGGCTGCCG
1501 TCTCTGAACC CATTAGACAT CAACGTCGTG GTAACCGGGA AGGACCGCCT
1551 GACAGATGGC TTGGTCAACA TTGTCAGTTT TGATCTTCTG AGCAAGTTAG
1601 AAAAGCAGCT AAAACCCCCA TTTAAAGTTG TCATCATTGA TGAATCCCAC
1651 TTCCTCAAAA ACATTAAGAC TGCCGTGTGC GCAGCTATGC CCCTCCTCAA
1701 GGTTGCCAAG AGGGTGATCT TACTGTCAGG CACACCAGCA ATGTCCCGGC
1751 CGGCGGAGCT CTACACGCAG ATCCTCGCCG TCAGGCCGAC CTTCTTCCCT
1801 CAGTTCCATG CCTTTGGACT TCGCTACTGT GGCGCCAAGC GGCAGCCCTG
1851 GGGATGGGAC TACTCGGGCT CCTCCAACCT GGGGGAGCTG AAGCTCCTGC
1901 TAGAGGAGGC GGTCATGCTG CGACGCCTCA AGGGTGATGT CCTCTCCCAG
1951 CTCCCAGCCA AGCAGCCAAG ATGGTGGTGG TCGCCCCAGG CCAGATCAAT
2001 GCCAGGACCA GAGCCGCCCT GGATGCCGCC CGCCAAGGAG ATGACCACCA
2051 AGGACAAAAC TAAGCAGCAG CAAAAAGAAG CCCTCATTCT CTTCTTCAAC
2101 AGAACAGCTG AAGCTAAAAT TCCATCTATC ATCGAATATA TCCTGGACCT
2151 GCTAGAAAGT GGACAGAGAA AGTTTCTTGT GTTTGCGCAC CATAAGGTGG
2201 TTCTGGATGC AATTACTAAG GAGCTTGAGA GGAAGCGCGT GCAGCACATC
2251 CGTATCGATG GCTCCACCTC CTCGGCCGAC CGCGAGACCT CTGCCAGCAG
2301 TTTCAGTTGT CCCCGGGCCC TGCGTGGCGT GCTGTCCATC ACCGCCGCCA
2351 ACATGGGCCT CACCTTCTCC TCGGCTGACC TGGTGGTGTT CGGGGAGCTG
```

FIG.17A

2401 TTTTGGAACC CGGGGGTGCT GATGCAGGCT GAGGACCGGG TGCACCGCAT
2451 CGGACAATTG AGCTCCGTGA GCATCCACTA CCTGGTGGCG AGAGGCACGG
2501 CTGATGACTA CCTCTGGCCC CTGATTCAAG AGAAGATTAA AGTTCTGGGT
2551 GAAGCCGGGC TCTCTGAGAC CAATTTTTCA GAAATGACAG AAGCCACAGA
2601 TTACTTCTCC AAGGACTCAA AGCAGCAGAA GATCTACAAC CTATTCCAGA
2651 AGTCCTTCGA GGAAGACGGA AATGATATGG AGCTCCTGGA GGCAGCAGAG
2701 TCCTTTGATC CAGGTTCCCA GGACACGGGA GACAAGCTGG ATGAAAGCAC
2751 ATTGACGGGC AGCCCAGTGA AGAAGAAGAG ATTTGAATTT TTTGATAACT
2801 GGGACAGCTT TACCTCTCCT CTATAA gaggaggggg aaaaagcatt aaaaataatg gaatttatta ctcgtgcc

FIG.17B

```
  1 CCCCCCCCCA CCCCCCCCCC CCCCCCCCCC CCCCCCCCCT CCCCCCCTCC
 51 CCCCCCCCCC CCCCCCGGCC TTTTTCCCCC CCCCCCCGCC CTTTTTCCCC
101 TCCCTTCCAC CCCCCCGACT TCCCCCCCCC GCCCCCCACC CGCACCCCCG
151 GGGCCGGACC ACTCGGGTTC TCCCAACCCG GGGACCCGAA CTTCCCGCCA
201 GCGGCGCGCT CACCCCCGAA CCCTTCAAGG CGACTTCTTT TTCCCAGTTC
251 CCACCCAAGA GCCAAGATGG TGGTGGTTCC CCCAGCCCAG ATCAATGCCA
301 GGACCAGACC CCCCCTGGAT CCCCCCGCCC AAGGAGATGA CCACCAAGGA
351 CAAAACTAAG CAGCAGCAAA AAGAAGCCTT CATTTTCTTC TTTCAACAGA
401 ACAGCTGAAG CTAAAATTCC ATCTATCATC GAATATATCC TGGACCTGCT
451 AGAAAGTGGA CGAGAGAAGT TCTTGTGTT TGCGCACCAT AAGGTGGTTC
501 TGGATGCAAT TACTAAGGAG CTTGAGAGGA AGCGCGTGCA GCACATCCGT
551 ATCGATGGCT CCACCTCCTC GGCCGACCGC GAGGACCTCT GCCAGCAGTT
601 TCAGTTGTCC CCGGGCCCTG CCGTGGCCGT GCTGTCCATC ACCGCCGCCA
651 ACATGGGCCT CATCTTCTCC TCGGCTGACC TGGTGGTGTT CGGGGAGCTG
701 TTTTGGAACC CGGGGGGTGCT GATGCAGGCT GAGGACCGGG TGCACCGCAT
751 CGGACAGTTG AGCTCCGTGA GCATCCACCA CCTGGTGGCG AGAGGCACGG
801 CTGATGACTA CCTCTGGCCC CTGATTCAAG AGAAGATTAA AGTTCTGGGT
851 GAAGCCGGGC CCCTGAGAC CAATTTTTCA GAAATGACAG AAGCCACAAA
901 TTATTCTCCA AGGATCAAAG CAGCAGAAGA TCTAAA
```

FIG.19

```
CALF THYMUS   1750       1760       1770       1780       1790       1800
      CODING CCCGGCCCCCCCACCTCTACACCCACATCCTCCCCCTCACCCCCACCTTCTT-CCCTCAG
             || ||   |   ||| |||| || |||||
      ak505. CCCTCCCCCCCCCCCCCCCCCCCCCCTTTTTCCCCCCCCCCCCGCCCTTTTTCCCCTCCC
              50         60         70         80         90         100

1810       1820       1830       1840       1850       1860
      CODING TTCCATCCCTTTGGACTTCGCTACTGTGGCGCCAAGCGGCAGCCCTGGCCATCCCACTAC
             ||||| ||   ||||||| |   |  |  | | |||  ||| |||| |  |||| ||
      ak505. TTCCA-CCCCCCCGACTTCCCCCCCCCCCCCCCCCCCACCCCCACCCCCGGGG-CCGGACCAC
              110        120        130        140        150        160

1870       1880       1890       1900       1910       1920
      CODING TCGGGCTCCTCCAACCTCCCCCACCTGAAGCTCCTGCTAGAGGAGGCGGTCATGCTGCGA
             ||||| ||  ||||||   |||||   |||  |||  || ||  ||| |||   |    |    |
      ak505. TCGGGTTCTCCCAACC-CCCCCACCCCAACTTCCCGCCAGCGG-CGCGCTCACCCCCGAA
              170        180        190        200        210        220

1930       1940       1950       1960       1970       1980
      CODING CGCCTCAACCCTCATGTCCTCTCCCACCTCCCAGCCAAGCAGCCAAGATGGTGGTGGTCC
             ||  ||||||     |    | |||||||  ||||| |||||  ||||||||||||||||||
      ak505. CCCTTCAAGGCGACTTCTTTTTCCCAGTTCCCACCCAAG-AGGCAAGATCCTCCTCCTTC
              230        240        250        260        270

1990       2000       2010       2020       2030       2040
      CODING CCCCAGGCCAGATCAATGCCAGGACCAGAGCCGCCCTGGATGGCCCCCCCCAACCACATC
             |||||| |||||||||||||||||||||||| || ||||||||| || ||  ||||||||||
      ak505. CCCCAGCCCAGATCAATGCCAGGACCAGACCCCCCCTGGATCCCCCCCCCCAACCAGATC
              280        290        300        310        320        330

2050       2060       2070       2080       2090       2100
      CODING ACCACCAAGGACAAAACTAAGCAGCAGCAAAAAGAAGCCCTCATTCTCTTC-TTCAACAG
             |||||||||||||||||||||||||||||||||||||||| ||||| ||||| ||||||||
      ak505. ACCACCAAGGACAAAACTAAGCAGCAGCAAAAAGAAGCCTTCATTTTCTTCTTTCAACAC
              340        350        360        370        380        390

2110       2120       2130       2140       2150       2160
      CODING AACACCTGAAGCTAAAATTCCATCTATCATCGAATATATCCTCCACCTGCTAGAAAGTGG
             |||| |||||||||||||||||||||||||||||||||||||| |||||||||||||| ||
      ak505. AACAGCTGAAGCTAAAATTCCATCTATCATCGAATATATCCTGGACCTGCTAGAAACTCC
              400        410        420        430        440        450

2170       2180       2190       2200       2210       2220
      CODING ACGAGAGAAGTTTCTTGTGTTTNCGCACCATAAGGTCCTTCTGGATGCAATTACTAACCA
             |||||||||||||||||||||||| |||||||||||||||||||||||||||||||||||
      ak505. ACGAGAGAAGTTTCTTGTGTTTGCGCACCATAAGGTCCTTCTGGATGCAATTACTAACCA
              460        470        480        490        500        510
```

FIG.20A

```
              2230      2240      2250      2260      2270      2280
CODING  GCTTGAGAGGAACCCCGTGCAGCACATCCGTATCCATCGCTCCACCTCCTCGGCCCACCC
        ||||||||||   |  ||||||||||||| ||||||| |||||||||||||||  | ||||
ak505   GCTTGAGACCAAGCGCGTGCAGCACATCCCTATCGATGGCTCCACCTCCTCCCCCCACCC
              520       530       540       550       560       570

2290      2300      2310      2320      2330      2339
CODING  CCA-GACCTCTGCCAGGACTTTCAGTTGTCCCCGGGCCCTC-CCTGG-CGTGCTGTCCAT
        |||  |||||||||  ||||||||||||||||||||  ||||  |||||  |||||||||
ak505   CGAGGACCTCTCCCACCAGTTTCAGTTGTCCCCCGGCCCTGCCGTGGCCGTCCTCTCCAT
              530       590       600       610       620       630

2340      2350      2360      2370      2380      2399
CODING  CACCGCCGCCAACATGCCCCTCACCTTCTCCTCGGCTGACCTGGTGGTGTTCGGGGAGCT
        |||||||||||||||||||||| ||| ||||||||||||||||||||||||||||||||
ak505   CACCGCCGCCAACATGCCCCTCATCTTCTCCTCGGCTGACCTGGTGGTGTTCGGGGAGCT
              640       650       660       670       680       690

2400      2410      2420      2430      2440      2450      2459
CODING  GTTTTCCAACCCGGGGGGTGCTCATCCAGGCTGAGGACCGGGTCCACCGCATCGGACAATT
        ||||| ||||||||||||||||| || |||||||||| |||||||||||||||||||| ||
ak505   GTTTTGGAACCCGGGGGGTGCTGATGCAGGCTCACCACCGGGTGCACCGCATCGGACAGTT
              700       710       720       730       740       750

2460      2470      2480      2490      2500      2510      2519
CODING  GAGCTCCCTCAGCATCCACTACCTGGTCCCGAGAGGCACGGCTGATCACTACCTCTGGCC
        |||||| |||| ||||||||| |||||| ||||||||| |||||| |||||||||||||
ak505   CAGCTCCGTGAGCATCCACCACCTGGTGGCGAGAGGCACGGCTCATGACTACCTCTGGCC
              760       770       780       790       800       810

2520      2530      2540      2550      2560      2570      2579
CODING  CCTGATTCAACACAAGATTAAAGTTCTGGGTCAACCCGGGCTCTCTGAGACCAATTTTTC
        ||| |||||| || ||||||||| ||||||| ||| |||||  | |||||||||||||||
ak505   CCTCATTCAAGAGAAGATTAAACTTCTGGGTGAAGCCGGGCCCCCTGAGACCAATTTTTC
              820       830       840       850       860       870

2590      2590      2600      2610      2620      2630      2639
CODING  ACAAATGACAGAAGCCACACATTACTTCTCCAAGGACTCAAACCACCAGAAGATCTACAA
        |||||| |||||||||||| ||| |||||||||||| |||||||||||| ||||||  |
ak505   ACAAATCACAGAAGCCACAAATTA-TTCTCCAAGGA-TCAAACCACCACAAGATCTAAA
              880       890       900       910       920       930

2640      2650      2660      2670      2650      2690      2699
CODING  CCTATTCCAGAAGTCCTTCGAGCAACACCGAAATGACATGGACCTCCTCCAGGCAGCAGA
```

FIG.20B

```
thymus           570        580        590        600        610        620
coding.pep  LKVAKRVILLSGTPAMSRPAELYTQILAVRPTFFPQFHAFGLRYCGAKRQPWGWDYSGSS
                                        |  ||::   |    :  : :| |
ak505pep2        PPPPPPPPPPPPPPPLPPPPPPAFFPPPPPFFPSLPPPRLPPPAPHPHPRGRTTRVLP
                      10         20         30         40         50 calf thymus      630        640        650        660        670        680
coding.pep  NLGELKLLLEEAVMLRRLKGDVLSQLPAKQPRWWWSPQARSMPGPEPPWMPPAKEMTTKD
             :  |  :|    |:  : :|:  :||:| |:     || :     || |   ::    :
ak505pep2   TRGP-ELPASGALTPEPFKATSFSQFPPKSQDGGGSPSPDQCQDQTPPGSPRPRRXPPRT
             60        70         80        90       - 100       110

690        700        710        720     -  730        740
coding.pep  KTKQQQKEALILFFNRTAEAKIPSIIEYILDLLESGREKFLVFXHHKVVLDAITKELERK
             |  ::::|:   :  ||||||||||||||||||||||||| ||||||||||||||||||
ak505pep2   KLSSSKKKPSFSSFNRTAEAKIPSIIEYILDLLESGREKFLVFAHHKVVLDAITKELERK
                 120        130        140        150        160        170

750        760        770        780        790        800
coding.pep  RVQHIRIDGSTSSADRETSASSFS-CPRALRGVLSITAANMGLTFSSADLVVFGELFWNP
            ||||||||||||||||||      ::|:   |     :||||||||| ||||||||||||
ak505pep2   RVQHIRIDGSTSSADREDLCQQFQLSPGPAVAVLSITAANMGLIFSSADLVVFGELFWNP
                 180        190        200        210        220        230

810        820        830        840        850        860
coding.pep  GVLMQAEDRVHRIGQLSSVSIHYLVARGTADDYLWPLIQEKIKVLGEAGLSETNFSEMTE
            |||||||||||||||||||||:||||||||||||||||||||||||||  ||||||||
ak505pep2   GVLMQAEDRVHRIGQLSSVSIHHLVARGTADDYLWPLIQEKIKVLGEAGPPETNFSEMTE
                 240        250        260        270        280        290

870        880        890        900        910        920
coding.pep  ATDYFSKDSKQQKIYNLFQKSFEEDGNDMELLEAAESFDPGSQDTGDKLDESTLTGSPVK
            ||:|
ak505pep2   ATNYSPRIKAAEDL
                 300        310
```

FIG.21

```
                            SEQUENCE LISTING (1) GENERAL INFORMATION:

(iii) NUMBER OF SEQUENCES: 66

(2) INFORMATION FOR SEQ ID NO: 1:

(i) SEQUENCE CHARACTERISTICS:
        (A) LENGTH: 38 base pairs
        (B) TYPE: nucleic acid
        (C) STRANDEDNESS: single
        (D) TOPOLOGY: circular (ii) MOLECULE TYPE: Other (xi) SEQUENCE DESCRIPTION: SEQ ID NO: 1:

GCGCAATTGC GCTCGACGAT TTTTTAGCGC AATTGCGC                                38

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 2:

CCCCCCCCCC CCCCCTCGAT GTCGACTCGA GTC                                     33

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 3:

GACTCGAGTC GACTTTTTTT TTTGGGGGGG GGG                                     33
```

(2) INFORMATION FOR SEQ ID NO: 4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 4:

ATGTCGACTC GAGTC                                                15

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 5:

AGCTTTACCT CTCCTCTATA AGAATTCGAG C                      31

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 6:

GCTCGAATTC TTATAGAGGA GAGGTAAAGC T                      31

(2) INFORMATION FOR SEQ ID NO: 7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 7:

GACTCGAGTC GAC                                                  13

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 8:

GACTCGAGTC GACATCGAGG GGGGGGGGGG GGG                    33

(2) INFORMATION FOR SEQ ID NO: 9:

(i) SEQUENCE CHARACTERISTICS:
    (A) LENGTH: 12 base pairs
    (B) TYPE: nucleic acid
    (C) STRANDEDNESS: double
    (D) TOPOLOGY: linear (ii) MOLECULE TYPE: Other (xi) SEQUENCE DESCRIPTION: SEQ ID NO: 9:

GCGCAATTGC GC                                                                12

(2) INFORMATION FOR SEQ ID NO: 10:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Ser Arg Pro Ala Glu Leu Tyr Thr Gln Ile Leu Ala Val Arg Pro Thr
 1               5                  10                  15

Phe Phe Pro Gln Phe His Ala Phe Gly Leu Arg Tyr Xaa Gly Ala Lys
            20                  25                  30

Arg Gln Pro
        35

(2) INFORMATION FOR SEQ ID NO: 11:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Pro Leu Leu Lys Val Ala Lys Arg Val Ile Leu Leu Ser Gly Thr Pro
 1               5                  10                  15

Ala (2) INFORMATION FOR SEQ ID NO: 12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Glu Arg Val Arg Gly Leu Pro Gln Val Thr Leu Gln Pro Leu Pro Lys
 1               5                  10                  15

(2) INFORMATION FOR SEQ ID NO: 13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Lys Ala Ala Gln Arg Leu Pro Gly Ile Thr Leu Gln Pro Leu Glu
 1               5                  10                  15

(2) INFORMATION FOR SEQ ID NO: 14:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 14:

Gly Leu Gly Lys Thr Ile Gln Ala Ile Xaa Ile Ala Ala Tyr Tyr Arg
 1               5                  10                  15

Lys Glu Xaa Pro Leu Leu Val Val Val Pro
            20                  25

(2) INFORMATION FOR SEQ ID NO: 15:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 15:

Thr Thr Lys Asp Lys Thr Lys Gln Gln Gln Lys Glu Ala Leu Ile Leu
 1               5                  10                  15

Phe Phe Xaa Arg Thr Ala Glu Ala Lys Ile
            20                  25

(2) INFORMATION FOR SEQ ID NO: 16:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Thr Glu Gly Arg Leu Gln Gln Lys Ala Gly Thr Pro Met His Arg Val
 1               5                  10                  15

Val Gly Ser Gln Gln
            20

(2) INFORMATION FOR SEQ ID NO: 17:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Ala Gly Thr Pro Met His Arg Val Val Gly Ser Gln Gln Gly Arg Cys
 1               5                  10                  15

Ile Arg Asn Gly Glu (2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 18:

TTCTTCCCCC AGTTCCAT                                                18

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 19:

AAAGGCATGG AACTG                                                   15

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 20:

TCCCTGACTT AGAAGGATCT C                                            21

(2) INFORMATION FOR SEQ ID NO: 21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 21:

CCCTGCTTGG ACTGGGCAG                                               19

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 22:

TTGGGGTTGT GAGTTAGGTC A                                            21

(2) INFORMATION FOR SEQ ID NO: 23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 23:

CTTCCAGGAG AAAGCTCCAC                                                    20

(2) INFORMATION FOR SEQ ID NO: 24:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 24:

AGATATCATA TGAGCATCTC CCCATTAAAA                                         30

(2) INFORMATION FOR SEQ ID NO: 25:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 25:

TCTTCCAAAG GCTGCAGGG                                                     19

(2) INFORMATION FOR SEQ ID NO: 26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 26:

CCAGCAGAAG TTACGATCCT G                                                  21

(2) INFORMATION FOR SEQ ID NO: 27:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 27:

GTTTTCCCAG TCACGAC                                                       17

(2) INFORMATION FOR SEQ ID NO: 28:

(i) SEQUENCE CHARACTERISTICS:
            (A) LENGTH: 17 base pairs
            (B) TYPE: nucleic acid

```
        (C) STRANDEDNESS: single
        (D) TOPOLOGY: linear (ii) MOLECULE TYPE: Other (xi) SEQUENCE DESCRIPTION: SEQ ID NO: 28:

CAGGAAACAG CTATGAC                                                    17

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 29:

AGGAGGCTGT CCAGAGGAAG                                                 20

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 30:

CAGGCTGTGG GCATCTCTTC                                                 20

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 31:

TCGAATTCTA TTACCGGAAG GA                                              22

(2) INFORMATION FOR SEQ ID NO: 32:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 32:

GAGCTCTACA CGCAGAT                                                    17

(2) INFORMATION FOR SEQ ID NO: 33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other
```

(xi) SEQUENCE DESCRIPTION: SEQ ID NO: 33:

GACTCGAGTC GACATCGAGG GGGGGGGGGG GGG                33

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 34:

AGGGAAGAAG GTCGGCCTGA C                            21

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 35:

CTCGCCGTCA GGCCGACCTT                              20

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 36:

ATGGGCCTGG GCAAGACCAT                              20

(2) INFORMATION FOR SEQ ID NO: 37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 37:

GACTCGAGTC GACATCG                                 17

(2) INFORMATION FOR SEQ ID NO: 38:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 38:

GACTCGAGTC GACATCGATT TTTTTTTTTT TTTTT              35

(2) INFORMATION FOR SEQ ID NO: 39:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO: 39:

GGGCTTAAAT TGGTCAACGA                                           20

(2) INFORMATION FOR SEQ ID NO: 40:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO: 40:

GAGTCCCGTC CTTTGCTGAC                                           20

(2) INFORMATION FOR SEQ ID NO: 41:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO: 41:

AGGAGATGAC CACCAAGGAC A                                         21

(2) INFORMATION FOR SEQ ID NO: 42:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO: 42:

GCTCGAATTC TTATAGAGGA GAGGTAAAGC T                              31

(2) INFORMATION FOR SEQ ID NO: 43:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO: 43:

TATACCATGG CAGGGACCCC GATGCACAGA                                30

(2) INFORMATION FOR SEQ ID NO: 44:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO: 44:

AGTCCTTTGA TCCAGGTTCC C                                       21

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 45:

TCGAAGGACT TCTGGAATAG G                                       21

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 46:

GAGGAGAGGT AAAGCTGTCC C                                       21

(2) INFORMATION FOR SEQ ID NO: 47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 47:

GCTCCCAGGT GAAGCGCAC                                          19

(2) INFORMATION FOR SEQ ID NO: 48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 48:

GCTCGAATTC ATGAGCATCT CCCCATTAAA                              30

(2) INFORMATION FOR SEQ ID NO: 49:

(i) SEQUENCE CHARACTERISTICS:
        (A) LENGTH: 24 base pairs
        (B) TYPE: nucleic acid
        (C) STRANDEDNESS: single -continued

```
        (D) TOPOLOGY: linear (ii) MOLECULE TYPE: Other (xi) SEQUENCE DESCRIPTION: SEQ ID NO: 49:

TTCTCAGCTT TTGCCAAGTT TCCG                                              24

(2) INFORMATION FOR SEQ ID NO: 50:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO: 50:

ACCATCCAGG CCATCTCCAT TGCT                                              24

(2) INFORMATION FOR SEQ ID NO: 51:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO: 51:

GTAGTAGGCA GCAATGGAGA TGGC                                              24

(2) INFORMATION FOR SEQ ID NO: 52:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 52:

Glu Leu Tyr Thr Gln Ile
 1               5

(2) INFORMATION FOR SEQ ID NO: 53:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 53:

Gln Phe His Ala Phe
 1               5

(2) INFORMATION FOR SEQ ID NO: 54:

(i) SEQUENCE CHARACTERISTICS:
         (A) LENGTH: 2874 base pairs
         (B) TYPE: nucleic acid
         (C) STRANDEDNESS: double
         (D) TOPOLOGY: linear
```

(ii) MOLECULE TYPE: Other (xi) SEQUENCE DESCRIPTION: SEQ ID NO: 54:

```
ATGAGCATCT CCCCATTAAA ATGTCCTTGC CTCTTACAGA GGAGCAGAGG AAAAAAAAT      60
GAAGCAAATC GGCAGAAGGC TCTGGCCCGA AGAGCTGAGA AACTATTAGC AGAACAGCAT    120
CAGAAACCTG CCCAGTCCAA GCAGGGCCCA TCCCAAAACC TCCCCCGAGA TCCTTCTAAG    180
TCAGGGAGCC ATGGCATCTT TTTCAAACAA CAAAATCCCA GCAGTTCATC TCATGGTGAC    240
CAGAGACCTC AAAATCCCCA CAGTTTTCCA CCCAACACCT CTGAGCAGGC GAAGGGGATG    300
TGGCAGAGGC CAGAAGAGAT GCCCACAGCC TGCCCAAGCT ACCGCCCACC AAATCAAGTG    360
ACTGTCGCTG GGATCTCCCT GCCCCTGGCA ACAGTCCTC CAGGGGTCCC CAGCCAACAG     420
CTTTGGGGTT GTGAGTTAGG TCAAGGTCAT CCTCAGGCTT CACTCGAGAC CCAGTCAACA    480
CCCTTCGCTA ACACAACTCA CGAGCCTTTG CGCAAAGTGA AGAATTTCCA GGAGACAGCA    540
GCCTCTTCCT CTGGACAGCC TCCTAGGGAT CCTGAATTAG AGGCCAGGAT CGGAAGACCT    600
TCCACCTCTG GCAGAACAT TTCGGGGAGT GTGATGCCCA GGACAGAAGG AAGACTGCAA     660
CAGAAAGCAG GGACCCCGAT GCACAGAGTG GTAGGCTCCC AGCAGGGAAG GTGTATCCGG    720
AACGGAGAGC GATTCCAGGT GAAGATTGGG TACAATGAGG CGCTCATCGC AGTGTTTAAG    780
AGTCTGCCCA GCAGAAGTTA CGATCCTGCC ACCAAGACGT GGAACTTCAG CATGACTGAC    840
TATGGTCCCC TAATGAAAGC AGCCCAGCGC CTCCCAGGGA TCACCCTGCA GCCTTTGGAA    900
GGAGCCGAGG GCCACATGGA GTCACCCTCC ACCAGCAGTG GCATTATAGC CAAGACCGGC    960
CTTCCTGCAG CTCCCTCCCT GGCCTTTGTC AAAGGGCAGT GCGTGCTCAT CTCCCGGCC   1020
CGCTTCGAGG CAGACATCAG CTATTCAGAA GACCTGATTG CACTGTTTAA ACAGATGAT   1080
TCCAGAAAAT ATGATGTCAA GACCCGGAAG TGGAGCTTTC TCCTGGAAGA ATACAGTAA   1140
CTCATGGAAA GAGTGCGCGG CCCTCCACAA GTTCAGCTGG ATCCTCTGCC CAAGACCTC   1200
ACCCTYTTTC GCGCTCAGCT CCAGAAGACG TCTCTCTCTC CTGTGGCAGA CATCCCCAG   1260
GCAGACCTGT CCAGGGTGGA CTCCAAGCTT GTGTCTAGCT TGCTGCCCTT TCAGAGACT   1320
GGAGTCAATT TCGCTATAGC ACAAAGAGGC CGCCTGCTGC TTGCCGATGA CATGGGCTG   1380
GGGAAGACCA TCCAAGCCAT CTGCATAGCG GCCTATTACC GGAAGGAGTG GCCCCTCTG   1440
GTGGTGGTGC CGTCATCTGT GCGCTTCACC TGGGAGCAGG CCTTCTGTCG GTGGCTGCG   1500
TCTCTGAACC CATTAGACAT CAACGTCGTG GTAACCGGGA AGGACCGCCT GACAGATGC   1560
TTGGTCAACA TTGTCAGTTT TGATCTTCTG AGCAAGTTAG AAAAGCAGCT AAAACCCCA   1620
TTTAAAGTTG TCATCATTGA TGAATCCCAC TTCCTCAAAA ACATTAAGAC TGCCGTGGC   1680
GCAGCTATGC CCCTCCTCAA GGTTGCCAAG AGGGTGATCT TACTGTCAGG CACACCACA   1740
ATGTCCCGGC CGGCGGAGCT CTACACGCAG ATCCTGCCG TCAGGCCGAC CTTCTTCCT   1800
CAGTTCCATG CCTTTGGACT TCGCTACTGT GGCGCCAAGC GGCAGCCCTG GGATGGAC    1860
TACTCGGGCT CCTCCAACCT GGGGGAGCTG AAGCTCCTGC TAGAGGAGGC GGTCATGTG   1920
CGACGCCTCA AGGGTGATGT CCTCTCCCAG CTCCCAGCCA AGCAGCCAAG ATGGTGGGG   1980
TCGCCCCAGG CCAGATCAAT GCCAGGACCA GAGCCGCCCT GGATGCCGCC CGCCAAGAG   2040
ATGACCACCA AGGACAAAAC TAAGCAGCAG CAAAAAGAAG CCCTCATTCT CTTCTTCAC   2100
AGAACAGCTG AAGCTAAAAT TCCATCTATC ATCGAATATA TCCTGGACCT GCTAGAAGT   2160
GGACGAGAGA AGTTTCTTGT GTTTNCGCAC CATAAGGTGG TTCTGGATGC AATTACTAG   2220
GAGCTTGAGA GGAAGCGCGT GCAGCACATC CGTATCGATG GCTCCACCTC CTCGGCCAC   2280
```

```
CGCGAGACCT CTGCCAGCAG TTTCAGTTGT CCCCGGGCCC TGCGTGGCGT GCTGTCCTC    2340

ACCGCCGCCA ACATGGGCCT CACCTTCTCC TCGGCTGACC TGGTGGTGTT CGGGGAGTG    2400

TTTTGGAACC CGGGGGTGCT GATGCAGGCT GAGGACCGGG TGCACCGCAT CGGACAATG    2460

AGCTCCGTGA GCATCCACTA CCTGGTGGCG AGAGGCACGG CTGATGACTA CCTCTGGCC    2520

CTGATTCAAG AGAAGATTAA AGTTCTGGGT GAAGCCGGGC TCTCTGAGAC CAATTTTCA    2580

GAAATGACAG AAGCCACAGA TTACTTCTCC AAGGACTCAA AGCAGCAGAA GATCTACAC    2640

CTATTCCAGA AGTCCTTCGA GGAAGACGGA AATGATATGG AGCTCCTGGA GGCAGCAAG    2700

TCCTTTGATC CAGGTTCCCA GGACACGGGA GACAAGCTGG ATGAAAGCAC ATTGACGGC    2760

AGCCCAGTGA AGAAGAAGAG ATTTGAATTT TTTGATAACT GGGACAGCTT TACCTCTCT    2820

CTATAAGAGG AGGGGGAAAA AGCATTAAAA ATAATGGAAT TTATTACTCG TGCC         2874
```

(2) INFORMATION FOR SEQ ID NO: 55:

(i) SEQUENCE CHARACTERISTICS:
        (A) LENGTH: 941 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

```
Met Ser Ile Ser Pro Leu Lys Cys Pro Cys Leu Leu Gln Arg Ser Arg
 1               5                  10                  15

Gly Lys Lys Ile Glu Ala Asn Arg Gln Lys Ala Leu Ala Arg Arg Ala
            20                  25                  30

Glu Lys Leu Leu Ala Glu Gln His Gln Lys Pro Ala Gln Ser Lys Gln
        35                  40                  45

Gly Pro Ser Gln Asn Leu Pro Arg Asp Pro Ser Lys Ser Gly Ser His
    50                  55                  60

Gly Ile Phe Phe Lys Gln Gln Asn Pro Ser Ser Ser His Gly Asp
65                  70                  75                  80

Gln Arg Pro Gln Asn Pro His Ser Phe Pro Pro Asn Thr Ser Glu Gln
                85                  90                  95

Ala Lys Gly Met Trp Gln Arg Pro Glu Glu Met Pro Thr Ala Cys Pro
            100                 105                 110

Ser Tyr Arg Pro Pro Asn Gln Val Thr Val Ala Gly Ile Ser Leu Pro
        115                 120                 125

Leu Ala Asn Ser Pro Pro Gly Val Pro Ser Gln Gln Leu Trp Gly Cys
    130                 135                 140

Glu Leu Gly Gln Gly His Pro Gln Ala Ser Leu Glu Thr Gln Ser Thr
145                 150                 155                 160

Pro Phe Ala Asn Thr Thr His Glu Pro Leu Arg Lys Val Lys Asn Phe
                165                 170                 175

Gln Glu Thr Ala Ala Ser Ser Ser Gly Gln Pro Pro Arg Asp Pro Glu
            180                 185                 190

Leu Glu Ala Arg Ile Gly Arg Pro Ser Thr Ser Gly Gln Asn Ile Ser
        195                 200                 205

Gly Ser Val Met Pro Arg Thr Glu Gly Arg Leu Gln Gln Lys Ala Gly
    210                 215                 220

Thr Pro Met His Arg Val Val Gly Ser Gln Gln Gly Arg Cys Ile Arg
225                 230                 235                 240
```

-continued

```
Asn Gly Glu Arg Phe Gln Val Lys Ile Gly Tyr Asn Glu Ala Leu Ile
            245                 250                 255

Ala Val Phe Lys Ser Leu Pro Ser Arg Ser Tyr Asp Pro Ala Thr Lys
            260                 265                 270

Thr Trp Asn Phe Ser Met Thr Asp Tyr Gly Pro Leu Met Lys Ala Ala
            275                 280                 285

Gln Arg Leu Pro Gly Ile Thr Leu Gln Pro Leu Glu Gly Ala Glu Gly
            290                 295                 300

His Met Glu Ser Pro Ser Thr Ser Ser Gly Ile Ile Ala Lys Thr Gly
305                 310                 315                 320

Leu Pro Ala Ala Pro Ser Leu Ala Phe Val Lys Gly Gln Cys Val Leu
            325                 330                 335

Ile Ser Arg Ala Arg Phe Glu Ala Asp Ile Ser Tyr Ser Glu Asp Leu
            340                 345                 350

Ile Ala Leu Phe Lys Gln Met Asp Ser Arg Lys Tyr Asp Val Lys Thr
            355                 360                 365

Arg Lys Trp Ser Phe Leu Leu Glu Glu Tyr Ser Lys Leu Met Glu Arg
            370                 375                 380

Val Arg Gly Pro Pro Gln Val Gln Leu Asp Pro Leu Pro Lys Thr Leu
385                 390                 395                 400

Thr Leu Phe Arg Ala Gln Leu Gln Lys Thr Ser Leu Ser Pro Val Ala
            405                 410                 415

Asp Ile Pro Glu Ala Asp Leu Ser Arg Val Asp Ser Lys Leu Val Ser
            420                 425                 430

Ser Leu Leu Pro Phe Gln Arg Ala Gly Val Asn Phe Ala Ile Ala Gln
            435                 440                 445

Arg Gly Arg Leu Leu Ala Asp Asp Met Gly Leu Gly Lys Thr Ile
            450                 455                 460

Gln Ala Ile Cys Ile Ala Ala Tyr Tyr Arg Lys Glu Trp Pro Leu Leu
465                 470                 475                 480

Val Val Val Pro Ser Ser Val Arg Phe Thr Trp Glu Gln Ala Phe Cys
            485                 490                 495

Arg Trp Leu Pro Ser Leu Asn Pro Leu Asp Ile Asn Val Val Val Thr
            500                 505                 510

Gly Lys Asp Arg Leu Thr Asp Gly Leu Val Asn Ile Val Ser Phe Asp
            515                 520                 525

Leu Leu Ser Lys Leu Glu Lys Gln Leu Lys Pro Pro Phe Lys Val Val
            530                 535                 540

Ile Ile Asp Glu Ser His Phe Leu Lys Asn Ile Lys Thr Ala Val Cys
545                 550                 555                 560

Ala Ala Met Pro Leu Leu Lys Val Ala Lys Arg Val Ile Leu Leu Ser
            565                 570                 575

Gly Thr Pro Ala Met Ser Arg Pro Ala Glu Leu Tyr Thr Gln Ile Leu
            580                 585                 590

Ala Val Arg Pro Thr Phe Phe Pro Gln Phe His Ala Phe Gly Leu Arg
            595                 600                 605

Tyr Cys Gly Ala Lys Arg Gln Pro Trp Gly Trp Asp Tyr Ser Gly Ser
            610                 615                 620

Ser Asn Leu Gly Glu Leu Lys Leu Leu Leu Glu Glu Ala Val Met Leu
625                 630                 635                 640

Arg Arg Leu Lys Gly Asp Val Leu Ser Gln Leu Pro Ala Lys Gln Pro
            645                 650                 655

Arg Trp Trp Trp Ser Pro Gln Ala Arg Ser Met Pro Gly Pro Glu Pro
```

```
                    660                 665                 670
Pro Trp Met Pro Pro Ala Lys Glu Met Thr Thr Lys Asp Lys Thr Lys
            675                 680                 685
Gln Gln Gln Lys Glu Ala Leu Ile Leu Phe Phe Asn Arg Thr Ala Glu
    690                 695                 700
Ala Lys Ile Pro Ser Ile Ile Glu Tyr Ile Leu Asp Leu Leu Glu Ser
705                 710                 715                 720
Gly Arg Glu Lys Phe Leu Val Phe Xaa His His Lys Val Val Leu Asp
                725                 730                 735
Ala Ile Thr Lys Glu Leu Glu Arg Lys Arg Val Gln His Ile Arg Ile
            740                 745                 750
Asp Gly Ser Thr Ser Ser Ala Asp Arg Glu Thr Ser Ala Ser Ser Phe
        755                 760                 765
Ser Cys Pro Arg Ala Leu Arg Gly Val Leu Ser Ile Thr Ala Ala Asn
    770                 775                 780
Met Gly Leu Thr Phe Ser Ser Ala Asp Leu Val Val Phe Gly Glu Leu
785                 790                 795                 800
Phe Trp Asn Pro Gly Val Leu Met Gln Ala Glu Asp Arg Val His Arg
                805                 810                 815
Ile Gly Gln Leu Ser Ser Val Ser Ile His Tyr Leu Val Ala Arg Gly
            820                 825                 830
Thr Ala Asp Asp Tyr Leu Trp Pro Leu Ile Gln Glu Lys Ile Lys Val
        835                 840                 845
Leu Gly Glu Ala Gly Leu Ser Glu Thr Asn Phe Ser Glu Met Thr Glu
    850                 855                 860
Ala Thr Asp Tyr Phe Ser Lys Asp Ser Lys Gln Gln Lys Ile Tyr Asn
865                 870                 875                 880
Leu Phe Gln Lys Ser Phe Glu Glu Asp Gly Asn Asp Met Glu Leu Leu
                885                 890                 895
Glu Ala Ala Glu Ser Phe Asp Pro Gly Ser Gln Asp Thr Gly Asp Lys
            900                 905                 910
Leu Asp Glu Ser Thr Leu Thr Gly Ser Pro Val Lys Lys Lys Arg Phe
        915                 920                 925
Glu Phe Phe Asp Asn Trp Asp Ser Phe Thr Ser Pro Leu
    930                 935                 940
```

(2) INFORMATION FOR SEQ ID NO: 56:

(i) SEQUENCE CHARACTERISTICS:
        (A) LENGTH: 727 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

```
Thr Glu Gly Arg Leu Gln Gln Lys Ala Gly Thr Pro Met His Arg Val
1               5                   10                  15
Val Gly Ser Gln Gln Gly Arg Cys Ile Arg Asn Gly Glu Arg Phe Gln
            20                  25                  30
Val Lys Ile Gly Tyr Asn Glu Ala Leu Ile Ala Val Phe Lys Ser Leu
        35                  40                  45
Pro Ser Arg Ser Tyr Asp Pro Ala Thr Lys Thr Trp Asn Phe Ser Met
    50                  55                  60
Thr Asp Tyr Gly Pro Leu Met Lys Ala Ala Gln Arg Leu Pro Gly Ile
```

-continued

```
65                  70                  75                  80
Thr Leu Gln Pro Leu Glu Gly Ala Glu Gly His Met Glu Ser Pro Ser
                85                  90                  95
Thr Ser Ser Gly Ile Ile Ala Lys Thr Gly Leu Pro Ala Ala Pro Ser
            100                 105                 110
Leu Ala Phe Val Lys Gly Gln Cys Val Leu Ile Ser Arg Ala Arg Phe
        115                 120                 125
Glu Ala Asp Ile Ser Tyr Ser Glu Asp Leu Ile Ala Leu Phe Lys Gln
    130                 135                 140
Met Asp Ser Arg Lys Tyr Asp Val Lys Thr Arg Lys Trp Ser Phe Leu
145                 150                 155                 160
Leu Glu Glu Tyr Ser Lys Leu Met Glu Arg Val Arg Gly Pro Pro Gln
                165                 170                 175
Val Gln Leu Asp Pro Leu Pro Lys Thr Leu Thr Leu Phe Arg Ala Gln
            180                 185                 190
Leu Gln Lys Thr Ser Leu Ser Pro Val Ala Asp Ile Pro Glu Ala Asp
        195                 200                 205
Leu Ser Arg Val Asp Ser Lys Leu Val Ser Ser Leu Pro Phe Gln
    210                 215                 220
Arg Ala Gly Val Asn Phe Ala Ile Ala Gln Arg Gly Arg Leu Leu
225                 230                 235                 240
Ala Asp Asp Met Gly Leu Gly Lys Thr Ile Gln Ala Ile Cys Ile Ala
                245                 250                 255
Ala Tyr Tyr Arg Lys Glu Trp Pro Leu Leu Val Val Pro Ser Ser
            260                 265                 270
Val Arg Phe Thr Trp Glu Gln Ala Phe Cys Arg Trp Leu Pro Ser Leu
        275                 280                 285
Asn Pro Leu Asp Ile Asn Val Val Thr Gly Lys Asp Arg Leu Thr
    290                 295                 300
Asp Gly Leu Val Asn Ile Val Ser Phe Asp Leu Leu Ser Lys Leu Glu
305                 310                 315                 320
Lys Gln Leu Lys Pro Pro Phe Lys Val Val Ile Asp Glu Ser His
                325                 330                 335
Phe Leu Lys Asn Ile Lys Thr Ala Val Cys Ala Ala Met Pro Leu Leu
            340                 345                 350
Lys Val Ala Lys Arg Val Ile Leu Leu Ser Gly Thr Pro Ala Met Ser
        355                 360                 365
Arg Pro Ala Glu Leu Tyr Thr Gln Ile Leu Ala Val Arg Pro Thr Phe
    370                 375                 380
Phe Pro Gln Phe His Ala Phe Gly Leu Arg Tyr Cys Gly Ala Lys Arg
385                 390                 395                 400
Gln Pro Trp Gly Trp Asp Tyr Ser Gly Ser Asn Leu Gly Glu Leu
                405                 410                 415
Lys Leu Leu Leu Glu Glu Ala Val Met Leu Arg Arg Leu Lys Gly Asp
            420                 425                 430
Val Leu Ser Gln Leu Pro Ala Lys Gln Pro Arg Trp Trp Ser Pro
        435                 440                 445
Gln Ala Arg Ser Met Pro Gly Pro Glu Pro Pro Trp Met Pro Ala
    450                 455                 460
Lys Glu Met Thr Thr Lys Asp Lys Thr Lys Gln Gln Lys Glu Ala
465                 470                 475                 480
Leu Ile Leu Phe Phe Asn Arg Thr Ala Glu Ala Lys Ile Pro Ser Ile
                485                 490                 495
```

-continued

```
Ile Glu Tyr Ile Leu Asp Leu Leu Glu Ser Gly Arg Glu Lys Phe Leu
                500                 505                 510

Val Phe Xaa His His Lys Val Val Leu Asp Ala Ile Thr Lys Glu Leu
                515                 520                 525

Glu Arg Lys Arg Val Gln His Ile Arg Ile Asp Gly Ser Thr Ser Ser
            530                 535                 540

Ala Asp Arg Glu Thr Ser Ala Ser Ser Phe Ser Cys Pro Arg Ala Leu
545                 550                 555                 560

Arg Gly Val Leu Ser Ile Thr Ala Ala Asn Met Gly Leu Thr Phe Ser
                565                 570                 575

Ser Ala Asp Leu Val Val Phe Gly Glu Leu Phe Trp Asn Pro Gly Val
                580                 585                 590

Leu Met Gln Ala Glu Asp Arg Val His Arg Ile Gly Gln Leu Ser Ser
            595                 600                 605

Val Ser Ile His Tyr Leu Val Ala Arg Gly Thr Ala Asp Asp Tyr Leu
            610                 615                 620

Trp Pro Leu Ile Gln Glu Lys Ile Lys Val Leu Gly Glu Ala Gly Leu
625                 630                 635                 640

Ser Glu Thr Asn Phe Ser Glu Met Thr Glu Ala Thr Asp Tyr Phe Ser
                645                 650                 655

Lys Asp Ser Lys Gln Gln Lys Ile Tyr Asn Leu Phe Gln Lys Ser Phe
                660                 665                 670

Glu Glu Asp Gly Asn Asp Met Glu Leu Leu Glu Ala Ala Glu Ser Phe
            675                 680                 685

Asp Pro Gly Ser Gln Asp Thr Gly Asp Lys Leu Asp Glu Ser Thr Leu
            690                 695                 700

Thr Gly Ser Pro Val Lys Lys Arg Phe Glu Phe Asp Asn Trp
705                 710                 715                 720

Asp Ser Phe Thr Ser Pro Leu
                725
```

(2) INFORMATION FOR SEQ ID NO: 57:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 57:

```
GAGCTGTACA CCCAGATCCT CGCCGTCAGG CCGACCTTCT TCCCTCAGTT CCATGCCTT      60
```

(2) INFORMATION FOR SEQ ID NO: 58:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

```
Glu Leu Tyr Thr Gln Ile Leu Ala Val Arg Pro Thr Phe Phe Pro Gln
1               5                   10                  15

Phe His Ala Phe
            20
```

(2) INFORMATION FOR SEQ ID NO: 59:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 59:

```
CATGGGCCTG GGGAAGACCA TCCAAGCCAT CTGCATAGCG GCCTATTACC GGAAGGAGTG      60

GCCCCTCCTG GTGGTGGTGC CGTCATCTGT GCGCTTCACC TGGGAGCAGG CCTTCTGTCG     120

GTGGCTGCCG TCTCTGAACC CATTAGACAT CAACGTCGTG GTAACCGGGA AGGACCGCCT     180

GACAGATGGC TTGGTCAACA TTGTCAGTTT TGATCTTCTG AGCAAGTTAG AAAAGCAGCT     240

AAAACCCCCA TTTAAAGTTG TCATCATTGA TGAATCCCAC TTCCTCAAAA ACATTAAGAC     300

TGCCGTGTGC GCAGCTATGC CCCTCCTCAA GGTTGCCAAG AGGGTGATCT TACTGTCAGG     360

CACACCAGCA ATGTCCCGGC CGGCGGAGCT CTACACGCAG ATCCTCGCCG TCAGGCCGAC     420

CTTCTTCCCT                                                           430
```

(2) INFORMATION FOR SEQ ID NO: 60:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

```
Met Gly Leu Gly Lys Thr Ile Gln Ala Ile Cys Ile Ala Ala Tyr Tyr
 1               5                  10                  15

Arg Lys Glu Trp Pro Leu Leu Val Val Val Pro Ser Ser Val Arg Phe
            20                  25                  30

Thr Trp Glu Gln Ala Phe Cys Arg Trp Leu Pro Ser Leu Asn Pro Leu
        35                  40                  45

Asp Ile Asn Val Val Val Thr Gly Lys Asp Arg Leu Thr Asp Gly Leu
    50                  55                  60

Val Asn Ile Val Ser Phe Asp Leu Leu Ser Lys Leu Glu Lys Gln Leu
65                  70                  75                  80

Lys Pro Pro Phe Lys Val Val Ile Ile Asp Glu Ser His Phe Leu Lys
                85                  90                  95

Asn Ile Lys Thr Ala Val Cys Ala Ala Met Pro Leu Leu Lys Val Ala
            100                 105                 110

Lys Arg Val Ile Leu Leu Ser Gly Thr Pro Ala Met Ser Arg Pro Ala
        115                 120                 125

Glu Leu Tyr Thr Gln Ile Leu Ala Val Arg Pro Thr
    130                 135                 140
```

(2) INFORMATION FOR SEQ ID NO: 61:

(i) SEQUENCE CHARACTERISTICS:
        (A) LENGTH: 3059 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO: 61:

| | | | | | |
|---|---|---|---|---|---|
| GTATGTTTAA | TTTTAAAAGA | AATTTTAATA | TATCCTTTGT | TTATACTCCT | TGTGCATTTC | 60 |
| CTGGGACAAA | AGCTTGTTGA | AATCAAGGTA | AGCAAAAAAA | AATTTTTTTA | ATTAATGTCT | 120 |
| ATTTCCATGT | TGTTTTTCCT | TTCTCAGCTT | TTGCCAAGTT | TCCGATTACA | GACTGACATT | 180 |
| CCTGCATGAG | CATCTCCCCA | TTAAAATGTC | CTTGCCTCTT | ACAGAGGAGC | AGAGGAAAAA | 240 |
| AAATTGAAGC | AAATCGGCAG | AAGGCTCTGG | CCCGAAGAGC | TGAGAAACTA | TTAGCAGAAC | 300 |
| AGCATCAGAA | ACCTGCCCAG | TCCAAGCAGG | GCCCATCCCA | AAACCTCCCC | CGAGATCCTT | 360 |
| CTAAGTCAGG | GAGCCATGGC | ATCTTTTTCA | ACAACAAAA | TCCCAGCAGT | TCATCTCATG | 420 |
| GTGACCAGAG | ACCTCAAAAT | CCCCACAGTT | TTCCACCCAA | CACCTCTGAG | CAGGCGAAGG | 480 |
| GGATGTGGCA | GAGGCCAGAA | GAGATGCCCA | CAGCCTGCCC | AAGCTACCGC | CCACCAAATC | 540 |
| AAGTGACTGT | CGCTGGGATC | TCCCTGCCCC | TGGCAAACAG | TCCTCCAGGG | GTCCCCAGCC | 600 |
| AACAGCTTTG | GGGTTGTGAG | TTAGGTCAAG | GTCATCCTCA | GGCTTCACTC | GAGACCCAGT | 660 |
| CAACACCCTT | CACTAACACA | ACTCACGAGC | CTTTGCGCAA | AGTGAAGAAT | TTCCAGGAGA | 720 |
| CAGCAGCCTC | TTCCTGTGGA | CAGCCTCCTA | GGGATCCTGA | ATTAGAGGCC | AGGATCGGAA | 780 |
| GACCTTCCAC | CTCTGGGCAG | AACATTTCGG | GGAGTGTGAT | GCCCAGGACA | GAAGGAAGAC | 840 |
| TGCAACAGAA | AGCAGGGACC | CCGCTGCACA | GAGTGGTAGG | CTCCCAGCAG | GGAAGGTGTA | 900 |
| TCCGGAACGG | AGAGCGATTC | CAGGTGAAGA | TTGGGTACAA | TGAGGCGCTC | ATCGCAGTGT | 960 |
| TTAAGAGTCT | GCCCAGCAGA | AGTTACGATC | CTGCCACCAA | GACGTGGAAC | TTCAGCATGA | 1020 |
| CTGACTATGG | TCCCCTAATG | AAAGCAGCCC | AGCGCCTCCC | AGGGATCACC | CTGCAGCCTT | 1080 |
| TGGAAGGAGC | CGAGGGCCAC | ATGGAGTCAC | CCTCCACCAG | CAGTGGCATT | ATAGCCAAGA | 1140 |
| CCGGCCTTCC | TGCAGCTCCC | TCCCTGGCCT | TTGTCAAAGG | GCAGTGCGTG | CTCATCTCCC | 1200 |
| GGGCCCGCTT | CGAGGCAGAC | ATCAGCTATT | CAGAAGACCT | GATTGCACTG | TTTAAACAGA | 1260 |
| TGGATTCCAG | AAAATATGAT | GTCAAGACCC | GGAAGTGGAG | CTTTCTCCTG | GAAGAATACA | 1320 |
| GTAAACTCAT | GGAAAGAGTG | CGCGGCCCTC | CACAAGTTCA | GCTGGATCCT | CTGCCCAAGA | 1380 |
| CCCTCACCCT | YTTTCGCGCT | CAGCTCCAGA | AGACGTCTCT | CTCTCCTGTG | GCAGACATCC | 1440 |
| CCGAGGCAGA | CCTGTCCAGG | GTGGACTCCA | AGCTTGTGTC | TAGCTTGCTG | CCCTTTCAGA | 1500 |
| GAGCTGGAGT | CAATTTCGCT | ATAGCACAAA | GAGGCCGCCT | GCTGCTTGCC | GATGACATGG | 1560 |
| GCCTGGGGAA | GACCATCCAA | GCCATCTGCA | TAGCGGCCTA | TTACCGGAAG | GAGTGGCCCC | 1620 |
| TCCTGGTGGT | GGTGCCGTCA | TCTGTGCGCT | TCACCTGGGA | GCAGGCCTTC | TGTCGGTGGC | 1680 |
| TGCCGTCTCT | GAACCCATTA | GACATCAACG | TCGTGGTAAC | CGGGAAGGAC | CGCCTGACAG | 1740 |
| ATGGCTTGGT | CAACATTGTC | AGTTTTGATC | TTCTGAGCAA | GTTAGAAAAG | CAGCTAAAAC | 1800 |
| CCCCATTTAA | AGTTGTCATC | ATTGATGAAT | CCCACTTCCT | CAAAAACATT | AAGACTGCCG | 1860 |
| TGTGCGCAGC | TATGCCCCTC | CTCAAGGTTG | CCAAGAGGGT | GATCTTACTG | TCAGGCACAC | 1920 |
| CAGCAATGTC | CCGGCCGGCG | GAGCTCTACA | CGCAGATCCT | CGCCGTCAGG | CCGACCTTCT | 1980 |
| TCCCTCAGTT | CCATGCCTTT | GGACTTCGCT | ACTGTGGCGC | CAAGCGGCAG | CCCTGGGGAT | 2040 |
| GGGACTACTC | GGGCTCCTCC | AACCTGGGGG | AGCTGAAGCT | CCTGCTAGAG | GAGGCGGTCA | 2100 |
| TGCTGCGACG | CCTCAAGGGT | GATGTCCTCT | CCCAGCTCCC | AGCCAAGCAG | CCAAGATGGT | 2160 |
| GGTGGTCGCC | CCAGGCCAGA | TCAATGCCAG | GACCAGAGCC | GCCCTGGATG | CCGCCCGCCA | 2220 |
| AGGAGATGAC | CACCAAGGAC | AAAACTAAGC | AGCAGCAAAA | AGAAGCCCTC | ATTCTCTTCT | 2280 |

```
TCAACAGAAC AGCTGAAGCT AAAATTCCAT CTATCATCGA ATATATCCTG GACCTGCTAG    2340

AAAGTGGACG AGAGAAGTTT CTTGTGTTTG CGCACCATAA GGTGGTTCTG GATGCAATTA    2400

CTAAGGAGCT TGAGAGGAAG CGCGTGCAGC ACATCCGTAT CGATGGCTCC ACCTCCTCGG    2460

CCGACCGCGA GACCTCTGCC AGCAGTTTCA GTTGTCCCCG GGCCCTGCGT GGCGTGCTGT    2520

CCATCACCGC CGCCAACATG GGCCTCACCT TCTCCTCGGC TGACCTGGTG GTGTTCGGGG    2580

AGCTGTTTTG GAACCCGGGG GTGCTGATGC AGGCTGAGGA CCGGGTGCAC CGCATCGGAC    2640

AATTGAGCTC CGTGAGCATC CACTACCTGG TGGCGAGAGG CACGGCTGAT GACTACCTCT    2700

GGCCCCTGAT TCAAGAGAAG ATTAAAGTTC TGGGTGAAGC CGGGCTCTCT GAGACCAATT    2760

TTTCAGAAAT GACAGAAGCC ACAGATTACT TCTCCAAGGA CTCAAAGCAG CAGAAGATCT    2820

ACAACCTATT CCAGAAGTCC TTCGAGGAAG ACGGAAATGA TATGGAGCTC CTGGAGGCAG    2880

CAGAGTCCTT TGATCCAGGT TCCCAGGACA CGGGAGACAG GCTGGATGAA AGCACATTGA    2940

CGGGCAGCCC AGTGAAGAAG AAGAGATTTG AATTTTTTGA TAACTGGGAC AGCTTTACCT    3000

CTCCTCTATA AGAGGAGGGG GAAAAAGCAT TAAAAATAAT GGAATTTATT ACTCGTGCC    3059

(2) INFORMATION FOR SEQ ID NO: 62:

(i) SEQUENCE CHARACTERISTICS:
        (A) LENGTH: 936 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO: 62:

CCCCCCCCCA CCCCCCCCCC CCCCCCCCCC CCCCCCCCCT CCCCCCCTCC CCCCCCCCCC      60

CCCCCCGGCC TTTTTCCCCC CCCCCCCGCC CTTTTTCCCC TCCCTTCCAC CCCCCCGACT     120

TCCCCCCCCC GCCCCCCACC CGCACCCCCG GGGCCGGACC ACTCGGGTTC TCCCAACCCG     180

GGGACCCGAA CTTCCCGCCA GCGGCGCGCT CACCCCCGAA CCCTTCAAGG CGACTTCTTT     240

TTCCCAGTTC CCACCCAAGA GCCAAGATGG TGGTGGTTCC CCCAGCCCAG ATCAATGCCA     300

GGACCAGACC CCCCCTGGAT CCCCCCGCCC AAGGAGATGA CCACCAAGGA CAAAACTAAG     360

CAGCAGCAAA AGAAGCCTT CATTTTCTTC TTTCAACAGA ACAGCTGAAG CTAAAATTCC     420

ATCTATCATC GAATATATCC TGGACCTGCT AGAAAGTGGA CGAGAGAAGT TTCTTGTGTT     480

TGCGCACCAT AAGGTGGTTC TGGATGCAAT TACTAAGGAG CTTGAGAGGA AGCGCGTGCA     540

GCACATCCGT ATCGATGGCT CCACCTCCTC GGCCGACCGC GAGGACCTCT GCCAGCAGTT     600

TCAGTTGTCC CCGGGCCCTG CCGTGGCCGT GCTGTCCATC ACCGCCGCCA ACATGGGCCT     660

CATCTTCTCC TCGGCTGACC TGGTGGTGTT CGGGGAGCTG TTTTGGAACC CGGGGGTGCT     720

GATGCAGGCT GAGGACCGGG TGCACCGCAT CGGACAGTTG AGCTCCGTGA GCATCCACCA     780

CCTGGTGGCG AGAGGCACGG CTGATGACTA CCTCTGGCCC CTGATTCAAG AGAAGATTAA     840

AGTTCTGGGT GAAGCCGGGC CCCCTGAGAC CAATTTTTCA GAAATGACAG AAGCCACAAA     900

TTATTCTCCA AGGATCAAAG CAGCAGAAGA TCTAAA                               936

(2) INFORMATION FOR SEQ ID NO: 63:

(i) SEQUENCE CHARACTERISTICS:
        (A) LENGTH: 955 base pairs
        (B) TYPE: nucleic acid
        (C) STRANDEDNESS: single
```

(D) TOPOLOGY: linear (ii) MOLECULE TYPE: Other (xi) SEQUENCE DESCRIPTION: SEQ ID NO: 63:

| | | | | | |
|---|---|---|---|---|---|
| CCCGGCCGGC | GGAGCTCTAC | ACGCAGATCC | TCGCCGTCAG | GCCGACCTTC | TTCCCTCAGT | 60 |
| TCCATGCCTT | TGGACTTCGC | TACTGTGGCG | CCAAGCGGCA | GCCCTGGGGA | TGGGACTACT | 120 |
| CGGGCTCCTC | CAACCTGGGG | GAGCTGAAGC | TCCTGCTAGA | GGAGGCGGTC | ATGCTGCGAC | 180 |
| GCCTCAAGGG | TGATGTCCTC | TCCCAGCTCC | CAGCCAAGCA | GCCAAGATGG | TGGTGGTCGC | 240 |
| CCCAGGCCAG | ATCAATGCCA | GGACCAGAGC | CGCCCTGGAT | GCCGCCCGCC | AAGGAGATGA | 300 |
| CCACCAAGGA | CAAAACTAAG | CAGCAGCAAA | AGAAGCCCT | CATTCTCTTC | TTCAACAGAA | 360 |
| CAGCTGAAGC | TAAAATTCCA | TCTATCATCG | AATATATCCT | GGACCTGCTA | GAAAGTGGAC | 420 |
| GAGAGAAGTT | TCTTGTGTTT | NCGCACCATA | AGGTGGTTCT | GGATGCAATT | ACTAAGGAGC | 480 |
| TTGAGAGGAA | GCGCGTGCAG | CACATCCGTA | TCGATGGCTC | CACCTCCTCG | GCCGACCGCG | 540 |
| AGACCTCTGC | CAGCAGTTTC | AGTTGTCCCC | GGGCCCTGCG | TGGCGTGCTG | TCCATCACCG | 600 |
| CCGCCAACAT | GGGCCTCACC | TTCTCCTCGG | CTGACCTGGT | GGTGTTCGGG | GAGCTGTTTT | 660 |
| GGAACCCGGG | GGTGCTGATG | CAGGCTGAGG | ACCGGGTGCA | CCGCATCGGA | CAATTGAGCT | 720 |
| CCGTGAGCAT | CCACTACCTG | GTGGCGAGAG | GCACGGCTGA | TGACTACCTC | TGGCCCCTGA | 780 |
| TTCAAGAGAA | GATTAAAGTT | CTGGGTGAAG | CCGGGCTCTC | TGAGACCAAT | TTTTCAGAAA | 840 |
| TGACAGAAGC | CACAGATTAC | TTCTCCAAGG | ACTCAAAGCA | GCAGAAGATC | TACAACCTAT | 900 |
| TCCAGAAGTC | CTTCGAGGAA | GACGGAAATG | ATATGGAGCT | CCTGGAGGCA | GCAGA | 955 |

(2) INFORMATION FOR SEQ ID NO: 64:

(i) SEQUENCE CHARACTERISTICS:
        (A) LENGTH: 892 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 64:

| | | | | | |
|---|---|---|---|---|---|
| CCCTCCCCCC | CCCCCCCCCC | CCGGCCTTTT | TCCCCCCCCC | CCCGCCCTTT | TTCCCCTCCC | 60 |
| TTCCACCCCC | CCGACTTCCC | CCCCCCGCCC | CCCACCCGCA | CCCCCGGGGC | CGGACCACTC | 120 |
| GGGTTCTCCC | AACCCGGGGA | CCCGAACTTC | CCGCCAGCGG | CGCGCTCACC | CCCGAACCCT | 180 |
| TCAAGGCGAC | TTCTTTTTCC | CAGTTCCCAC | CCAAGAGCCA | AGATGGTGGT | GGTTCCCCCA | 240 |
| GCCCAGATCA | ATGCCAGGAC | CAGACCCCCC | CTGGATCCCC | CCGCCCAAGG | AGATGACCAC | 300 |
| CAAGGACAAA | ACTAAGCAGC | AGCAAAAAGA | AGCCTTCATT | TTCTTCTTTC | AACAGAACAG | 360 |
| CTGAAGCTAA | AATTCCATCT | ATCATCGAAT | ATATCCTGGA | CCTGCTAGAA | AGTGGACGAG | 420 |
| AGAAGTTTCT | TGTGTTTGCG | CACCATAAGG | TGGTTCTGGA | TGCAATTACT | AAGGAGCTTG | 480 |
| AGAGGAAGCG | CGTGCAGCAC | ATCCGTATCG | ATGGCTCCAC | CTCCTCGGCC | GACCGCGAGG | 540 |
| ACCTCTGCCA | GCAGTTTCAG | TTGTCCCCGG | GCCCTGCCGT | GGCCGTGCTG | TCCATCACCG | 600 |
| CCGCCAACAT | GGGCCTCATC | TTCTCCTCGG | CTGACCTGGT | GGTGTTCGGG | GAGCTGTTTT | 660 |
| GGAACCCGGG | GGTGCTGATG | CAGGCTGAGG | ACCGGGTGCA | CCGCATCGGA | CAGTTGAGCT | 720 |
| CCGTGAGCAT | CCACCACCTG | GTGGCGAGAG | GCACGGCTGA | TGACTACCTC | TGGCCCCTGA | 780 |
| TTCAAGAGAA | GATTAAAGTT | CTGGGTGAAG | CCGGGCCCCC | TGAGACCAAT | TTTTCAGAAA | 840 |

TGACAGAAGC CACAAATTAT TCTCCAAGGA TCAAAGCAGC AGAAGATCTA AA        892

(2) INFORMATION FOR SEQ ID NO: 65:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

```
Leu Lys Val Ala Lys Arg Val Ile Leu Leu Ser Gly Thr Pro Ala Met
  1               5                  10                  15

Ser Arg Pro Ala Glu Leu Tyr Thr Gln Ile Leu Ala Val Arg Pro Thr
             20                  25                  30

Phe Phe Pro Gln Phe His Ala Phe Gly Leu Arg Tyr Cys Gly Ala Lys
         35                  40                  45

Arg Gln Pro Trp Gly Trp Asp Tyr Ser Gly Ser Ser Asn Leu Gly Glu
     50                  55                  60

Leu Lys Leu Leu Leu Glu Glu Ala Val Met Leu Arg Arg Leu Lys Gly
 65                  70                  75                  80

Asp Val Leu Ser Gln Leu Pro Ala Lys Gln Pro Arg Trp Trp Trp Ser
                 85                  90                  95

Pro Gln Ala Arg Ser Met Pro Gly Pro Glu Pro Pro Trp Met Pro Pro
                100                 105                 110

Ala Lys Glu Met Thr Thr Lys Asp Lys Thr Lys Gln Gln Gln Lys Glu
            115                 120                 125

Ala Leu Ile Leu Phe Phe Asn Arg Thr Ala Glu Ala Lys Ile Pro Ser
        130                 135                 140

Ile Ile Glu Tyr Ile Leu Asp Leu Leu Glu Ser Gly Arg Glu Lys Phe
145                 150                 155                 160

Leu Val Phe Xaa His His Lys Val Val Leu Asp Ala Ile Thr Lys Glu
                165                 170                 175

Leu Glu Arg Lys Arg Val Gln His Ile Arg Ile Asp Gly Ser Thr Ser
            180                 185                 190

Ser Ala Asp Arg Glu Thr Ser Ala Ser Ser Phe Ser Cys Pro Arg Ala
        195                 200                 205

Leu Arg Gly Val Leu Ser Ile Thr Ala Ala Asn Met Gly Leu Thr Phe
    210                 215                 220

Ser Ser Ala Asp Leu Val Val Phe Gly Glu Leu Phe Trp Asn Pro Gly
225                 230                 235                 240

Val Leu Met Gln Ala Glu Asp Arg Val His Arg Ile Gly Gln Leu Ser
                245                 250                 255

Ser Val Ser Ile His Tyr Leu Val Ala Arg Gly Thr Ala Asp Asp Tyr
            260                 265                 270

Leu Trp Pro Leu Ile Gln Glu Lys Ile Lys Val Leu Gly Glu Ala Gly
        275                 280                 285

Leu Ser Glu Thr Asn Phe Ser Glu Met Thr Glu Ala Thr Asp Tyr Phe
    290                 295                 300

Ser Lys Asp Ser Lys Gln Gln Lys Ile Tyr Asn Leu Phe Gln Lys Ser
305                 310                 315                 320

Phe Glu Glu Asp Gly Asn Asp Met Glu Leu Leu Glu Ala Ala Glu Ser
                325                 330                 335

Phe Asp Pro Gly Ser Gln Asp Thr Gly Asp Lys Leu Asp Glu Ser Thr
```

Leu Thr Gly Ser Pro Val Lys
        355

(2) INFORMATION FOR SEQ ID NO: 66:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

Pro Pro Pro Pro Pro Pro Pro Pro Pro Pro Pro Pro Pro Pro Pro Leu
1               5                   10                  15

Pro Pro Pro Pro Pro Ala Phe Phe Pro Pro Pro Pro Pro Phe Phe
            20                  25                  30

Pro Ser Leu Pro Pro Pro Arg Leu Pro Pro Pro Ala Pro His Pro His
            35                  40                  45

Pro Arg Gly Arg Thr Thr Arg Val Leu Pro Thr Arg Gly Pro Glu Leu
50                  55                  60

Pro Ala Ser Gly Ala Leu Thr Pro Glu Pro Phe Lys Ala Thr Ser Phe
65                  70                  75                  80

Ser Gln Phe Pro Pro Lys Ser Gln Asp Gly Gly Ser Pro Ser Pro
                85                  90                  95

Asp Gln Cys Gln Asp Gln Thr Pro Pro Gly Ser Pro Arg Pro Arg Arg
                100                 105                 110

Xaa Pro Pro Arg Thr Lys Leu Ser Ser Ser Lys Lys Lys Pro Ser Phe
            115                 120                 125

Ser Ser Phe Asn Arg Thr Ala Glu Ala Lys Ile Pro Ser Ile Ile Glu
    130                 135                 140

Tyr Ile Leu Asp Leu Leu Glu Ser Gly Arg Glu Lys Phe Leu Val Phe
145                 150                 155                 160

Ala His His Lys Val Val Leu Asp Ala Ile Thr Lys Glu Leu Glu Arg
                165                 170                 175

Lys Arg Val Gln His Ile Arg Ile Asp Gly Ser Thr Ser Ser Ala Asp
                180                 185                 190

Arg Glu Asp Leu Cys Gln Gln Phe Gln Leu Ser Pro Gly Pro Ala Val
    195                 200                 205

Ala Val Leu Ser Ile Thr Ala Ala Asn Met Gly Leu Ile Phe Ser Ser
210                 215                 220

Ala Asp Leu Val Val Phe Gly Glu Leu Phe Trp Asn Pro Gly Val Leu
225                 230                 235                 240

Met Gln Ala Glu Asp Arg Val His Arg Ile Gly Gln Leu Ser Ser Val
                245                 250                 255

Ser Ile His His Leu Val Ala Arg Gly Thr Ala Asp Asp Tyr Leu Trp
                260                 265                 270

Pro Leu Ile Gln Glu Lys Ile Lys Val Leu Gly Glu Ala Gly Pro Pro
            275                 280                 285

Glu Thr Asn Phe Ser Glu Met Thr Glu Ala Thr Asn Tyr Ser Pro Arg
    290                 295                 300

Ile Lys Ala Ala Glu Asp Leu
305                 310

METHODS AND COMPOSITIONS FOR TARGETING DNA METABOLIC PROCESSES USING AMINOGLYCOSIDE DERIVATIVES

This is a divisional application Ser. No. 09/179,558, filed Oct. 27, 1998 now U.S. Pat. No. 6,180,612, which is a continuation-in-part of application Ser. No. 09/060,470 filed on Apr. 15, 1998, now abandoned, which claims the benefit under 35 U.S.C. §119(e) of provisional Application No. 60/063,898 filed Oct. 31, 1997, each of which is hereby incorporated by reference in its entirety.

This invention was partially made with government support under grant number R29GM43569 awarded by the National Institutes of Health. The government has certain rights in the invention.

1. INTRODUCTION

The invention provides protein targets for disease intervention through inhibition of nucleic acid metabolism. Novel polypeptides for one such target, DNA-dependent ATPase A, and novel polynucleotides encoding DNA-dependent ATPase A are disclosed. The invention also provides compounds, including phosphoaminoglycosides, which act on such protein targets to inhibit nucleic acid metabolism. In addition, the invention provides screening assays for identifying compounds that inhibit nucleic acid-dependent ATPase activity, including, but not limited to, DNA-dependent ATPase A. Such compounds are useful in the treatment of diseases, including but not limited to cancer and infectious disease, through disruption of nucleic acid metabolism and induction of apoptosis. Moreover, the invention provides methods for prevention and treatment of diseases including, but not limited to cancer and infectious disease.

2. BACKGROUND OF THE INVENTION

The interactions of proteins with nucleic acids involve a host of mechanisms for nucleic acid binding. Many nucleic acid-binding proteins (transcriptional repressors, transcriptional activators, restriction endonucleases, etc.) interact with a primary recognition sequence in a polynucleotide. These proteins: i) are generally classified as "sequence specific binding proteins"; ii) tend to bind double-stranded nucleic acids; and iii) tend to have significant numbers of contacts between their amino acid side chains and the edges of the bases which are exposed in either the minor or the major groove of a double-stranded nucleic acid. Proteins in this class have been the subject of extensive biochemical characterization and a significant number of protein-DNA co-crystal structures are now available (Steitz. *Q. Rev. Biophys.* 23, 205–280 (1990); Pabo and Sauer. *Annu. Rev. Biochem.* 61, 1053–1059 (1992)).

A second class of proteins, "nonspecific binding proteins" (single-stranded DNA binding protein, DNA polymerases, etc.) are generally found to interact with single-stranded nucleic acids. The non-specific proteins are commonly considered to bind to a nucleic acid through predominately electrostatic interactions with the phosphodiester backbone of the nucleic acid and the favorable binding can be enhanced through protein-protein interactions (cooperativity). Biochemical analysis has been extensive for many of these proteins but unlike the sequence specific binding proteins, the information about protein-DNA contacts from crystallographic structures is very limited (Lohman and Ferrari. *Annu. Rev. Biochem.* 63, 527–570 (1994)).

Finally, there are a number of proteins that are not readily classified according to the specific or nonspecific categories. This third group of proteins is not generally grouped as a class but have the common feature of recognizing and binding to specific nucleic acid structures with neither the sequence specificity nor the electrostatic interactions of either group of proteins described above. This latter group would include proteins such as: i) *E. coli* RuvA and RuvB, which bind Holliday junctions and promote branch migration (Parsons et al., *Proc. Natl. Acad. Sci. U.S.A.* 89, 5452–5456 (1992); Muller et al., *J. Biol. Chem.* 268, 17185–17189 (1993)); ii) *E. coli* ribosomal protein L11, which recognizes the three-dimensional conformation of an RNA backbone and thus may regulate conformational changes during the ribosome elongation cycle (Ryan et al., *J. Mol. Biol.* 221, 1257–1268 (1991); Ryan and Draper. *Biochemistry.* 28, 9949–9956 (1989)); iii) topoisomerase II, which can yield cleavage of DNA following secondary structure-specific DNA recognition (Froelich-Ammon et al., *J. Biol. Chem.* 269, 7719–7725 (1994)); iv) DNA-dependent protein kinase, which phosphorylates proteins when activated by the presence of DNA double-stranded to single-stranded transitions (Morozov et al., *Journal of Biological Chemistry.* 269, 16684–16688 (1994); Chan and Lees-Miller. *Journal of Biological Chemistry.* 271, 8936–8941 (1996)); and v) transcription factor EBP-80, which also recognizes double- to single-stranded transitions in DNA (Falzon et al., *Journal of Biological Chemistry.* 268, 10546–10552 (1993)). The sequence specific binding proteins described above utilize a host of motifs for interacting with nucleic acids (zinc fingers, helix-turn-helix, "saddle", etc.). Different potential motifs for this latter group of proteins have not yet been elucidated.

Nucleic acid-dependent ATPases are proteins that previously have not been generally classified as either specific or nonspecific binding proteins. Assays of helicases (molecular motors which unwind double-stranded nucleic acids) frequently require a structural element comprised of both a partial duplex nucleic acid and a nonhomologous tail on the strand to be displaced (Matson and Kaiser-Rogers. *Annu. Rev. Biochem.* 59, 289–329 (1990)). Furthermore, the hydrolysis of ATP by helicases leads to strand displacement (facilitated distortion) presumably through conformational changes in the helicase itself (Wong and Lohman. *Science.* 256, 350–355 (1992)).

Although nucleic acid-dependent ATPases have been identified, the precise role of these enzymes in nucleic acid metabolism has not been clearly elucidated. Moreover, nucleic acid-dependent ATPases have not been proposed as targets for therapeutic intervention through disruption of nucleic acid metabolism. Indeed, efforts into such intervention have focused on nucleotide analogs, such as ddI and AZT, which act on the polynucleotide chain itself in inhibiting DNA replication.

3. SUMMARY OF THE INVENTION

The present invention provides compositions and methods for preventing and treating disease through disrupting nucleic acid metabolism by targeting nucleic acid-dependent ATPase activity. The invention is based in part on the discovery, described below, of the role of a class of compounds known as phosphoaminoglycosides in inhibiting such nucleic acid-dependent ATPase activity. An understanding of the specificity of compounds that inhibit such activity, such as phosphoaminoglycosides, is derived from the underlying physico-biochemical principles of protein-nucleic acid interactions. Although the inventors are not required to provide an explanation of the underlying mechanism by which treatment and prevention are effected by the present invention, and without intending to be bound by any one particular mechanistic theory, the following discussion is provided regarding believed mechanisms of the invention. DNA-dependent ATPases are "molecular motors" that drive distinct cellular processes depending on the other protein domains or subunits with which they are associated. The concept of a molecular motor may be explained by a simple analogy. The molecular motor is analogous to the engine in a toy plane, boat or car. Each toy is composed of different parts brought together for different functions (flying, floating, rolling). The engine is common to each toy and provides the energy consumption which drives the function in each. Similarly, the DNA-dependent ATPase is the molecular motor equivalent to the engine. Multiple protein complexes are formed for each of the different DNA metabolic processes (e.g., DNA replication, DNA repair, transcription, recombination, chromatin remodeling, etc.) and the ATPase functions as a common core component (motor or engine) that drives the processes through the DNA-dependent consumption of ATP.

A further extension of this "molecular motor" model is that disruption of the "molecular motor" would lead to disruption of more complex processes. Disruption of nucleic acid-dependent ATPase activity, therefore, obtains the dual goal of cutting off the fundamental energy source for a number of nucleic acid metabolic processes, without general disruption of all ATPase functions within a living organism. Thus, in accordance with the invention, the energy supply for disease processes which involve relatively rapid nucleic acid metabolism (e.g., replication of infectious agent or cancer cell genetic material) is targeted; while the energy supply for other metabolic functions important to the treated subject (e.g., human, animal, or other vertebrate patient), left unaffected.

The invention is based, in part, on the discovery, described in detail below, of the protein:DNA interactions for DNA-dependent ATPase A. The structural and functional characteristics of DNA-dependent ATPase A activity described herein provides for the designing, testing, and use of therapeutic agents that specifically target these key energy-dependent nucleic acid metabolic processes. Such therapeutic agents that inhibit nucleic acid-dependent ATPases include, but are not limited to, phosphoaminoglycosides. Other researchers have failed to appreciate the importance of the phosphoaminoglycosides as chemotherapeutic agents.

The invention is further based, in part, on the discovery of the novel role of compounds in the inhibition of nucleic acid-dependent ATPase activity. Such inhibitory compounds, both known and novel, include but are not limited to phosphoaminoglycosides. The invention is also based, in part, on the discovery of genes, both human and bovine, encoding DNA-dependent ATPase A, and the recombinant production of a DNA-dependent ATPase polypeptide, as well as a detailed characterization of the activity and function of this polypeptide.

The present invention includes methods for disease intervention through inhibition of nucleic acid metabolism and induction of apoptosis. More specifically, the invention provides methods for prevention and treatment of diseases including, but not limited, to cancer and infectious disease including targeting the process of angiogenesis. The invention also provides compounds which act on such protein targets to inhibit nucleic acid metabolism. In addition, the invention provides screening assays for identifying compounds that inhibit nucleic acid-dependent ATPase activity. Such compounds are useful in the treatment of diseases, including but not limited to cancer and infectious disease. The invention provides protein targets for such intervention, which are used, in accordance with the invention, in screening assays to identify inhibitory compounds. The invention also provides polynucleotides encoding the protein targets of the invention, including novel DNA-dependent ATPase A polynucleotides.

The discovery of novel polynucleotides encoding both bovine and human DNA-dependent ATPase A is described in detail in the Example in Section 6, below.

The recombinant production and characterization of Active DNA-dependent ATPase A Domain (ADAAD) is described in detail in the Example in Section 7, below.

Methods for preparing phosphoaminoglycosides, and the ability of preparations of phosphoaminoglycosides to inhibit nucleic acid-dependent ATPases are described in detail in the Example in Section 8, below.

The Example in Sections 10 demonstrates the ability of phosphoaminoglycosides to disrupt DNA synthesis.

The Examples in Sections 11 and 12, below, demonstrate the ability of phosphoaminoglycosides to inhibit growth of prostate and breast cancer cell lines, respectively.

The Example in Section 13, below, demonstrates the ability of phosphoaminoglycosides to destroy tumors in mice in vivo.

The Examples in Sections 14 and 15, below, demonstrate the ability of phosphoaminoglycosides to inhibit growth and kill the protozoans amoeba and Leishmania, respectively.

The Example in Section 16 demonstrates that inhibition of DNA-dependent ATPase A activity disrupts DNA repair, respectively.

4. BRIEF DESCRIPTION OF THE FIGURES

FIGS. 1A–1B DNA sequence (SEQ ID NO:54) of the full-length bovine DNA-dependent ATPase coding polypeptide region.

FIG. 2. Amino acid sequence (SEQ ID NO:55) of the full-length bovine DNA-dependent ATPase.

FIG. 3. Amino acid sequence (SEQ ID NO:56) of the bovine Active DNA-dependent ATPase A Domain (ADAAD).

FIG. 4. Reaction catalyzed by APH(3')-IIIa.

Figure 5B:
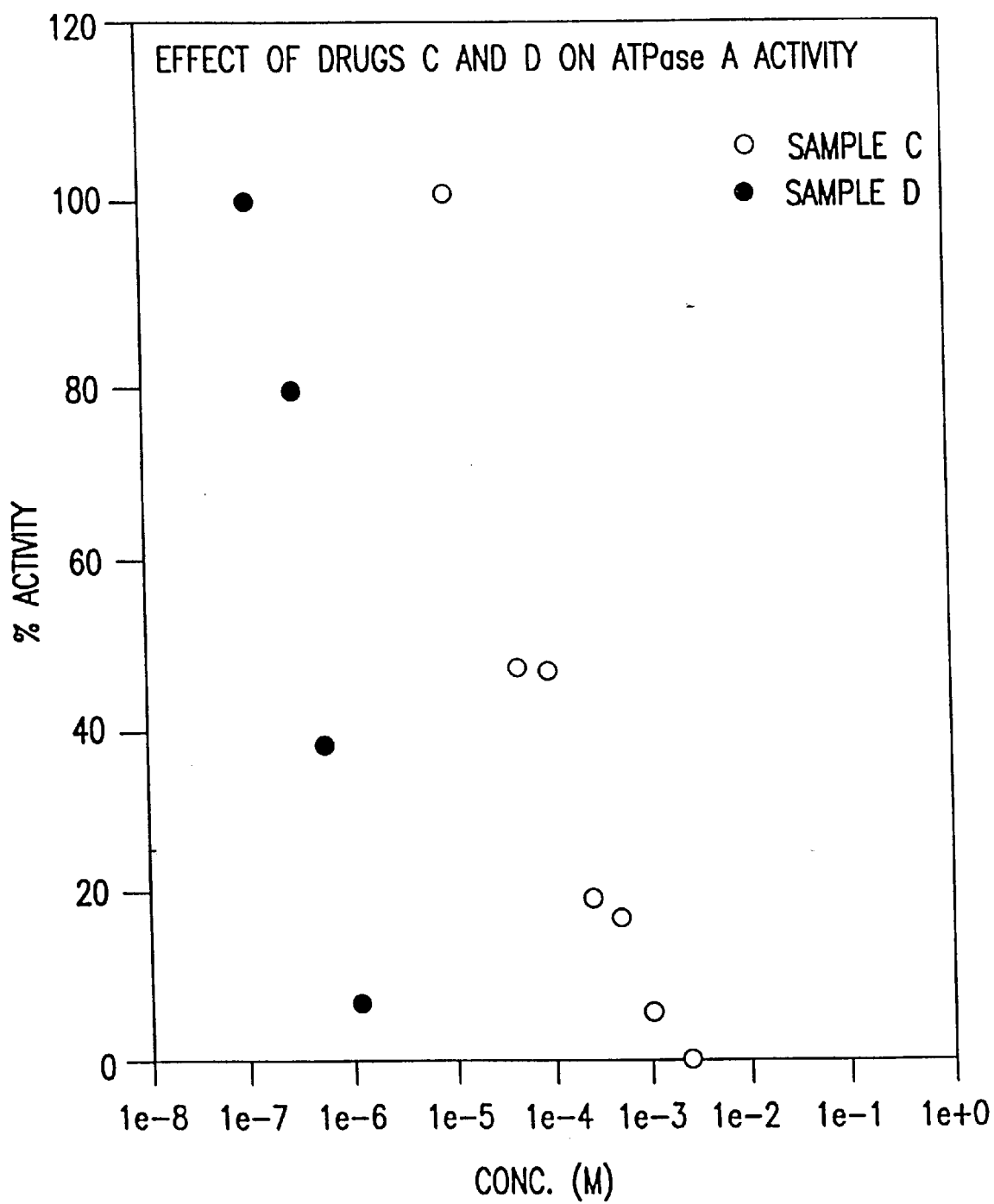
Figure 5C:
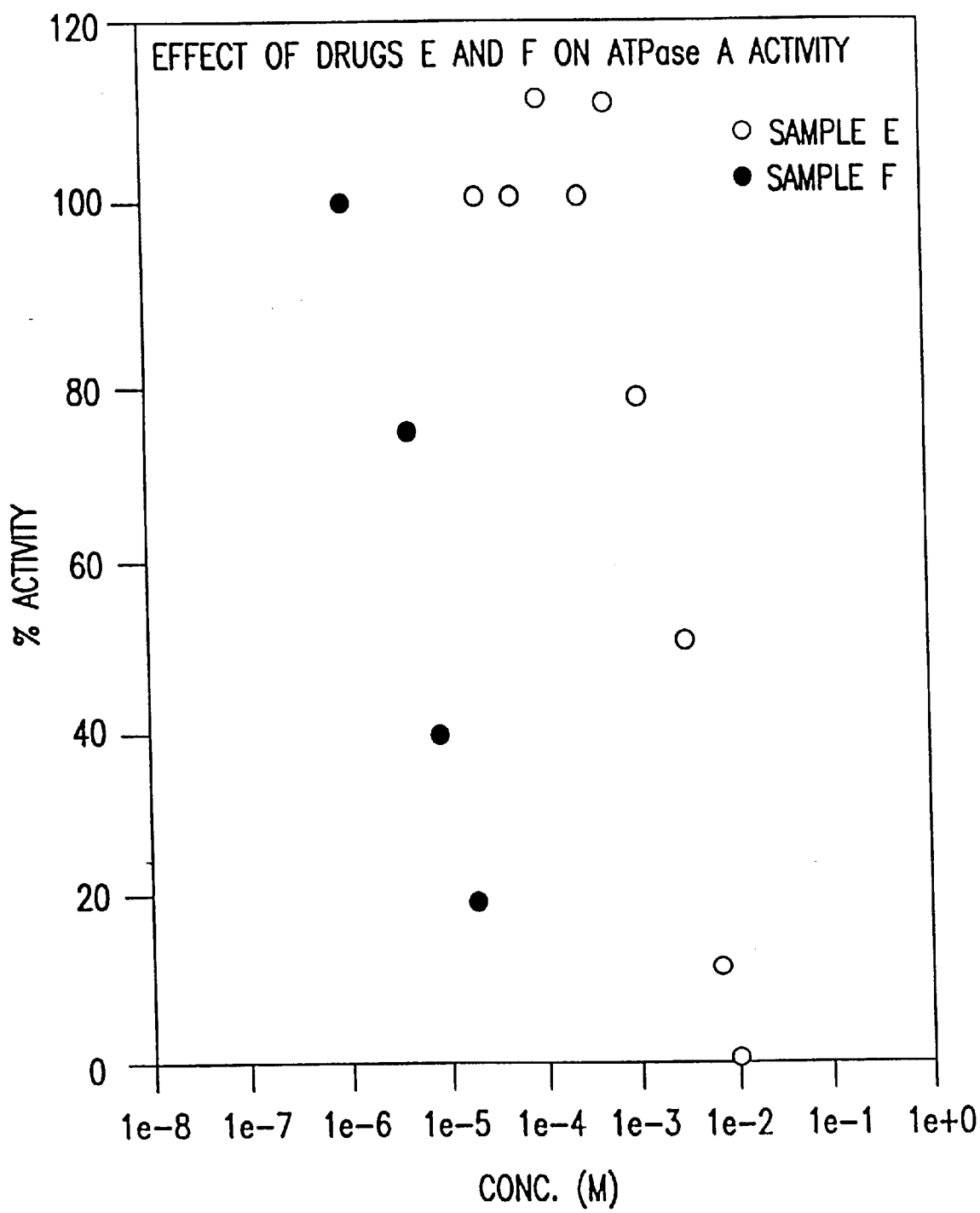

FIGS. 5A, B, and C. Effect of aminoglycosides and phosphoaminoglycosides on DNA-dependent ATPase A activity. The relative ATP hydrolysis activity is plotted against the concentration of each respective compound. In FIG. 5A, open circle (sample A) is kanamycin; and solid circle (sample B) is 3'-phosphokanamycin. In FIG. 5B, open circle (sample C) is neomycin; and solid circle (sample D) is 3'-phosphoneomycin. In FIG. 5C, open circle (sample E) is geneticin; and solid circle (sample F) is 3'-phosphogeneticin.

Figure 6A:
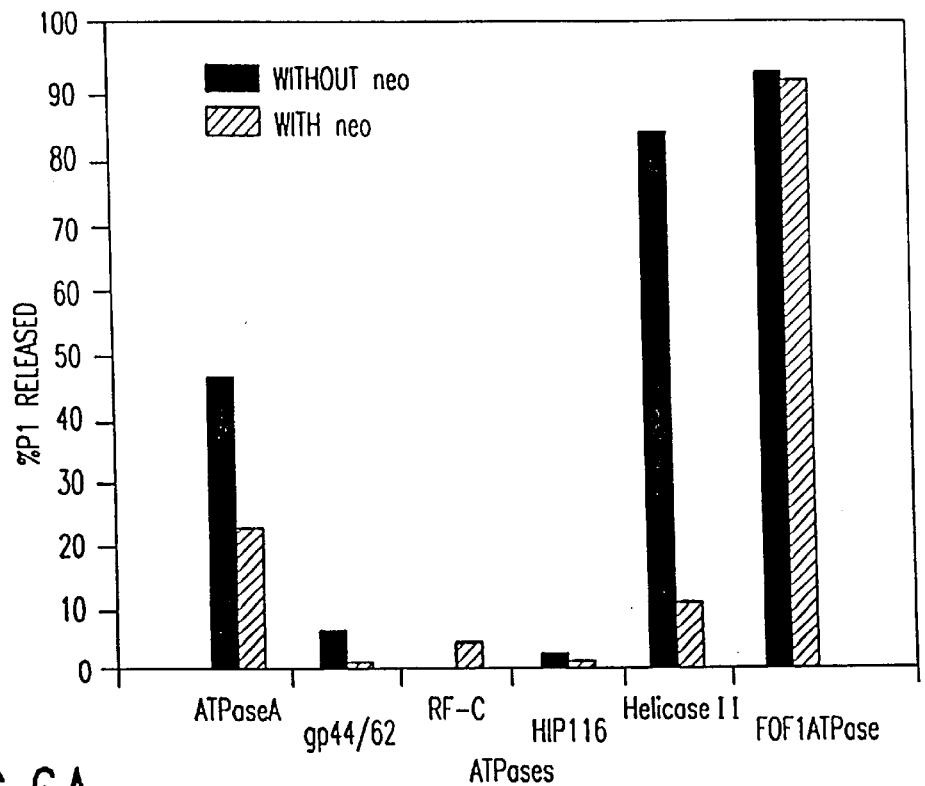
Figure 6B:
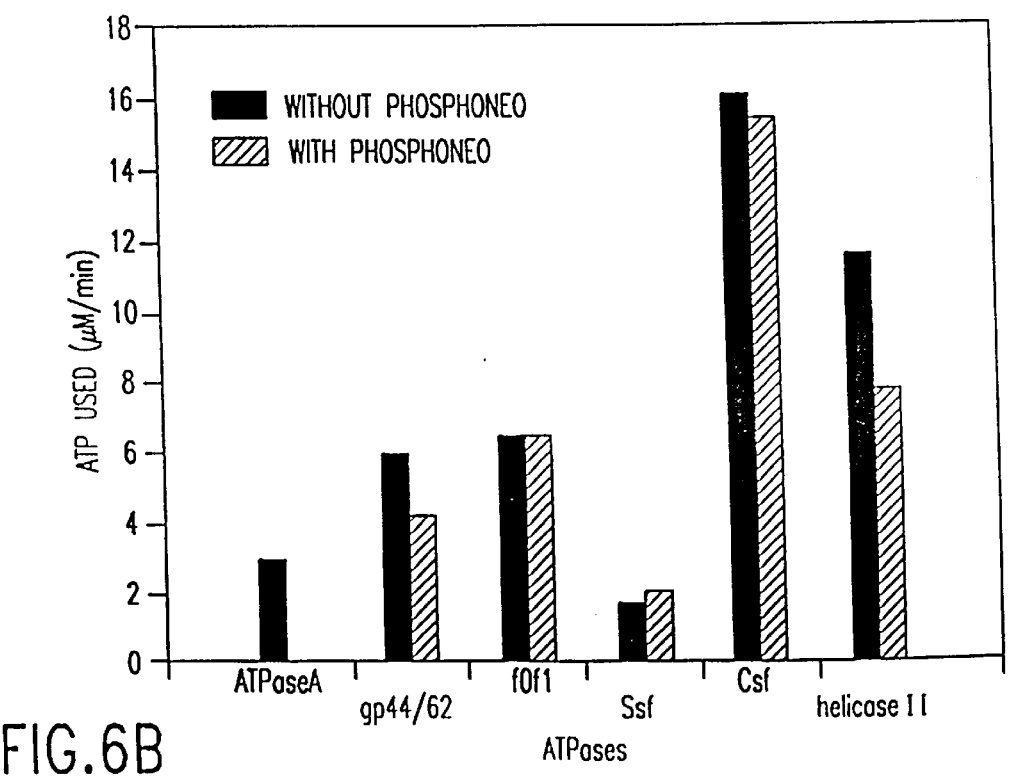

FIGS. 6A and 6B. Effect of neomycin and phosphoneomycin of DNA-dependent and DNA-independent ATPases.

Figure 7:
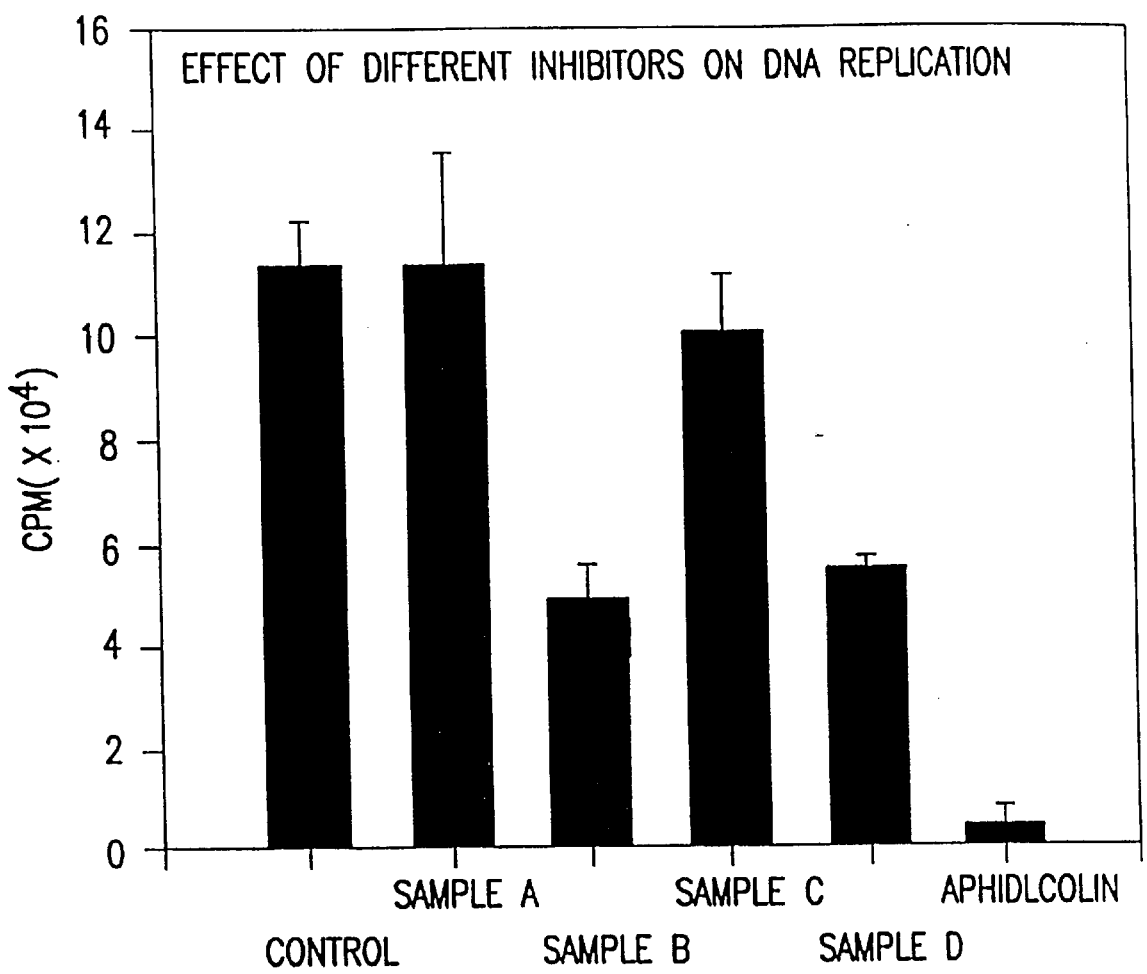

FIG. 7. Effect of different inhibitors on DNA replication. Control=no treatment; sample A=kanamycin (100 $\mu$M); sample B=phosphokanamycin (100 $\mu$M); sample C=neomycin (10 $\mu$M); sample D=phosphoneomycin (10 $\mu$M).

Figure 8:
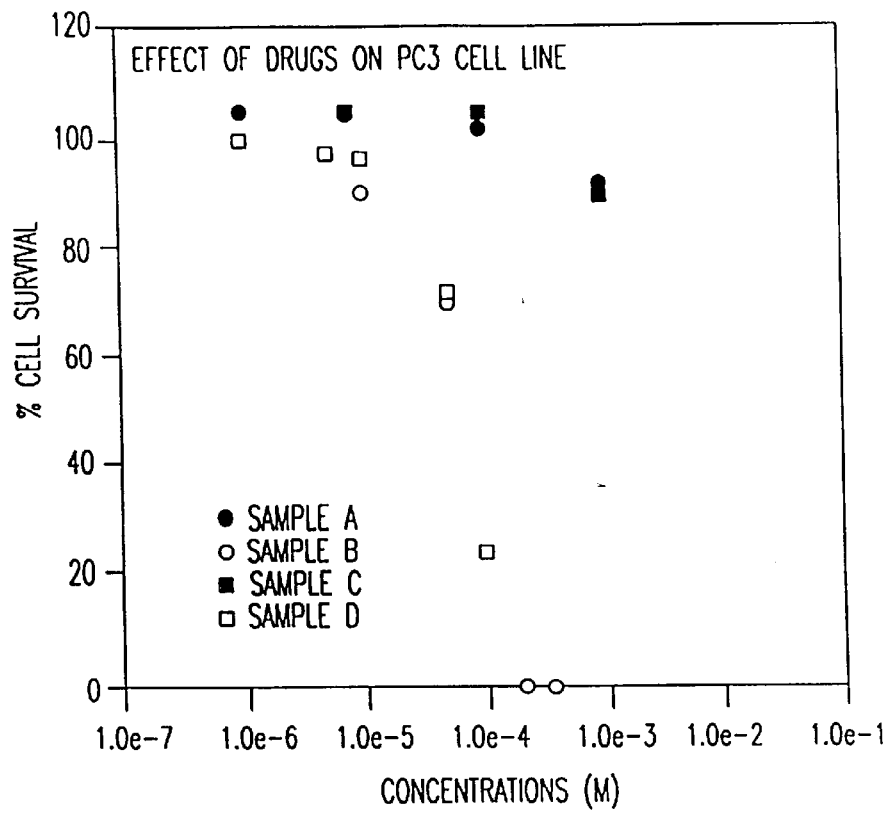

FIG. 8. Effect of inhibitors on PC3 prostate cancer cell line. The percent survival of the cells is plotted against the concentration of each compound. Solid circle (sample A)=kanamycin; open circle (sample B)=phosphokanamycin; solid square (sample C)=neomycin; open square (sample D)=phosphoneomycin.

Figure 9:
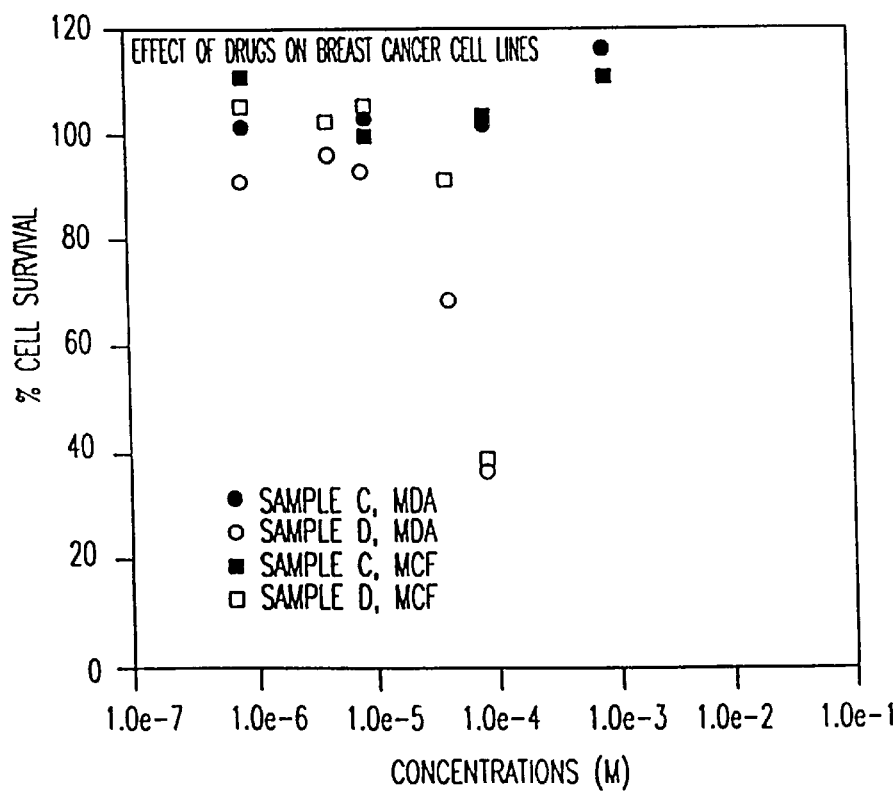

FIG. 9. Effect of inhibitors on breast cancer cell lines. The percent survival of the cells is plotted against the concentration of each inhibitor. Circles=MDA-MB-231 breast cancer cell line; squares=MCF-7 breast cancer cell line. Solid circle and solid square=neomycin (sample C); open circle and open square=phosphoneomycin (sample D).

Figure 10:
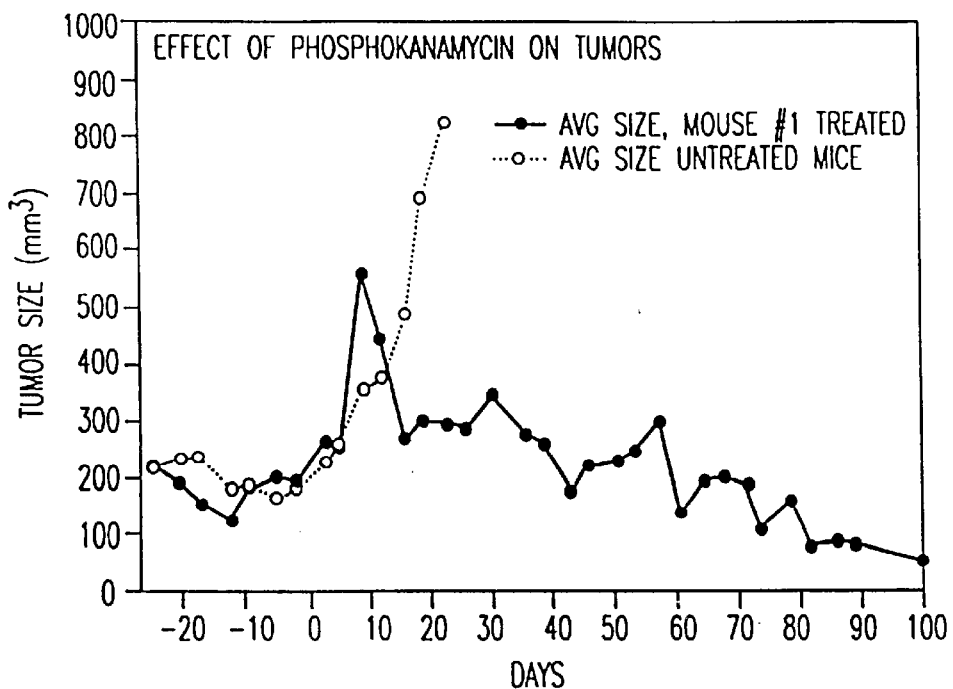

FIG. 10. Effect of phosphokanamycin on tumors. Tumor size is plotted against time in days (day 0=first day after treatment). Solid circle=phosphokanamycin treatment; open circle=no treatment.

Figure 11:
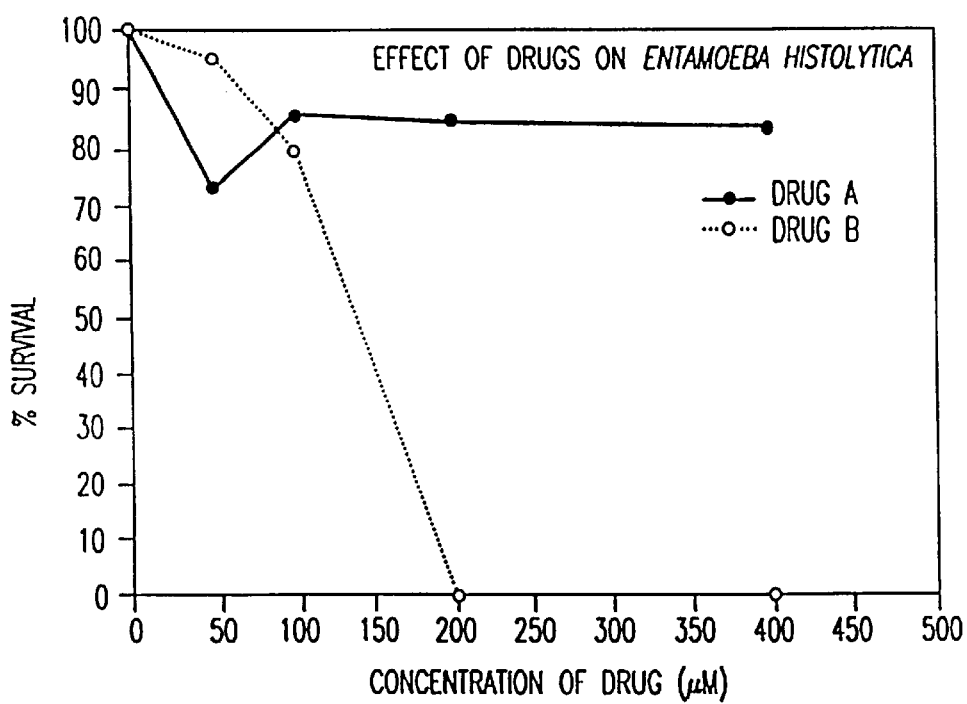

FIG. 11. Effect of inhibitor on amoeba (*Entamoeba histolytica*). Percent of surviving cells is plotted against concentration of compound. Solid circle kanamycin; open circle=phosphokanamycin.

Figure 12A:
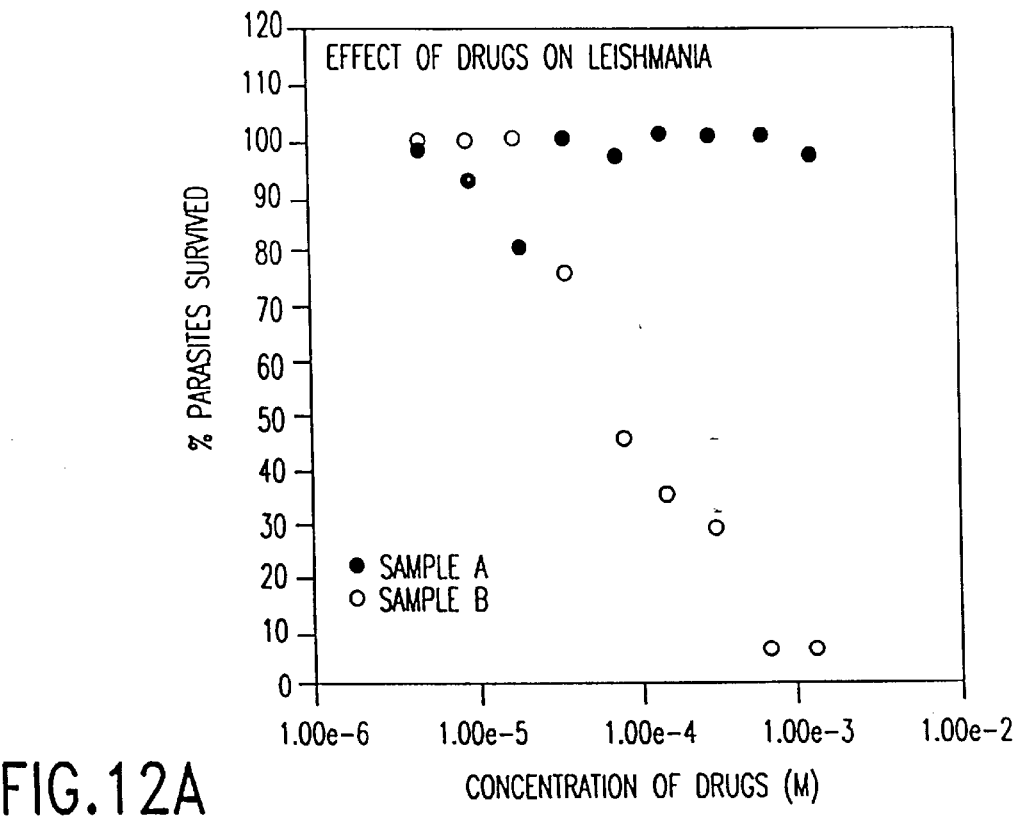
Figure 12B:
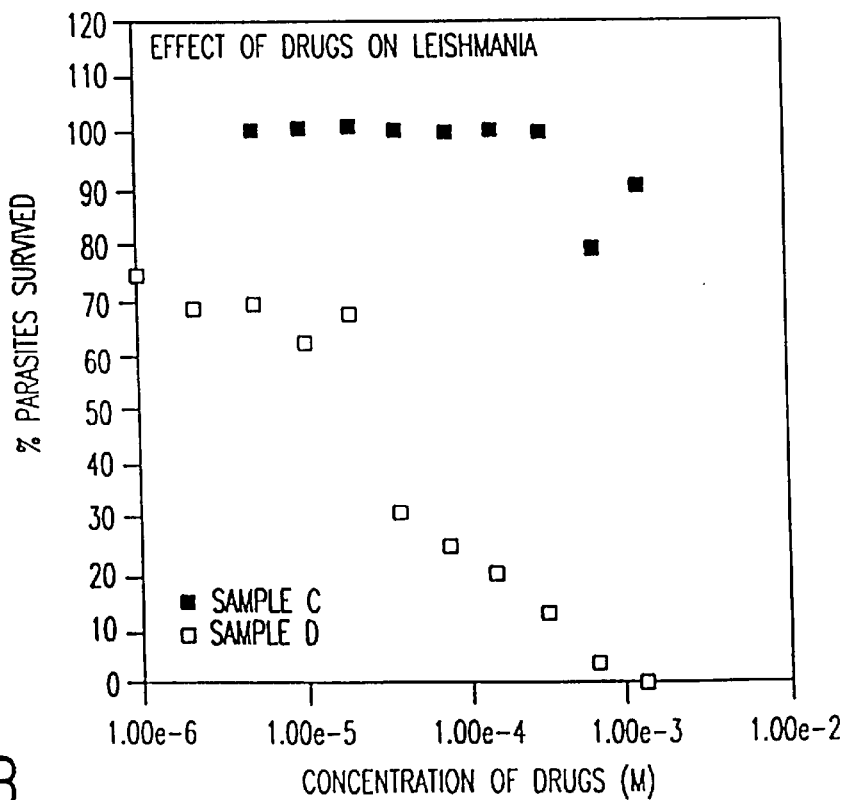

FIGS. 12A and 12B. Effect of inhibitors on Leishmania. Percent of surviving cells is plotted against concentration of compound. In FIG. 12A, solid circle (sample A)=kanamycin; open circle (sample B)=phosphokanamycin. In FIG. 12B, solid square (sample C)=neomycin; open square (sample D)=phosphoneomycin.

FIG. 13. PCR amplification corresponding to a region of the 4 kDa peptide. DNA sequence (SEQ ID NO:57) written as the non-coding strand, from 5' to 3'. Primer sequence is underlined, amplified sequence in plain text. Peptide sequence (SEQ ID NO:58) corresponds to a translation of the DNA sequence (SEQ ID NO:57).

FIG. 14 384/386 Primer DNA sequencing results. Underlined bases in the nucleotide sequence (SEQ ID NO:59) correspond to the two primers. The peptide sequence that matches the Edman degradation sequence is shown in bold.

Figure 15:
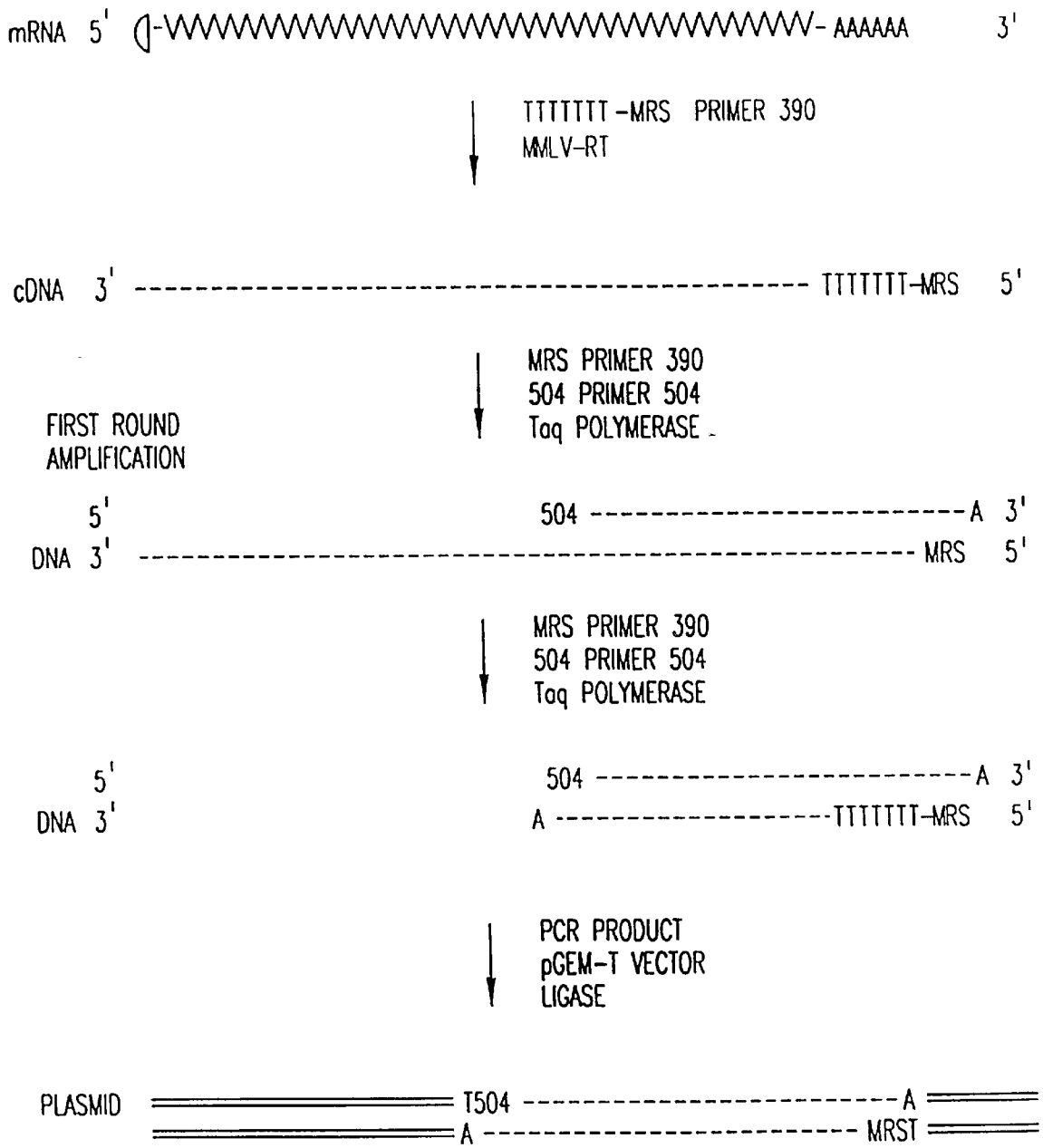

FIG. 15. Protocol for cloning 3' end of DNA-dependent ATPase A gene.

Figure 16:
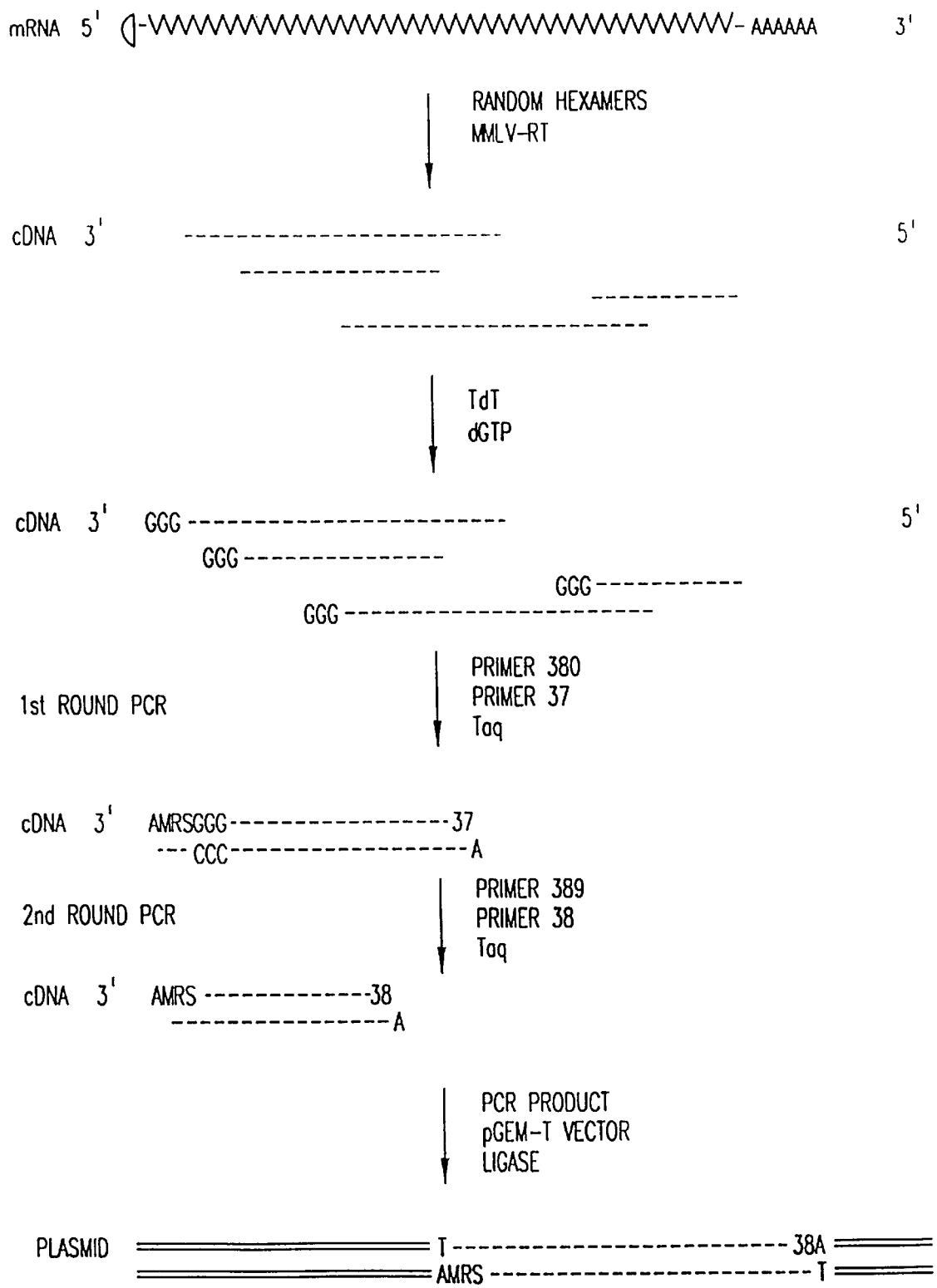

FIG. 16. Protocol for RACE cloning of 5' end of DNA-dependent ATPase A gene.

FIG. 17. DNA sequence (SEQ ID NO:61) of bovine DNA-dependent ATPase A cDNA including 5' and 3' untranslated sequences.

Figure 18:
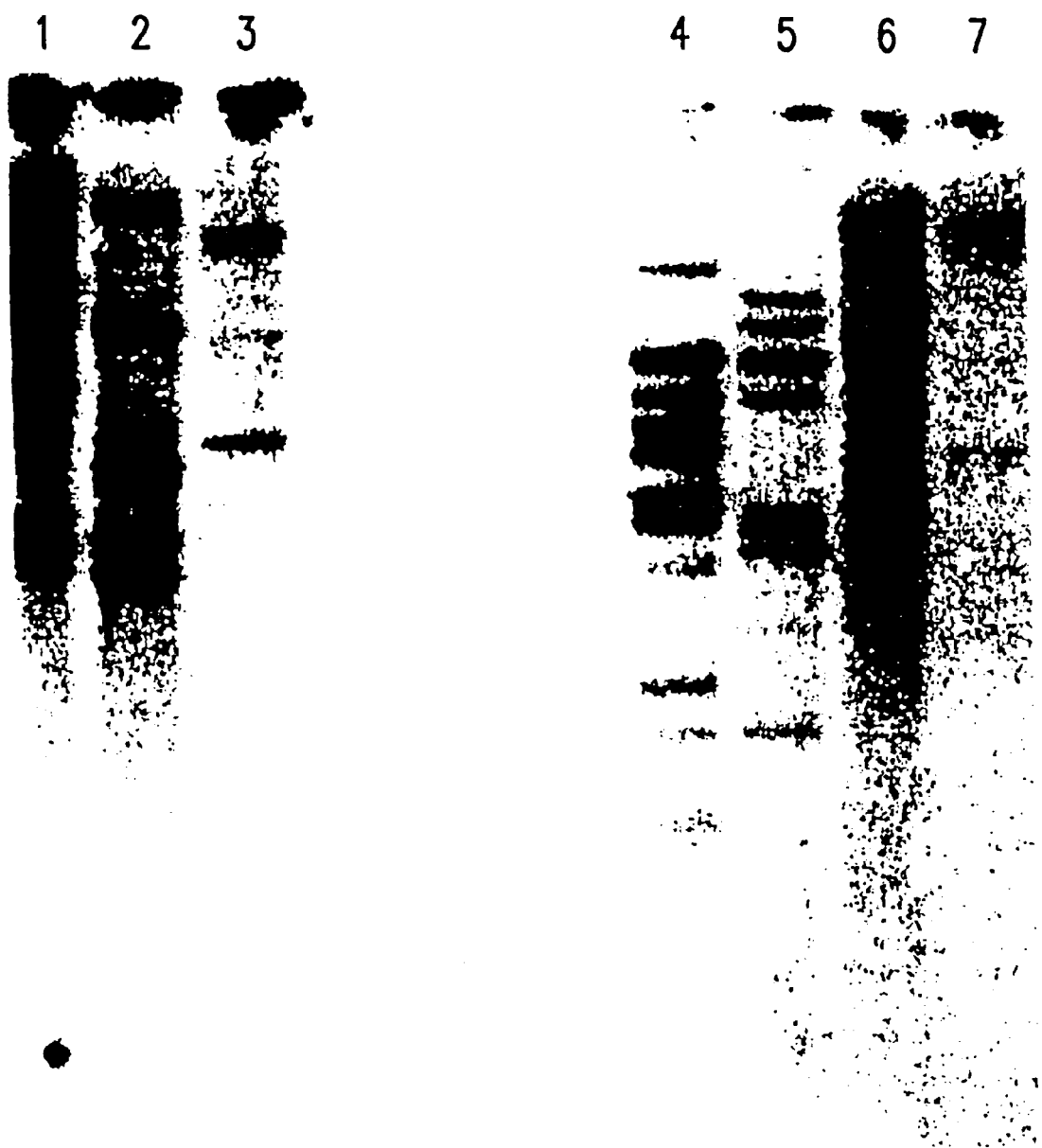

FIG. 18. Southern blot of mammalian (human, bovine, murine) species using pPAT411. Lanes 1 and 5 contain bovine genomic DNA. Lanes 2 and 6 contain genomic murine DNA. Lanes 3 and 7 contain human genomic DNA. Lane 4 contains BstEII-digested λ DNA markers (New England Biolabs), which nonspecifically hybridize with the pPAT411 probe. Lanes 1 through 3 were hybridized to the 5' probe, lanes 4 through 7 were hybridized to the 3' probe.

FIG. 19. The DNA sequence (SEQ ID NO:62) of human DNA-dependent ATPase cDNA, contained in the plasmid pAK505.

FIG. 20. Sequence alignment and comparison of the nucleotide sequence of the human and bovine DNA-dependent ATPase A genes. For each row of alignment, the bovine nucleotide sequence (SEQ ID NO:54) is upper sequence and the human nucleotide sequence (SEQ ID NO:64) is the lower sequence.

FIG. 21. Sequence alignment and comparison of the amino acid sequence of the human and bovine DNA-dependent ATPase A polypeptides. For each row of alignment, the bovine amino acid sequence (SEQ ID NO:55) is upper sequence and the human amino acid sequence (SEQ ID NO:66) is the lower sequence.

5. DETAILED DESCRIPTION OF THE INVENTION

5.1. The Targeted Role of Nucleic Acid-Dependent AtPases in Nucleic Acid Metabolism There are a variety of types of DNA-dependent ATPases (molecular motors) that exist in both prokaryotic and eukaryotic cells. In addition to ATP hydrolysis, many of these enzymes (helicases, topoisomerases, ligases, endonucleases, etc.) have overt biochemical activities that can be monitored in order to study the function of the enzyme. There is however, at least one class of DNA-dependent ATPases whose function beyond ATP hydrolysis is not easily monitored. The prototypical protein in this class is the bacteriophage T4 gene 44 protein (gp44) which plays a role in both DNA replication and transcription. Gp44 appears to use ATP hydrolysis to effect protein conformational changes thereby permitting either assembly or disassembly of multiple protein complexes. Assembly of the multiple-protein complexes seems to promote translocation of functional enzymes along polynucleotide lattices. Only two proteins (RFC/Activator 1 and DNA-dependent ATPase A) from eukaryotic sources have been implicated as having an assembly function similar to gp44. As demonstrated in the Examples in Sections 7 and 16, below, one of these two proteins, DNA-dependent ATPase A, can be purified to near homogeneity and anti-DNA-dependent ATPase A antibodies inhibit DNA replication and DNA repair.

There are many known nucleic acid modifying enzymes that hydrolyze ATP resulting in changes to the nucleic acid. substrate (e.g., helicases, nucleases, topoisomerases, ligases, and recombinases). However, nucleic acids do not appear to be a substrate for a few nucleic acid-dependent adenosinetriphosphatases (ATPases) and consequently in these cases the nucleic acid is generally regarded as an effector of the enzymatic activity. The role of DNA as an effector (but not substrate) is shared by some DNA-dependent ATPases that are required for DNA replication such as in the *E. coli* DNA polymerase III holoenzyme complex and the bacteriophage T4 gene 44 protein (gp44) (Tsuchihashi and Kornberg. *J. Biol. Chem.* 264, 17790–17795 (1989); Jarvis et al., *J. Biol. Chem.* 264, 12717–12729 (1989)); proteins frequently described as "locking" other DNA-modifying enzymes onto the polynucleotide to form a sliding clamp. For both τ-subunit and gp44, DNA-binding is required to effect ATP hydrolysis, which in turns locks a non-DNA binding protein onto the DNA apparently through conformational changes resulting in a topological linkage of the protein around the DNA (Kuriyan and O'Donnell. *J. Mol. Biol.* 234, 915–925 (1993); Hockensmith et al. *J. Biol. Chem.* 268, 15721–15730 (1993)). In these cases, the DNA effecters are ultimately modified by the assembled complexes but are not modified by the ATPases themselves. The DNA-dependent ATPase is responsible for DNA structural recognition so that the correct proteins can be assembled onto the DNA in a non-sequence dependent manner. Thus, the DNA-dependent ATPase functions as a molecular motor, consuming an energy-yielding substance (ATP) to drive conformational changes in proteins required for DNA metabolic processes.

DNA-dependent ATPases of both prokaryotic and eukaryotic organisms can be classified according to the type of polynucleotide that is the most efficient effector of ATP hydrolysis. Generally, DNA-dependent ATPases fall into three classes: i) preference for single-stranded DNA (ssDNA) (e.g. helicases); ii) preference for double-stranded DNA (dsDNA) (e.g. topoisomerases, gyrases and endonucleases); and iii) no strand preference (e.g. recombination proteins—recA).

The experiments described herein below extend beyond previous work that only suggested that there may be a fourth category. The ATPases of this fourth category are characterized by preference for polynucleotides that form specific secondary structures such as those that contain both single-stranded and double-stranded regions (e.g. gp44) (Hockensmith et al., *Biochemistry.* 25; 7812–7821 (1986); Jarvis et al., *J. Biol. Chem.* 264, 12717–12729 (1989)). DNA-dependent ATPases with this fourth type of effector preference are expected to play a role at the primer-template junction in DNA replication, at a DNA unwinding element (DUE), at a transcription bubble, at DNA damage sites, or at local areas of DNA unwinding resulting from structural alterations of the DNA (i.e. supercoiling, protein binding (histones), etc.). The ATPase activity and effector preference of eukaryotic DNA-dependent ATPase A closely. parallels that of gp44 (Hockensmith et al., *Biochemistry.* 25, 7812–7821 (1986); Jarvis et al., *J. Biol. Chem.* 264, 12717–12729 (1989)) and, thus could be classified as using this fourth type of effector.

Many eukaryotic DNA-dependent ATPases fall into the fourth class of ATPases, however, this class of ATPases has not previously been proposed as targets of therapeutic intervention.

As described in detail, below, a class of inhibitory compounds have been demonstrated to inhibit several members of this fourth class of ATPase. For example, DNA-dependent ATPase A, Mot1, DNA-dependent Protein Kinase, and gp44/62 have been shown to be inhibited by phosphoaminoglycosides in accordance with the invention. Thus, this fourth class of ATPase, i.e., nucleic acid-dependent ATPases that use as an effector double stranded/single stranded junctions, are a novel class of targets for treatment and prevention of disease through disruption of nucleic acid metabolism.

In addition to characterizing DNA-dependent ATPases based on their effector preference, certainly similarities may exist in the amino acid sequence of the protein which would aid the classification of these enzymes. The amino acid sequence of DNA-dependent ATPase A has the most similarity with a relatively new family of proteins which appear to be DNA-dependent ATPases (Carlson and Laurent. *Curr. Opin. Cell Biol.* 6, 396–402 (1994); Bork and Koonin. *Nucleic Acids Res.* 21, 751–752 (1993)). The genes from seven members (SNF2, STH1, YAL001, MOT1, RAD54, RAD16, RAD5) of this family have been identified in *Saccharomyces cerevisiae* through direct genetic manipulations, while additional members have been identified from humans and Drosophila by amino acid sequence comparisons. Biochemical analysis of these DNA-dependent ATPase proteins has been reported for: i) a fusion product of the c-terminal portion of SNF2, which has been shown to have a low level of ATP hydrolytic activity (~0.02 $\mu$mol/min/mg) in the presence of double-stranded DNA (Laurent et al., *Genes Dev.* 7, 583–591 (1993)); ii) a fusion product of the c-terminal portion of MOT1, which has been shown to have a specific activity of ~0.33 $\mu$mol/min/mg but no dependence on a DNA effector (Auble et al., *Genes Dev.* 8, 1920–1934 (1994)); and iii) HIP116 protein from HeLa cell nuclear extracts (no specific activity reported for ATP hydrolysis), which shows a ~7-fold stimulation of ATP hydrolysis by some DNA effectors (Sheridan et al., *J. Biol. Chem.* 270, 4575–4587 (1995)). The effect of DNA secondary structures on this family of proteins has not been reported.

The yeast gene known as SNF2 or SWI2 is perhaps the best known member of this family. Although the Snf2 protein positively affects the expression of many diverse genes, it does not contain any motifs characteristic of DNA-binding proteins (Winston and Carlson. *Trends Genet.* 8, 387–391 (1992); Peterson and Herskowitz. *Cell.* 68, 573–583 (1992)) nor is there any experimental evidence for the binding of this DNA-dependent ATPase to DNA (Winston and Carlson. *Trends Genet.* 8, 387–391 (1992)). The Snf2 protein appears to be a component of a large multi-subunit complex (Peterson et al., *Proc. Natl. Acad. Sci. U.S.A.* 91, 2905–2908 (1994); Kwon et al., *Nature.* 370, 477–481 (1994); Cote et al., *Science.* 265, 53–60 (1994); Cairns et al., *Proc. Natl. Acad. Sci. U.S.A.* 91, 1950–1954 (1994)) and may serve as a bridge (or molecular matchmaker; (Sancar and Hearst. *Science.* 259, 1415–1420 (1993))) between specific DNA-binding proteins and the transcriptional apparatus (Okabe et al., *Nucleic Acids Res.* 20, 4649–4655 (1992); Peterson and Herskowitz. *Cell.* 68, 573–583 (1992)). The similarity of ATPase domains has been the main criteria for grouping proteins into the SNF2 family. It is clear that the peptide sequence outside the ATPase domain contributes to function and that not all of the members of this family have similar metabolic functions (Carlson and Laurent. *Curr. Opin. Cell Biol.* 6, 396–402 (1994)). The STH1 gene was identified as homologous to SNF2, but unlike SNF2, STH1 is essential for mitotic growth of yeast cells (Laurent et al., *Mol. Cell. Biol.* 12, 1893–1902 (1992)). Similar studies of other members of this family have led to proposed metabolic functions for proteins in this family including: DNA repair; transcriptional regulation (positive and negative); and chromatin remodeling.

The homologous regions which define the SNF2 family have been identified as putative helicase domains. Although a number of members of the SNF2 family of proteins play a role in transcription (Drapkin et al., *Cell.* 77, 9–12 (1994); Okabe et al., *Nucleic Acids Res.* 20, 4649–4655 (1992); Winston and Carlson. *Trends Genet.* 8, 387–391 (1992); Laurent et al., *Genes Dev.* 7, 583–591 (1993)), a process which might utilize a helicase, the strand effector preference for ATP hydrolysis by these proteins is not consistent with helicase function. The strand effector preference has only been determined for the SNF2 C-terminal fusion product and the HIP116 protein. Both prefer a double-stranded effector by more than two-fold over a single-stranded effector (Sheridan et al., *J. Biol. Chem.* 270, 4575–4587 (1995); Laurent et al., *Genes Dev.* 7, 583–591 (1993)); a fact which is inconsistent with the putative helicase function of these proteins since helicases tend to prefer ssDNA effectors (Matson and Kaiser-Rogers. *Annu. Rev. Biochem.* 59, 289–329 (1990)). Using the putative helicase domains to search for sequence similarities, Henikoff (Henikoff. *TIBS.* 18, 291–292 (1993)) has suggested that the pox virus DNA-dependent ATPases (the VATP group) should be included as members of the SNF2 family of proteins. VATP group proteins have been purified but efforts to detect helicase activity have been unsuccessful (Kunzi and Traktman. *J. Virol.* 63, 3999–4010 (1989); Henikoff. *TIBS.* 18, 291–292 (1993)). Thus, the lack of demonstrated helicase activity in any member of the SNF2 family results in the recommendation that serious consideration be given to ATP-dependent roles that do not require DNA unwinding (Henikoff. *TIBS.* 18, 291–292 (1993)). One possible role might include assembly/disassembly of multiprotein-DNA complexes at specific DNA structures and/or translocation of these complexes along a duplex DNA molecule, much like the proteins involved in the sliding clamps of *E. coli* and bacteriophage T4. Support for such a role comes from studies which demonstrate that an SNF2 protein complex can facilitate binding of TATA binding protein to nucleosomal DNA and can disrupt nucleosomes (Kwon et al., *Nature*. 370, 477–481 (1994); Imbalzano et al., *Nature*. 370, 481–485 (1994)).

The bacteriophage T4 DNA-dependent ATPase assembly, composed of the gene 44/62 and 45 proteins (gp44/62, gp45), is known to play an essential role in DNA replication and has been the subject of many studies to understand its structure and role (Munn and Alberts. *J. Biol. Chem.* 266, 20034–20044 (1991b); Munn and Alberts. *J. Biol. Chem.* 266, 20024–20033 (1991b); Capson et al., *Cell.* 65, 249–258 (1991b); Hockensmith et al., *J. Biol. Chem.* 268, 15721–15730 (1993b)). While T4 DNA replication is governed by the 3-protein accessory complex, there is also evidence for the role of these proteins in the transcriptional regulation of the T4 late genes. Gp45 has been shown to be essential for expression of the late T4 genes (Wu et al., *J. Mol. Biol.* 96, 539–562 (1975)) and biochemical evidence suggests that gp45 is an RNA polymerase-binding protein (Ratner. *J. Mol. Biol.* 88, 373–383 (1974)). The work of Wu et al. (Wu et al., *J. Mol. Biol.* 96, 539–562 (1975)) has shown that among the replication genes only a mutation in gene 45 results in almost complete abolition of late gene expression. Recent work has shown that gp45 by itself is insufficient for stimulation of T4 late transcription in an in vitro system and that all three of the polymerase accessory proteins (gp45, gp44/62) are required for stimulation (Tinker et al., *Cell.* 77, 225–237 (1994); Herendeen et al., *Science.* 245, 952–958 (1989)). Thus, the role that gp45 plays in both replication and transcription is dependent on DNA-dependent ATP hydrolysis by gp44.

Frequently, prokaryotic processes have served as models for eukaryotic processes. Studies of nucleic acid metabolism in prokaryotes and eukaryotes have occurred almost simultaneously, but the vast majority of progress has occurred in prokaryotes as a direct result of the ease of genetic manipulation. Additionally, the rapid rate of growth of prokaryotic cells and the obligatory high levels of proteins involved in nucleic acid metabolism have enhanced efforts to identify, purify, and characterize those systems. Much of the progress in eukaryotic systems has continued to rely on traditional biochemical approaches such as protein purification followed by in vitro assays, Edman degradation of the protein, and subsequent cloning of the cDNA derived from the mRNA encoding the protein (Auble et al., *Genes Dev.* 8, 1920–1934 (1994); Zhang et al., *Biochemistry*. 30, 11742–11750 (1991); Bunz et al., *Proc. Natl. Acad. Sci. U.S.A.* 90, 11014–11018 (1993)). The bacteriophage T4 DNA replication process has had a tremendous impact on the development of models for eukaryotic DNA replication. As discussed above, the DNA-dependent ATPase (gp44) is now believed to participate in assemblies of proteins involved in both DNA replication and transcription. The sharing of proteins in different nucleic acid metabolic processes is an emerging theme in eukaryotes and gp44 may serve as a model for this theme. That is, DNA-dependent ATPases may play a role in assembling multiple complexes with differing functions.

As detailed below, DNA-dependent ATPase A is a protein: i) whose ATPase function is similar to gp44; ii) whose sequence contains motifs similar to a family (SNF2) of proteins which are genetically implicated in transcription, DNA repair, and recombination; iii) that binds to specific DNA structures in a sequence independent fashion; iv) that appears to play a role in DNA synthesis and DNA repair; v) that can be targeted with specific chemicals that compete for DNA binding and yield cell death when applied to a number of cell types.

The various aspects of the invention are described in the subsections below with specific reference to DNA-dependent ATPase A; however, the invention is not limited to DNA-dependent ATPase A and encompasses other nucleic acid-dependent ATPases that use as an effector a double stranded/single stranded junction as targets for therapeutic intervention.

5.2. The Nucleic Acid-Dependent ATPase a Polynucleotides

Novel polynucleotides encoding DNA-dependent ATPase A are shown in FIGS. 1A–B, 17 and 19. Specifically, a cDNA sequence containing the entire coding sequence of bovine DNA-dependent ATPase A is shown in FIGS. 1A–B and 17. The DNA-dependent ATPase A polypeptide coding region extends from nucleotide position 1 to 2826 (including the stop codon) in FIGS. 1A–B and 17. The coding region for the 82 kDa Active DNA-dependent Adenosine triphosphatase A Domain (ADAAD) extends from nucleotide position 643 to 2823 (excluding the stop codon) in FIG. 1A–B and 17. This ADAAD encoding polynucleotide was subcloned into an expression vector (pRM102) which was used, in accordance with the invention, to overexpress and produce an 82 kDa protein having high DNA-dependent ATPase activity.

Human cDNA encoding the human DNA-dependent ATPase A is shown in FIG. 19.

The novel polynucleotides disclosed herein can be obtained by using the novel nucleotide sequences disclosed as either hybridization probes or PCR primers.

In addition to the gene sequences described above, homologues of such sequences as may, for example, be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated DNA-dependent ATPase gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y, each of which is hereby incorporated in its entirety.

Further, a previously unknown nucleic acid-dependent ATPase polynucleotide sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a nucleic acid-dependent ATPase.

The PCR product may be subcloned and sequenced to insure that the amplified sequences represent the sequences of a nucleic acid-dependent ATPase-like nucleotide sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology, including, for example, the well-known RACE procedure, may also be utilized to isolate full-length cDNA sequences using the partial cDNA sequences disclosed herein. To obtain full-length human DNA-dependent ATPase A, for example, RNA may be isolated, following standard procedures, from an appropriate cellular or tissue source, including but not limited to HeLa cells, PC3 cells (prostate cancer cell line), and BT20 cells (breast tumor cell line). A reverse transcription reaction may be performed on the RNA using an oligonucleotide primer specific for the most 5' end of the amplified fragment for the priming of first strand synthesis. The resulting RNA/DNA hybrid may then be "tailed" with quanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The invention contemplates, in addition to the DNA sequences disclosed herein, 1) any DNA sequence that encodes the same amino acid sequence as encoded by the DNA sequences shown in FIGS. 1A–B and 19; 2) any DNA sequence that hybridizes to the complement of the coding sequences disclosed herein (see FIGS. 1A–B and 19) under highly stringent conditions, e.g., washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed herein (see FIGS. 1A–B and 19) under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also encompasses 1) DNA vectors that contain any of the coding sequences disclosed herein (see FIGS. 1A–B and 19), and/or their complements (i.e., antisense); 2) DNA expression vectors that contain any of the coding sequences disclosed herein (see FIGS. 1A–B and 19), and/or their complements (i.e., antisense), operatively associated with a regulatory element that directs the expression of the coding and/or antisense sequences; and 3) genetically engineered host cells that contain any of the coding sequences disclosed herein (see FIGS. 1A–B and 19), and/or their complements (i.e., antisense), operatively associated with a regulatory element that directs the expression of the coding and/or antisense sequences in the host cell. Regulatory element includes, but is not limited to, inducible and non-inducible promoters, enhancers, operators and other elements known to those skilled in the art that drive and regulate expression. The invention includes fragments of any of the DNA sequences discussed or disclosed herein.

5.3. Nucleic Acid-Dependent ATPase Polypeptide Targets

Sections 5.3.1 and 5.3.2 describe particular polypeptides that can be used in accordance with the invention. Nucleic acid-dependent ATPase polypeptides can be used, for example, as components in the assays described in Section 5.5, below.

These polypeptides may be derived from natural sources, e.g., purified from cells and virus, respectively, using protein separation techniques well known in the art; produced by recombinant DNA technology using techniques known in the art (see e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W.H. Freeman & Co., N.Y., pp. 50–60). The composition of the synthetic peptides may be confirmed by amino acid analysis or sequencing; e.g., using the Edman degradation procedure (see e.g., Creighton, 1983, supra at pp. 34–49).

The peptide fragments should be produced to correspond to the nucleic acid recognition and ATP recognition domains, and residues essential for ATP hydrolysis of the respective proteins. Any number of methods routinely practiced in the art can be used to identify and isolate the protein's nucleic acid recognition site. These methods include but are not limited to mutagenesis of one of the genes encoding the protein and screening for disruption of binding to nucleic acid in a gel shift assay, or mutagenesis of the host cell gene and selecting for resistance to phosphoaminoglycoside inhibition. Compensating mutations in the viral gene can be selected which allow for phosphoaminoglycoside inhibition. Sequence analysis of the genes encoding the respective proteins will reveal the mutations that correspond to the region of the protein involved in nucleic acid recognition. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the protein components which may be used in the assays of the invention need not be identical to the reported sequence of the genes encoding them. The assay components may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

In addition, the proteins or protein fragments used in accordance with the invention in, for example, screening assays may be fused to other, heterologous proteins. Recombinant DNA technology methods that are well-known in the art can be used to produce fusion proteins that can facilitate labeling, immobilization and/or detection of nucleic acid-dependent ATPase.

Such fusion protein are useful, for example, in coupling the protein to solid surface, such as a microtitre plate for screening assays, or a test strip used in a test kit.

5.3.1. DNA-Dependent ATPase A Polypeptides

In a preferred embodiments of the invention for screening inhibitory compounds and therapeutic intervention, the target protein is DNA-dependent ATPase A. The novel polynucleotides encoding DNA-dependent ATPase A are described in Section 5.2, above. The full-length amino acid sequence for bovine DNA-dependent ATPase A is shown in FIG. 2. A method for producing the full-length bovine DNA-dependent ATPase A protein is described in detail in the Example in Section 9, below. The amino acid sequence of an 82 kDa fragment which was overexpressed and recovered as an active protein, as described in the Example in Section 7, below, is shown in FIG. 3. Thus, either full-length protein or sub-fragments containing DNA-dependent ATPase activity are useful in the screening assays for identifying inhibitors described in Section 5.5., below.

In addition, amino acid sequence encoded by human DNA-dependent ATPase A is shown in FIG. 21.

5.3.2. Other Target ATPases

Table 1, below, lists of ATPases that are members of the SNF2 family, and are targets for intervention that can be used to assay for inhibitors in accordance with the invention. For members of the SNF2 family, see Carlson and Laurent, Current Opinion in Cell Biology 1994, 6:396–402; and Eisen et al., Nucleic Acids Research 1995, 23:2715–2723. The members of the SNF2 family of proteins have been identified by amino acid sequence similarity across seven domains commonly known as "helicase domains". These domains represent the DNA binding and ATP binding domains that are also common to DNA-dependent ATPase A (ADAAD).

TABLE 1

SNF2 Family Members

| Protein | Organism | Suggested function |
| --- | --- | --- |
| SNF2 | S. cerevisiae | Transcriptional Activator/DNA-dependent ATPase (SNF2 aliases include SWI2, GAM1, and TYE3) |
| STH1/NPS1 | S. cerevisiae | Cell cycle phase control |
| MOT1 | S. cerevisiae | Transcriptional Repression |
| RAD5 | S. cerevisiae | DNA repair |
| RAD16 | S. cerevisiae | DNA excision repair |
| RAD54 | S. cerevisiae | Recombinational repair |
| FUN30/YAL001 | S. cerevisiae | Mutants show increased UV resistance |
| rad8 | S. pombe | Recombinational repair |
| lodestar | Drosophila | Mitotic chromosome segregation |
| brm | Drosophila | Gene activator |
| ISWI | Drosophila | Unknown |
| Brg1 | Mouse | Binds Rb |
| mbrm | Mouse | Unknown |
| Etl-1 | Mouse | Unknown |
| CHD-1 | Mouse | DNA-binding protein |
| BRG1 | Human | Transcriptional Activation |
| hbrm | Human | Transcriptional Activation |
| hSNF2L | Human | Unknown |
| ERCC6 | Human | DNA excision repair |
| Hpb | Bacillus cereus | Unknown |
| hepA | Escherichia coli | Induced by DNA damage |
| Civ | Chilo iridescent virus | Unknown |
| F37A4.8 | C. elegans | Unknown |
| YB95 | S. cerevisiae | Unknown |
| SYGP4 | S. cerevisiae | Unknown |
| RAD26 | S. cerevisiae | Transcription-coupled repair |
| DNRPPX | S. pombe | Unknown |
| YB53 | S. cerevisiae | Unknown |
| NUCPRO | Human | Unknown |
| NUCPRO | Mouse | Unknown |
| RAD8 | S. pombe | Mutants show increased UV sensitivity |
| HIP116A | Human | DNA-dependent ATPase |
| NHCG42 | A. californica | Unknown |
| hSNF2α | Human | |
| hSNF2β | Human | |
| 89B helicase | Drosophila | |
| NURF | Drosophila | |

The invention also includes assaying for inhibitors of protein complexes containing the ATPases described herein. For example, the following protein complexes have been found, in accordance with the invention (see FIGS. 6A and 6B), to be inhibited by the phosphoaminoglycoside phosphoneomycin: Bacteriophage T4 gp44/62; Bacteriophage T4 gp44/62 plus gp45; and DNA-dependent Protein Kinase.

Indeed, the invention encompasses the inhibition of enzymes involved in nucleic acid metabolism that recognize double strand/single strand junctions, such as stem-loop structures, but which do not themselves hydrolyze ATP. The invention includes, therefore, assaying the inhibition of such nucleic acid metabolic activity, which includes, for example, ATP hydrolysis, RNA hydrolysis, and DNA binding activity.

For example, the Ku protein is a subunit of the multimeric DNA-dependent Protein Kinase complex which is responsible for DNA binding. Ku binding to DNA triggers a conformational change in the complex which allows for binding and hydrolysis of ATP by other proteins in the complex. Thus, in accordance with the invention, kinase activity of the complex is inhibited indirectly through direct inhibition of the DNA binding activity of the Ku protein. Accordingly, the Ku protein, and other proteins that do not themselves hydrolyze ATP, can be used as targets for disrupting nucleic acid metabolism, and for identifying compounds for use in such intervention. Inhibition of Ku can be assayed using routine methods well known in the art, as described, for example, in Chan, D. W. and Lees-Miller, S. P., 1996, J. Biol. Chem. 271: 893.6–8941, which is hereby incorporated by reference in its entirety.

In further embodiments of the invention, the phosphoaminoglycoside compounds described herein can be used to target the process of angiogenesis through inhibition of the protein angiogenin. Angiogenesis is a process that is recognized as critical to the development of tumors and other disease states. Angiogenin has recently been described as binding to a specific DNA structure (Nobile, V., Russo, N., Hu, G., and Riordan, J. F., "Inhibition of Human Angiogenin by DNA Aptamers: Nuclear Colocalization of an Angiogenin-Inhibitor Complex", Biochemistry 1998, 37, 6857–6863). This DNA structure is a stem-loop structure that is nearly identical (in stem length and loop size) to the stem-loop effector that results in DNA-dependent ATP hydrolysis by the DNA-dependent ATPase (ADAAD) shown in Section 5.5.2, below. More specifically, the ADAAD effector shown in Section 5.5.2 has a 13 bp stem and a 12 nucleotide loop. The structure reported by Nobile et al., supra, to be recognized by angiogenin has a 13 bp stem and a 10 nucleotide loop. Consequently, the phosphoaminoglycoside preparations in accordance with the invention may be used to target angiogenin. The activity of angiogenin, which hydrolyzes RNA, and the ability of phosphoaminoglycoside compounds to inhibit its activity, can be measured by a ribonucleolytic assay or an angiogenesis assay, for example, as described in Nobile et al., supra, which is hereby incorporated by reference in its entirety.

Tables 2 and 3, below, list a variety of DNA-dependent ATPases and the reported specific activity of each respective enzyme. This list of proteins also includes targets for therapeutic intervention, and these proteins may also be used, in accordance with the invention, to screen for phosphaminoglycoside inhibitors in the assays described in Section 5.5, below

TABLE 2

Prokaryotic DNA-dependent ATPases

| Name | Specific activity (µmol/min/mg) | Reference |
|---|---|---|
| E. coli I Helicase | 22.5 | (1) |
| E. coli II Helicase | 10 | (23) |
| E. coli III Helicase | 30 | (35;36) |
| E. coli IV Helicase | 70 | (32) |
| E. coli Rep | 361 | (19) |
| E. coli DnaB | 10 | (2) |
| Gene12 protein from phage 22 | 3.2 | (31) |
| E. coli ATPase IV | 360 | (22) |
| E. coli PriA | 47.6 | (37) |
| Bacteriophage T4 gp44/62 | 0.2 | (16) |
| Bacteriophage T4 gp44/62 plus gp45 | 5.6 | (16) |

TABLE 3

Eukaryotic DNA-dependent ATPases

| Name | Specific activity (µmol/min/mg) | Reference |
|---|---|---|
| Yeast RAD3 | 0.25 | (27) |
| Yeast ATPase III | 0.007 | (26) |
| SV40 T antigen | 0.023 | (12) |
| Polyoma T antigen | 0.13 | (24) |
| FM3A ATPase B | 0.85 | (25) |
| FM3A ATPase $C_1$ | 1.03 | (34) |
| FM3A ATPase $C_3$ | 0.65 | (28) |
| Lily U-protein | 1.45 | (15) |
| Calf thymus DNA-dependent ATPase | 0.6 | (3) |
| ScHelI | 138 | (5) |
| DNA-dependent ATPase from HeLa cells | 0.86 | (6) |
| DNA-dependent ATPase from KB cells | 9.8 | (7) |
| HeLa cell DNA-dependent ATPase related to human Ku autoantigen | 1.64 | (9) |
| SV40 single-stranded DNA-dependent ATPase | 0.05 | (8) |
| KB DNA-dependent ATP phosphohydrolase | 1.7 | (11) |
| Mouse myeloma single-stranded DNA-dependent ATPase | 1.1 | (13) |
| DNA-dependent ATPase A (68-kDa) | 18 | (14) |
| DNA-dependent ATPase A (83-kDa) | 42 | (20) |
| DNA-dependent ATPase A (105-kDa) | 171 | (21) |
| RF-C | 0.04 | (18) |
| Novikoff rat hepatoma DNA-dependent ATPase IV | 9.2 | (30) |
| Novikoff rat hepatoma DNA-dependent ATPase III | 0.012 | (29) |
| Rat mitochondrial DNA-dependent ATPase | 0.007 | (33) |
| Mot1 | 0.33 | (4) |
| SWI/SNF complex | 0.06 | (10) |
| Snf2 | 0.02 | (17) |

The following list sets forth the citations for the references indicated in Tables 2 and 3, above.

1. Abdel-Monem, M. and H. Hoffman-Berling. 1976. Enzymic Unwinding of DNA. Eur.J.Biochem. 65:431–440.
2. Arai, N., A. Yasui, and A. Kornberg. 1997. Mechanism of dnaB Protein Action. J.Biol.Chem. 256:5247–5252.
3. Assairi, L. M. and I. R. Johnston . 1979. A DNA-Dependent ATPase of Calf-Thymus. Eur.J.Biochem. 99:71–79.
4. Auble, D. T., K. E. Hansen, C. G. Mueller, W. S. Lane, J. Thorner, and S. Hahn. 1994. Mot1, a global repressor of RNA polymerase II transcription, inhibits TBP binding to DNA by an ATP-dependent mechanism. Genes Dev. 8:1920–1934.
5. Bean, D. W., W. E. Kallam, Jr., and S. W. Matson. 1993. Purification and characterization of a DNA helicase from *Saccharomyces cerevisiae*. J.Biol.Chem. 268:21783–21790.
6. Biamonti, G., F. Cobianchi, A. Falaschi, and S. Riva. 1983. Total Purification of a DNA-dependent ATPase and of a DNA-Binding Protein from Human Cells. EMBO J. 2:161–165.
7. Boxer, L. M. and D. Korn. 1980. Structural and Enzymological Characterization of a Deoxyribonucleic Acid Dependent Adenosine Triphosphatase from KB Cell Nuclei. Biochemistry 19:2623–2633.
8. Brewer, B. J., S. R. Martin, and J. J. Champoux. 1983. A Cellular Single-Stranded DNA-dependent ATPase Associated with Simian Virus 40 Chromatin. J.Biol.Chem. 258:4496–4502.
9. Cao, Q. P., S. Pitt, J. Leszyk, and E. F. Baril. 1994. DNA-dependent ATPase from HeLa cells is related to human Ku autoantigen. Biochemistry 33:8548–8557.
10. Cote, J., J. Quinn, J. L. Workman, and C. L. Peterson. 1994. Stimulation of GAL4 derivative binding to nucleosomal DNA by the yeast SWI/SNF complex. *Science* 265:53–60.
11. deJong, P. J., J. P. M. Tommassen, P. C. van der Vliet, and H. S. Jansz. 1981. Purification and Characterization of DNA-dependent ATP Phosphohydrolases from KB Cells. Eur.J.Biochem. 117:179–186.
12. Giacherio, D. and L. P. Hagar. 1979. A Poly(dT)-stimulated ATPase Activity Associated with Simian Virus 40 Large T Antigen. J.Biol.Chem. 254:8113–8116.
13. Hachmann, H. J. and A. G. Lezius . 1976. An ATPase-depending on the Presence of Single-Stranded DNA From Mouse Myeloma. Eur.J.Biochem. 61:325–330.
14. Hockensmith, J. W., A. F. Wahl, S. Kowalski, and R. A. Bambara. 1986. Purification of a Calf Thymus DNA-Dependent Adenosinetriphosphatase That Prefers a Primer-Template Junction Effector. Biochemistry 25:7812–7821.
15. Hotta, Y. and H. Stern. 1978. DNA Unwinding Protein From Meiotic Cells of Lilium. Biochemistry 17:1872–1880.
16. Jarvis, T. C., L. S. Paul, J. W. Hockensmith, and P. H. von Hippel. 1989. Structural and Enzymatic Studies of the T4 DNA Replication System II. ATPase Properties of the Polymerase Accessory Protein Complex. J.Biol.Chem. 264:12717–12729.
17. Laurent, B. C., I. Treich, and M. Carlson. 1993. The yeast SNF2/SW12 protein has DNA-stimulated ATPase activity required for transcriptional activation. Genes Dev. 7:583–591.
18. Li, X. and P. M. J. Burgers. 1994. Molecular Cloning and Expression of the *Saccharomyces cerevisiae* RFC3 Gene, an Essential Component of Replication Factor C. Proc. .Natl.Acad.Sci.U.S.A. 91:868–872.
19. Lohman, T. M., K. Chao, J. M. Green, S. Sage, and G. T. Runyon. 1989. Large-scale Purification and Characterization of the *Escherichia coli* rep Gene Product. J.Biol.Chem. 264:10139–10147.

20. Mesner, L. D., W. M. Sutherland, and J. W. Hockensmith. 1991. DNA-Dependent Adenosinetriphosphatase A Is the Eukaryotic Analogue of the Bacteriophage T4 Gene 44 Protein: Immunological Identity of DNA Replication-Associated ATPases. Biochemistry 30:11490–11494.
21. Mesner, L. D., P. A. Truman, and J. W. Hockensmith. 1993. DNA-dependent adenosinetriphosphatase A: immunoaffinity purification and characterization of immunological reagents. Biochemistry 32:7772–7778.
22. Meyer, R. R., C. L. Brown, and D. C. Rein. 1984. A New DNA-dependent ATPase from *Escherichia coli*. J.Biol.Chem. 259:5093–5099.
23. Richet, E. and M. Kohiyama. 1976. Purification and Characterization of a DNA-dependent ATPase from *E. coli*. J.Biol.Chem. 251:808–812.
24. Seki, M., T. Enomoto, T. Eki, A. Miyajima, Y. Murakami, F. Hanaoka, and M. Ui. 1990. DNA Helicase and Nucleoside-5'-triphosphatase Activities of Polyoma Virus Large Tumor Antigen. Biochemistry 29:1003–1009.
25. Seki, M., T. Enomoto, Y. Watanabe, Y. Tawaragi, K. Kawasaki, F. Hanaoka, and M. Yamada. 1986. Purification and Characterization of a Deoxyribonucleic Acid Dependent Adenosinetriphosphatase From Mouse FM3A Cells: Effects of Ribonucleoside Triphosphates on the Interaction of the Enzyme with Single-Stranded DNA. Biochemistry 25:3239–3245.
26. Sugino, A., B. H. Ryu, T. Sugina, L. Naumovski, and E. C. Friedberg. 1986. A New DNA-dependent ATPase Which Stimulates Yeast DNA Polymerase I and has DNA-unwinding Activity. J.Biol.Chem. 261:11744–11750.
27. Sung, P., L. Prakash, S. Weber, and S. Prakash. 1987. The RAD3 gene of *Saccharomyces cerevisiae* encodes a DNA-dependent ATPase. Proc.Natl.Acad.Sci.U.S.A. 84:6045–6049.
28. Tawaragi, Y., T. Enomoto, Y. Watanabe, F. Hanaoka, and M. Yamada. 1984. Multiple Deoxyribonucleic Acid Dependent Adenosinetriphosphatases in FM3A Cells. Characterization of an Adenosinetriphosphatase that Prefers Poly[d(A-T)] as Cofactor. Biochemistry 23:529–533.
29. Thomas, D. C. and R. R. Meyer. 1982. DNA-dependent ATPases from the Novikoff Hepatoma. Characterization of a Homogeneous ATPase Which Stimulates DNA Polymerase-beta. Biochemistry 21:5060–5068.
30. Thomas, D. C., D. C. Rein, and R. R. Meyer. 1988. Purification and Enzymological Characterization of DNA-dependent ATPase IV from the Novikoff Hepatoma. Nucleic Acids Res. 16:6447–6464.
31. Wickner, S. 1984. DNA-dependent ATPase Activity Associated with Phage P22 Gene 12 Protein. J.Biol.Chem. 259:14038–14043.
32. Wood, E. R. and S. W. Matson. 1987. Purification and Characterization of a New DNA-dependent ATPase with Helicase Activity from *Escherichia coli*. J.Biol.Chem. 262:15269–15276.
33. Yaginuma, K. and K. Koike. 1981. Properties of a DNA-dependent ATPase From Rat Mitochondria. Nucleic Acids Res. 9:1949–1961.
34. Yanagisawa, J., M. Seki, T. Kohda, T. Enomoto, and M. Ui. 1992. DNA-dependent Adenosinetriphosphatase C1 from Mouse FM3A Cells Has DNA Helicase Activity. J.Biol.Chem. 267:3644–3649.
35. Yarranton, G. T., R. H. Das, and M. L. Gefter. 1979a. Enzyme-Catalyzed DNA Unwinding: A DNA-dependent ATPase from *E. coli*. J.Biol.Chem. 254:11997–12001.
36. Yarranton, G. T., R. H. Das, and M. L. Gefter. 1979b. Enzyme-Catalyzed DNA Unwinding: Mechanism of Action of Helicase III. J.Biol.Chem. 254:12002–12006.
37. Zavitz, K. H. and K. J. Marians. 1997. Helicase-deficient Cysteine to Glycine Substitution Mutants of Escherichia coli Replication Protein PriA Retain Single-Stranded DNA-dependent ATPase Activity. J Biol Chem 268:4337–4346.

5.4. Inhibitors of DNA-dependent ATPase Activity

Compounds that inhibit nucleic acid-dependent ATPase activity can be identified, in accordance with the invention, using the screening assays described in Section 5.5, for example. Such inhibitory compounds are useful in the prevention and treatment of disease through the disruption of nucleic acid metabolism and the induction of apoptosis.

One class of such inhibitory compounds are phosphoaminoglycosides. Phosphoaminoglycosides occur naturally as products of bacterial resistance to the aminoglycoside antibiotics. The experiments described in detail in the Example in Sections 13, below, demonstrate the first chemotherapeutic use for these compounds. Furthermore, such useful inhibitory compounds also include non-naturally occurring phosphoaminoglycoside derivatives.

5.4.1. Phosphoaminoglycosides and Derivatives

Phosphoaminoglycosides and their derivatives that can be screened for specific inhibitory activity and used therapeutically to disrupt nucleic acid metabolism include, but are not limited to, the 3' or 5" phosphorylatable compounds described herein below.

The following aminoglycoside compositions were prepared, in accordance with the invention, as described in the Example in Section 8.1, below, and their respective Ki's in the presence of effector were determined.

Amikacin (Also known as BB-K8)
Butirosin A & B (~15% Butirosin B)
Geneticin
Gentamicin A
Kanamycin A & B (~5% Kanamycin B)
Lividomycin A
Neomycin B & C (~15% Neomycin C)
Paromomycin I & II

TABLE 4

Ki determined for phosphoaminoglycosides

| Aminoglycoside | derivative | Ki (nM) | modified position |
|---|---|---|---|
| Amikacin | 3' phosphorylated amikacin | 167 | 3'OH |
| Butirosin | 3' and 5"phosphorylated butirosin | 180 | 3'OH and 5"OH |
| Geneticin (G418) | 3' phosphorylated geneticin | 191 | 3'OH |
| Gentamicin | 3' phosphorylated gentamicin | 219 | 3'OH |
| Kanamycin | 3' phosphorylated kanamycin | 580 | 3'OH |
| Lividomycin | 5" phosphorylated lividomycin | 27 | 5"OH |
| Neomycin | 3' and 5" phosphorylated neomycin | 11 | 3'OH and 5"OH |
| Paromomycin | 3' and 5" phosphorylated paromomycin | 250 | 3'OH and 5"OH |

The structural formulae of these aminoglycosides are depicted as follows:

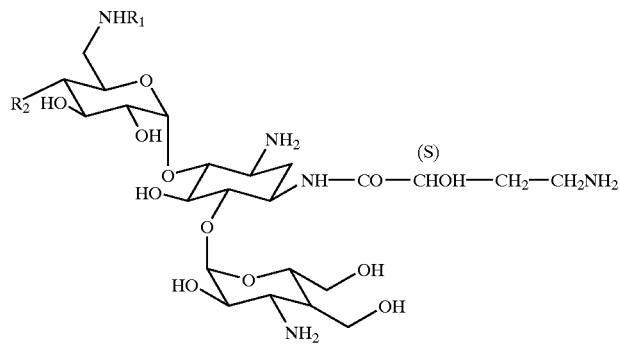
|  | $R_1$ | $R_2$ |
|---|---|---|
| 6'-N-Methylamikacin | —CH$_3$ | —OH |
| 4'-Deoxy-6'-N-Methylamikacin | —CH$_3$ | —H |
| Amikacin | —H | —OH |
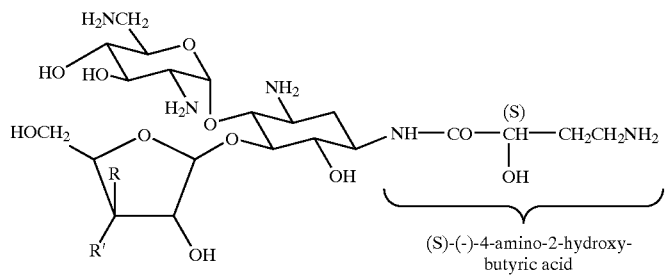
74 Buticasin A  R = OH, R' = H
75 Buticasin B  R = H, R' = OH
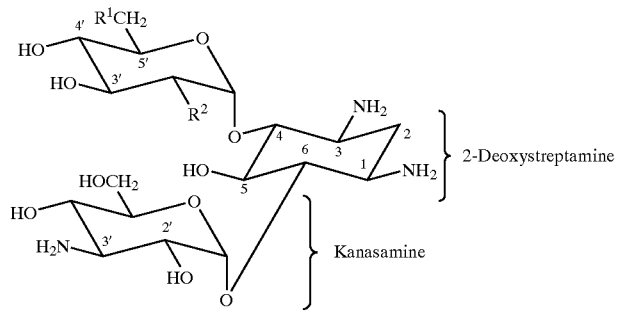
24 Kanamycin A  $R^1 = NH_2$, $R^2 = OH$
25 Kanamycin B  $R^1 = NH_2$, $R^2 = NH_2$
26 Kanamycin C  $R^1 = OH$, $R^2 = NH_2$
Nearamine C
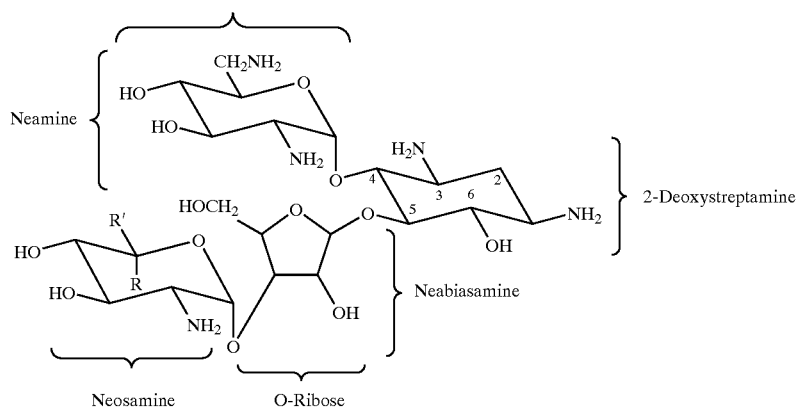
10 Neomycin B  R = CH$_2$NH$_2$, R' = H
11 Neomycin C  R = H, R' = CH$_2$NH$_2$ -continued
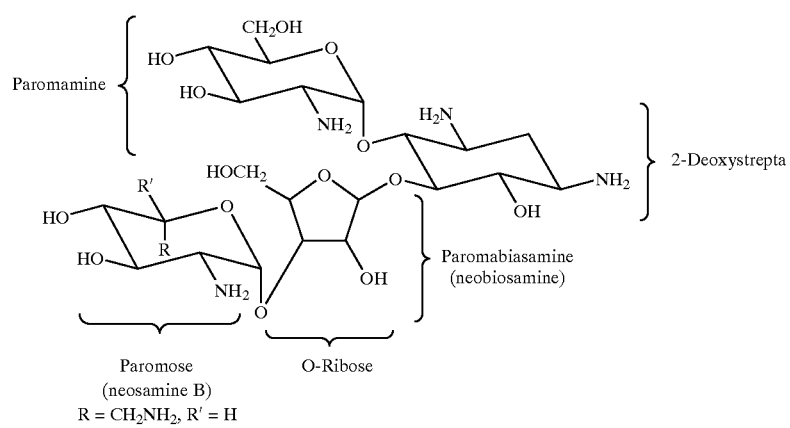
13 Paromomycin I R = CH₂NH₂, R' = H
14 Paromomycin II R = H, R' = CH₂NH₂
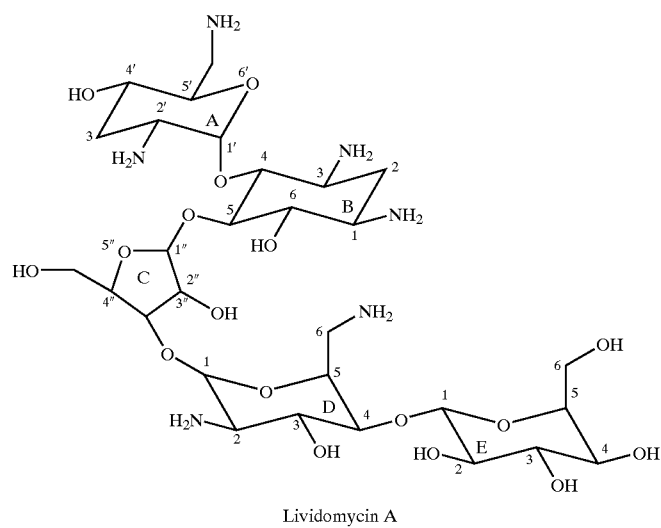
Lividomycin A
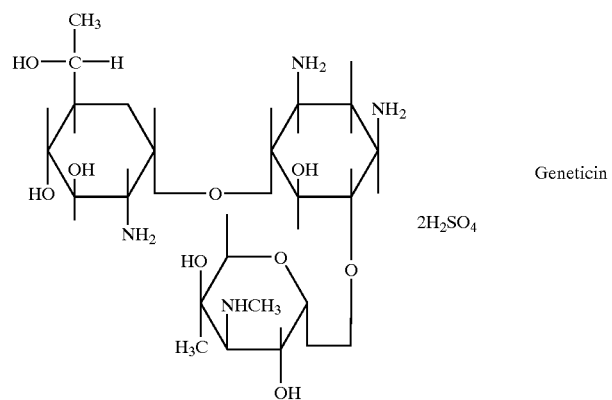
Geneticin
2H₂SO₄

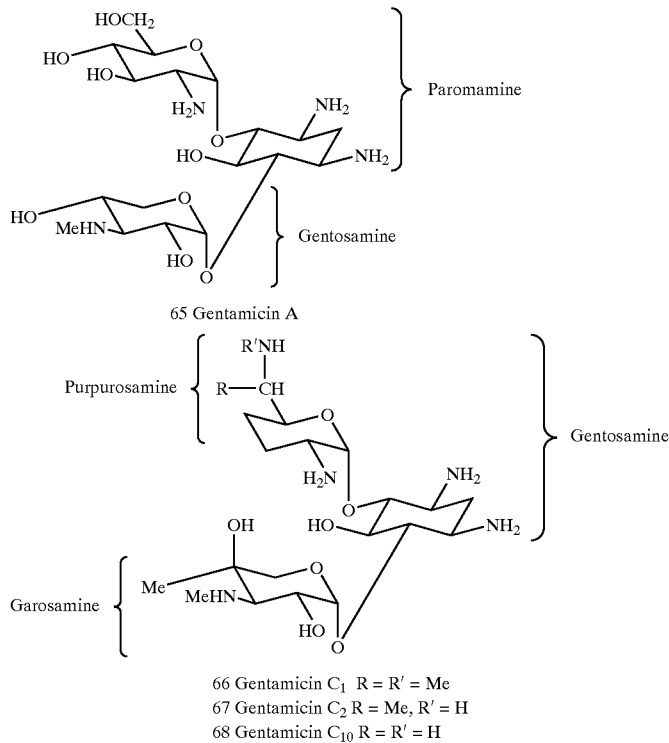

66 Gentamicin C₁ R = R' = Me
67 Gentamicin C₂ R = Me, R' = H
68 Gentamicin C₁₀ R = R' = H Phosphorylated preparations of aminoglycosides in Table 4, prepared in accordance with the methods described in the Example in Section 8.1, below, have been demonstrated to inhibit DNA-dependent ATPase activity.

The following aminoglycosides, which have 3' or 5" positions available for phosphorylation, can be phosphorylated using the methods disclosed in Sections 5.4.2 and 8.1, below.

6'-N-Methylamikacin
4'-Deoxy-6'N-Methylamikacin
Butikacin (Also known as Butakacin)
5"-Amino-5"-Deoxybutirosin A
1-N-HAPA-Gentamicin B (Also known as SCH 21420)
SCH 20287
SCH 23722
SCH 24443
SCH 21211
SCH 21768
JI 20 A
X₂
Gentamicin B
Hybrimycin A1
Hybrimycin A2
Hybrimycin B1
Hybrimycin B2
Kanamycin C
NK-1001
NK1012-1
4,6-di-O-(6-amino-6-deoxy-α-D-glucopyranosyl)-2-deoxystreptamine
4-O-(6-amino-6-deoxy-α-D-glucopyranosyl)-6-O-(α-D-glucopyranosyl)-2-deoxystreptamine
6'-N-methylkanamycin
6"-Chloro-6"-deoxykanamycin
6"-Deoxykanamycin A
Kanamycin-6"-uronic acid
Kanamycin-6"-phosphate
6"-Amino-6"-deoxykanamycin
6"-Hydrazino-6"-deoxykanamycin
Tetrakis-N-(p-chlorobenzyl)kanamycin
4",6"-O-benzylidenekanamycin
2"-manno-kanamycin
6"-amino-6"-deoxy-2"-manno-kannamycin
6"-deoxy-6"-hydrazino-2"-manno-kanamycin
Lividomycin B
Neomycin A (Also known as Neamine)
Propikacin (Also known as UK 31214)
Ribostamycin
Ribostamycin-5"-uronic acid
Seldomycin 5
3-N-Acetylseldomycin 5
3'-Episeldomycin 5
6'-N-Methylseldomycin 5
1-N-HABA-Seldomycin 5
1-N-Ethylseldomycin 5
Trehalosamine
α-D-mannosyl-α-D-glucosaminide Additional aminoglycosides which may be phosphorylated in accordance with the invention are:

Apramycin (Also known as Nebramycin)
Bluensomycin (Also known as Glebomycin)
Gentamicin C₁
Gentamicin C₂
Gentamicin C₁ₐ
Gentamicin C₂ᵦ (Also known as Sagamicin)
SCH 23200
SCH 23456
3',4'-unsaturated kanamycin B
3',4'-dideoxy-6'-N-methylkanamycin B
3'-amino-3'-deoxy-2'-manno-kanamycin
3'-amino-3'-deoxykanamycin
Netromycin (Also known as netilmicin)

3',4'-dideoxyribostamycin
3',4',5''-trideoxyribostamycin
3'-Deoxyseldomycin 5
Streptomycin
Dihydrostreptomycin
Dihydrodeoxystreptomycin
Hydroxystreptomycin
N-demethylstreptomycin
Mannosidostreptomycin
Tobramycin (Also known as nebramycin factor 6)
Sisomicin
G-52 (Also known as 6'-N-methylsisomicin)
Verdamicin (Also known as 6'-C-methylsisomicin)
Destomycin A
Antibiotic A-396-I
Dibekacin
HABA-dibekacin
HABA-methyldibekacin
Kasugamycin
Fortimicin A
5-episisomicin (Also known as SCH 22591)

The invention further contemplates the use of catabolic products of phosphoaminoglycosides containing four or five glycosidic rings, including but not limited to those four-ringed or five-ringed compounds described in this section, above, in which one or two of the rings has been removed to yield a three-ringed phosphoaminoglycoside derivative. For example, and not by way of limitation, four-ringed phosphoaminoglycosides such as phosphoneomycin can be chemically degraded to yield a three-ringed derivative having greater inhibitory activity. Furthermore, such three-ringed derivatives may have greater rates of cellular uptake based on their smaller size, further increasing their effectiveness. Such derivative compounds can be readily prepared using methods well known in the art. For example, the parent phosphoaminoglycoside can be degraded using alkali and then isolated using cation exchange, gel exclusion, or molecular sieve HPLC to resolve species having a molecular weight in the range of 0 to 1000 Daltons.

In addition, the permeability of the phosphoaminoglycosides into intact cells can be enhanced by modification of the phosphate groups to esterified forms. Such esterification can be accomplished by the methodology of Schultz et al. (Schultz, C., Vajanaphanich, M., Harootunian, A. T., Sammak, P. J., Barrett, K. E., and Tsien, R. Y., "Acetoxymethyl Esters of Phospates, Enhancement of the Permeability and Potency of cAMP", J. Biol. Chem. 1993, 268, 6316–6322, which is hereby incorporated by reference in its entirety). The ester bonds are automatically hydrolyzed upon uptake into cells to release the phosphoaminoglycoside precursor.

The compounds described in this Section, above, may be assayed for inhibitory activity in accordance with the methods described in Section 5.5, below.

5.4.2. Production of Phosphoaminoglycosides

Phosphorylation of aminoglycosides is carried out, in accordance with the invention, using aminoglycoside phosphotransferase enzymes, including but not limited to aminoglycoside phosphotransferase type III (APH(3')-IIIa). As described in the Example in Section 8.1, below, APH(3')-IIIa was overproduced and purified. The enzyme is combined with ATP and the aminoglycoside in vitro in a reaction which yields 3'-phosphoaminoglycoside.

The product can then be purified using standard techniques, including but not limited to either metal chelate chromatography or BioRad BioRex 70 chromatography. Either chromatographic method yields aminoglycoside free of phosphoaminoglycoside or phosphoaminoglycoside free of aminoglycoside.

The phosphorylated compositions may then be assayed for inhibitory activity in accordance with the methods described in Section 5.5, below.

5.4.3. Production of Toxicity-Free Antibiotics

The method for purifying phosphoaminoglycosides from the aminoglycoside starting material described in Section 5.4.2, above, is also useful in purifying aminoglycosides for use, e.g., as antibiotics. Aminoglycosides are generally derived from biological sources (fungi) and are known to disrupt translation in prokaryotes. The aminoglycosides are also known to be both ototoxic and nephrotoxic in eukaryotes but the mechanism of toxicity is unknown. It is noteworthy that acceptable commercial pharmaceutical preparations of kanamycin and neomycin may have only 75% kanamycin (i.e., 25% impurities) (USP D1 Volume III: Approved Drug Products and Legal Requirements, 1997, 17th Edition, pp. 278–279, Rand McNally, Massachusetts). Similarly, compositions of neomycin having only 60% neomycin have been found acceptable (Id., at page 340).

Since the potency of the phosphoaminoglycosides towards DNA-dependent ATPase A is approximately 1000-fold higher than the parent compound, the presence of aminoglycoside phosphotransferases in fungi could result in small contaminants of phosphoaminoglycosides in commercial aminoglycoside preparations and the phosphorylated derivatives could actually account for the eukaryotic toxicity. Thus, removal of the phosphoaminoglycosides from preparations of the aminoglycosides used to treat patients can result in reduced toxicity and hence allow these compounds to be used more efficaciously.

5.5. Screening Assays

Compounds, such as the compounds described in Section 5.4, above, or other test compounds, are screened, in accordance with the invention, for ability to inhibit nucleic acid-dependent ATPase activity. Different assaying formats well known in the art can be used to screen for inhibitory activity. Such assays systems include, but are not limited to, the assays described in the following sub-sections, below.

5.5.1. Assays for Inhibitors of DNA-dependent ATPase Activity 5.5.1.1. Biochemical Assays Colorimetric, spectrophotometric, and radioactive assays for ATP hydrolysis are well known in the art (Hockensmith, J. W., et al., 1986, Biochemistry 25:7812–7821; Jarvis, T. C., et al, 1989, J.Biol.Chem. 264:12717–12729). These methods can be applied to assay for nucleic acid-dependent ATPase activity, in accordance with the invention. Colorimetric, spectrophotometric, and radioactive assays for ATP hydrolysis assay for DNA-dependent ATPase A, for example, are described in detail in the Example in Section 7.3, below.

As an alternative to measuring ATP hydrolysis, inhibitors of ATPase activity can be screened using a gel shift assay. Such assays are well known in the art for detecting the disruption of specific protein:DNA complexes. For example, a gel shift assay for the MOT1:TBP:DNA complex is described in Auble, D. T., et al., 1994, *Genes Dev.* 8:1920–1934, which is hereby incorporated by reference in its entirety. In accordance with the invention, phosphoaminoglycoside inhibitors of DNA-dependent ATPase activity have been shown to disrupt the MOT1:TBP:DNA complex.

Compounds that inhibit nucleic acid-dependent ATPase activity have been shown, in accordance with the invention, to also inhibit DNA-dependent protein kinase activity. Thus, compounds that inhibit nucleic acid dependent ATPase activity can be screened using the assay described in Chan, D. W. and S. P. Lees-Miller. 1996. The DNA-dependent protein kinase is inactivated by autophosphorylation of the catalytic subunit. *Journal of Biological Chemistry* 271:8936–8941. DNA-dependent protein kinase uses DNA effectors for protein kinase activity (Morozov, V. E., M. Falzon, C. W. Anderson, and E. L. Kuff. 1994. DNA-dependent protein kinase is activated by nicks and larger single-stranded gaps. *Journal of Biological Chemistry* 269:16684–16688).

The invention includes test kits for monitoring the presence of phosphoaminoglycosides in body fluid samples of patients undergoing treatment. Rapid test kits can be prepared, for example, as paper strips. For instance, the blood levels of phosphoaminoglycosides will be difficult to monitor since the drugs do not have distinguishing characteristics such as UV absorbance. A simple colorimetric test strip using inhibition of ATP hydrolysis by one of the fragments of DNA-dependent ATPase A could provide a rapid test kit of general utility in a clinical setting. The 68 kDa polypeptide fragment of DNA-dependent ATPase A, for example, is very stable and, therefore, particularly well-suited for use in such an assay kit.

5.5.1.2. Cell and Animal Based Assays

In accordance with the invention, inhibitory compounds can be tested for activity in cellular and animal systems. For example, cultures of tumor cells, target microbial pathogens, or cells infected with target viruses can be analyzed for the ability of test compounds to inhibit cell growth or viral infection. The Examples in Sections 11 and 12, below, describe cell-based assays for inhibition of growth of prostate and breast cancer cell lines, respectively. The Examples in Sections 14 and 15, below, describe cell-based assays for the inhibition of growth of the protozoans amoeba and Leishmania, respectively. The Examples in Sections 10 and 16 describe cell-based assays for inhibition of DNA synthesis and DNA repair, respectively. The Example in Section 13, below, illustrates an animal system for assaying the effect of test compounds on tumor growth.

These assays can be employed to screen for compounds that produce the respective inhibitory effect. The principles illustrated in these Examples can be readily adapted, in accordance with the invention, for testing the ability of test compounds such as the phosphoaminoglycosides disclosed herein to inhibit the a given target metabolic function, or the growth of a given pathogen or other organism or a given cell-type (such as macrophages or cancer cells).

5.5.2. Effector Preference of DNA-Dependent ATPase A

A novel understanding of the role of DNA effectors in DNA-dependent ATPase A function is provided herein. DNA-dependent ATPase A hydrolyzes ATP only in the presence of DNA. DNA-dependent ATPase A shows specificity with respect to the DNA effector. However, the interaction between DNA-dependent ATPase A and DNA is not dependent upon the sequence of the DNA. The interaction appears to be solely dependent upon the structure of the DNA effector. Thus, the enzyme is maximally active only in the presence of a DNA molecule possessing a double-stranded to single-stranded transition region. DNA molecules lacking this structure do not effect ATP hydrolysis by DNA-dependent ATPase A. In addition to the double-stranded to single-stranted transition region, the results detailed below also demonstrate that the presence of a hydroxyl group at the 3' position enhances the interaction between DNA-dependent ATPase A and DNA.

In a preferred embodiment for screening assays for inhibitors of DNA-dependent ATPase A, the double-stranded region of the DNA molecule should be longer that 11 base-pairs and the single-stranded region of the DNA molecule longer that 8 bases. DNA molecules containing double-stranded and single-stranded regions smaller than the above specified criteria can function as an effector of DNA-dependent ATPase A; however, the interaction between the enzyme and the DNA does not lead to optimal ATP hydrolysis.

The following list and examples of DNA effectors for DNA-dependent ATPase A and ADAAD. These effectors are examples to structural types of effectors. The particular nucleotide sequence is in no way limiting. The structural types are listed in the order of most effective to least effective. Preferably, the effectors have a double-strand to single-strand transition and a 3'-hydroxyl end. The addition of a 3'-phosphate to the end of any effector will reduce its effectiveness.

(SEQ ID NO: 1)
1) Stem-loop
```
                    CGACG
    GCGCAATTGCGCT          A
    CGCGTTAACGCGA          T
                    TTTTT
```

Preferably, stem-loop DNA effectors have loops containing at least three bases. More preferably, the loops contain greater than eight bases, with twelve bases most preferable. Preferably, stem-loop DNAs with loops smaller than 12 bases should have the stem closed with an A-T base pair. Stem-loop DNA effectors with double-stranded stems of 13 base pairs are preferable, with stems of 11 base pairs being less preferred.

2) Mismatch
CCCCCCCCCCCCCCCTCGATGTCGACTCGAGTC (SEQ ID NO:2)
GGGGGGGGGGTTTTTTTTTTCAGCTGAGCTCAG (SEQ ID NO:3)

3) Recessed 3'-ends
5'CCCCCCCCCCCCCCCCTCGATGTCGACTCGAGTC (SEQ ID NO:2)-3'
3'-CTGAGCTCAGCTGTA (SEQ ID NO:4)----------5'

4) AT-rich duplex
AGCTTTACCTCTCCTCTATAAGAATTCGAGC
TCGAAATGGAGAGGAGATATTCTTAAGCTCG 5) Single-stranded
GCTCGAATTCTTATAGAGGAGAGGTAAAGCT (SEQ ID NO:6)

6) Recessed 5'-hydroxyl ends
3'------CAGCTGAGCTCAG (SEQ ID NO: 7)-5'
5'-GACTCGAGTCGACATCGAGGGGGGGGGGGG GG (SEQ ID NO:8)-3'

7) Duplex (SEQ ID NO:9)
GCGCAATTGCGC
CGCGTTAACGCG 5.5.3. Assays for Effectors and Inhibitory Effector Analogs DNA-dependent ATPase A can be used to screen DNA, such as oligonucleotides, for the presence of secondary structure. For example, oligonucleotides are used as antisense or ribozyme molecules. The presence of secondary structure in these molecules would inhibit or eliminate their effectiveness. Such secondary structures may form intermolecularly (self-complementarity), or intramolecularly (snap-back). In addition, oligonucleotides used, for example, in the polymerase chain reaction yield less amplification if they form secondary structures. Computer analyses used to predict such secondary structures are often unreliable.

The presence of such secondary structures can be definitively assayed, in accordance with the invention, by testing the ability of the oligonucleotides to act as effectors of nucleic acid-dependent ATPase activity. For example, and not by way of limitation, a test oligonucleotide can added to an assay for DNA-dependent ATPase activity using any of the biochemical assays described in Section 5.5.1, above. The ability of the oligonucleotide to act as an effector of the ATPase and yield hydrolysis of ATP indicates the presence of secondary structure in the oligonucleotide.

5.6. Methods of Treatment

In accordance with the invention, pharmacotherapeutic uses of phosphoaminoglycosides include the disruption of nucleic acid metabolism in any cellular system in which arresting cellular growth or induction of apoptosis is desired. Thus, the compounds can be administered to arrest cell growth in humans, other animals, insects, plants, as well as microbes.

5.6.1. Cancer

The nucleic acid-dependent ATPase inhibitors are used, in accordance with the invention, to treat and prevent cancer. These compounds, which include, but are not limited to, phosphoaminoglycosides, target proteins and not DNA as is common with many chemotherapeutic agents. Inhibition of the enzymes involved in DNA repair using aminoglycoside derivatives should increase the efficacy of chemotherapeutic agents which induce DNA damage.

Phosphoaminoglycosides are a natural product of aminoglycoside-resistant bacteria and have not been shown to lead to mutagenesis in bacteria. A number of commercial products for overexpression of proteins rely on aminoglycoside resistance via phosphorylation. Expression of proteins in these systems is common and mutagenesis of those proteins or the transformed cell line has not been reported.

The Example in Section 13, below, demonstrates the use of phosphoaminoglycosides to successfully treat cancer in mice. The tumor cells were killed in response to administered phosphokanamycin.

The types of cancer that can be treated in accordance with the invention include, but are not limited to, sarcoma or carcinoma, such as prostate cancer, breast cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenström's macroglobulinemia, and heavy chain disease.

5.6.2. Infectious Disease

Parasitic infections, in which arresting parasitic cell growth or replication of parasitic genetic material is desired, are treated or prevented in accordance with the invention by administration of nucleic acid-dependent ATPase inhibitors.

The Example in Section 14, below, demonstrates the use of phosphoaminoglycosides to kill amoebae. The Example in Section 15, below, demonstrates the use of phosphoaminoglycosides to kill Leishmania.

Phosphoaminoglycosides can also be used in combination with other drugs that are useful in inhibiting infection. For example, in infections such as malaria, phosphoaminoglycosides can be used to target the parasite before it invades the erythrocytes or as the parasite is released following rupture of the erythrocyte, while other drugs (e.g. chloroquine, quinine) serve to eliminate the parasite from the infected cells.

Indeed, phosphoaminoglycosides can be used to treat the environment, as well as infected individuals. For parasite eradication (e.g. protozoa, nematodes, etc.). As natural products, phosphoaminoglycosides are particularly useful since there are metabolic enzymes in some organisms that can lead to dephosphorylation. Consequently, long term environmental toxicity is minimized.

5.6.2.1. Fungal Infections

Fungi produce aminoglycosides and have been documented to survive in the presence of enzymes which produce phosphoaminoglycosides. Compounds or enzymes which break down the cell wall of the fungi (e.g., chitinase) can permit the phosphoaminoglycosides to enter the cells and thus result in cell death to the fungi.

5.6.2.2. Bacterial Infections

Prokaryotic cells are susceptible to cell killing by aminoglycosides, presumably because the aminoglycosides disrupt translation by binding to the RNA of the ribosomal subunits. This binding is disrupted in vitro by phosphorylation of the aminoglycoside and phosphoaminoglycosides have not been suspected of having a prokaryotic target simply because they are a product of prokaryotic "resistance" genes. Experiments detailed below (see FIG. 6) demonstrate that phosphoaminoglycosides have potential targets within the prokaryotic cell (DNA helicases, polymerase accessory proteins, etc.). These targets are not usually important since the phosphoaminoglycoside normally cannot reach them. This may be the result of compartmentalization. The aminoglycoside phosphotransferases are believed to reside in the periplasmic space where they intercept the aminoglycoside and phosphorylate the drug. The phosphorylation event is believed to block transport into the cell, resulting in compartmentalization in the periplasmic space. Agents which disrupt the cell wall/periplasmic space (such as penicillin derivatives) may provide increased entry of the phosphoaminoglycosides into the cell and thus target DNA metabolic processes which have not been previously targeted. Thus, this synergistic effect provides a new antibacterial regimen for treatment of aminoglycoside resistant organisms. This is potentially a very important observation since drugs such as penicillins act on prokaryotic cells and not eukaryotic cells, therefore adding a measure of specificity to the use of these drugs.

Penicillins have been used extensively with aminoglycoside antibiotics to yield synergistic toxicity for prokaryotic organisms. The proposed mechanism of the synergy has not included the possibility of phosphoaminoglycoside contamination of the aminoglycoside preparation. Since the phosphoaminoglycosides are one thousand times more potent than the aminoglycosides, administration of the phosphoaminoglycosides that are free of the parent aminoglycoside would result in decreased systemic loads of these drugs and therefore potentially reduced toxicity.

5.6.2.3. Viral Targeting

Viruses have only a limited amount of nucleic acid in their genome and thus frequently exploit the intracellular machinery of their eukaryotic host cells. Any viruses dependent on host cell DNA-dependent ATPase function are likely to be susceptible to the phosphoaminoglycosides during phases where they engage in DNA metabolic processes. For example, HIV infected macrophages are an ideal example since the macrophage would uptake the phosphoaminoglycoside by its normal endocytotic processes and thus disrupt normal cellular DNA metabolic processes essential for maintenance of the virus.

5.6.2.4. Protozoan Targets

The following tables list the target infectious diseases which can be treated or prevented through administration of phosphoaminoglycoside preparations in accordance with the invention.

TABLE 5

Protozoan infections in humans

| ORGANISM | DISEASE |
|---|---|
| Plasmodium sp. Includes | |
| Plasmodium falciparum | Malaria |
| Plasmodium vivax | |
| Plasmodium malariae | |
| Plasmodium ovale | |
| Entamoeba histolytica | Amebic dysentery |
| Trypanosoma sp. Includes | |
| Trypanosoma brucei sp. | Trypanosomiases |
| Trypanosoma cruzi | (Chagas disease) |
| Leishmania sp. Includes | |
| Leishmania chagasi | Leishmaniasis |
| Leishmania donovani | |
| Leishmania tropica | |
| Leishmania major | |
| Leishmania aethiopica | |
| Leishmania mexicana | |
| Leishmania braziliensis | |
| Toxoplasma gondii | Toxoplasmosis |
| Giardia lambia | Giardiasis |
| Balantidium coli | Dysentry |
| Trichomonas vaginalis | Human trichomoniasis |
| Babesia bigemina | Babesiosis |
| Cryptosporidium parvum | Cryptosporidiosis |

TABLE 6

Target Protozoan diseases in animals

| ORGANISM | Principal host | DISEASE |
|---|---|---|
| Trypanosoma equiperdum | Equines | Dourine |
| Trypanosoma evansi | Various domestic animals | Surra |
| Trypanosoma brucei | Bovines, equines, porcines, camels, canines | Nagana |
| Typanosoma congolense | Bovines and other domestic mammalians | Bovine trypanosomiasis |
| Trichomonas gallinae | Avians | Avian trichomoniasis |
| Tritrichomonas foetus | Cattle | Tritrichomonas abortion |
| Histomonas meleagridis | Avians | Blackhead enterohepatitis |
| Nosema bombycis | Silkworms | Pebrine disease of silkworm |
| Nosema apis | Bees | Nosema disease of bees |
| Glugea hertwigi | Various freshwater and marine fish | Microsporidiosis of fish |
| Glugea mulleri | | |
| Babesia caballi | Equines | Equine piroplasmosis |
| Babesia equi | | |

TABLE 6-continued

Target Protozoan diseases in animals

| ORGANISM | Principal host | DISEASE |
|---|---|---|
| Eimeria tenella | Domestic poultry | |
| Eimeria averculina | | |
| Eimeria bovis | Bovines | Coccidiosis |
| Eimeria zurnii | | |
| Theileria parva | Cattle | East Coast Fever |
| Pfiesteria piscicida | Fish | |

TABLE 7

Nematode infections of man

| ORGANISM | DISEASE |
|---|---|
| Ascaris lumbricoides | Human ascaridiasis |
| Enterobius vermicularis | Pinworm infections |
| Trichuris trichiura | Human trichuriasis |
| Ancylcostoma duodenale | Human ancylcostomiasis |
| Necator americanus | |
| Wuchereria bancrofti | Filariasis |
| Brugia malayi | |
| Onchocerca volvulus | Ocnchocerciasis |

TABLE 8

Nematode infections in animals

| ORGANISM | Principal hosts | DISEASE |
|---|---|---|
| Ascaris suis | Porcines | Porcine ascariasis |
| Parascaris equorum | Equines | Equine parascariasis |
| Trichuris discolor | Cattle | Bovine trichuriasis |
| Trichuris suis | Pigs | Porcine trichuriasis |
| Trichuris ovis | Cattle, sheep | Trichuriasis of cattle and sheep |
| Ancyclostoma caninum | Canines, felines | Canine and feline ancylcostomiasis |
| Uncinaria stenocephala | | |
| Stronglyoides papillosus | Sheep | Strongyloidosis of sheep |
| Stronglyoides ransomi | Pigs | Strongyloidosis of pigs |
| Dictyocaulus arnfieldi | Equines | Equine lungworm disease |
| Trichostrongylus axei | Cattle, sheep, horses | Stomach worm disease |
| Haemonchus contortus | Sheep, other ruminants | "twisted" stomach worm disease |
| Metastrongylus apri | Mainly porcine | Swine lungworm disease |
| Strongylus equinus | Equines | Strongylus disease of equines |
| Protostrongylus rutescens | Sheep, goats | Red lungworm disease |
| Dirofilaria immitis | Canines, felines | Heartworm disease of dogs and cats |

TABLE 9

Trematode infections of man

| ORGANISM | DISEASE |
|---|---|
| Schistosoma haemotobium | Bilharzia |
| Schistosoma intercalactum | Schistosomiasis intercalatum |
| Schistosoma japonicum | Japanese schistosomiasis |
| Schistosoma mansoni | Mansonian schistosomiasis |
| Fasciola hepatica | Fasciolasis |

TABLE 9-continued

Trematode infections of man

| ORGANISM | DISEASE |
|---|---|
| *Fasciolopsis buski* | Fasciolpsiasis |
| *Dicrocoelium dendriticum* | Dicrocoeliasis |
| *Opsithorchis felineus* | Opsithorchiasis |
| *Clonorchis sinensis* | Clonorchiasis |
| *Paragonimus westermanni* | Paragonimiasis |
| *Paragomimus kellikotti* | Paragonimiasis |

TABLE 10

Nematode disease of animals

| ORGANISM | Principal hosts | DISEASE |
|---|---|---|
| *Fasciola hepticus* | Sheep, cattle | Liver rot of sheep and cattle |
| *Fasciola gigantica* | Equines, bovines | Fascioliasis gigantica |
| *Fasciola magna* | Equines, bovines, sheep | Fascioloidiasis |

TABLE 11

Cestode disease of man

| ORGANISM | DISEASE |
|---|---|
| *Taenia solium* | Cysticercosis |
| *Echinococcus granulosus* | Hydatid disease |

TABLE 12

Regnum: Animalia; Subregnum: Protozoa

| Phylum | | Disease (animals) | Diseases (humans) |
|---|---|---|---|
| Sarcomastigophora | *Trichomonas vaginalis* | | Trichomoniasis |
| | *Trichomonas gallinae* | Avian trichomoniasis | |
| | *Tritrichomonas foetus* | Tritrichomonas abortion | |
| | *Giardia lamblia* | | Giardiasis |
| | *Leishmania* spp. | | Leishmaniasis |
| | *Trypanosoma* spp. | | Trypanosomiasis |
| | *Trypanosoma cruzi* | | Chagas' disease |
| | *Trypanosoma equiperdum* | Dourine in equines | |
| | *Trypanosoma evansi* | Surra in various domestic animals | |
| | *Trypanosoma brucei* | Nagana in bovines, equines, porcines, camels and canines | |
| | *Trypanosoma congolense* | Bovine trypanosomiasis | |
| | *Entamoeba histolytica* | | Amoebiasis |
| Apicomplexa | *Eimeria* spp. | Coccidiosis in poultry and bovines | |
| | *Isospora* spp. | Coccidiosis | |
| | *Isospora belli* | | Isosporosis |
| | *Toxoplasma gondii* | | Toxoplasmosis |
| | *Cryptosporidium parvum* | Cryptosporidiosis | Cryptosporidiosis |
| | Plasmodium spp. | | |
| | *Babesia bigemina* | | Malaria |
| | *Babesia caballi* | | Babesiosis |
| | *Babesia equi* | Equine piroplasmosis | |
| | *Histomonas meleagridis* | Blackhead enterohepatitis in avians | |
| Dinoflagellate | *Pfiesteria piscicida* | | |
| Ciliophora | *Balantidium coli* | | Dysentery |

TABLE 13

Regnum: Animalia; Subregnum: Metazoa

| Phylum | | Diseases (animals) | Diseases (humans) |
|---|---|---|---|
| Platyhelminths | *Fasciola hepatica* | Liver rot of sheep and cattle | |
| | *Fasciolopsis buski* | Fascioliasis gigantica in equines and bovines | Fasciolopsiasis |
| | *Fasciola gigantica* | | |
| | *Fasciola magna* | Fascioloidiasis | |
| | Schistosoma spp. | Cysticerocosis | Schistosomiasis |
| | Taenia spp. | | Pork and beef tapeworms of humans |
| Nematode | *Ascaris lumbricoides* | | Ascaridiasis |
| | *Enterobius vermicularis* | | Pinworm infection |
| | Trichuris spp. | Trichuriasis in cattle, sheep and pigs | Trichuriasis Ancylclostomiasis |
| | Ancyclostoma spp. | Canine and feline ancyclostomiasis | Ancylclostomiasis Filariasis |
| | *Nector americanus* | | Filariasis |
| | *Wucheria bancrofti* | | Onchocerciasis |
| | *Brugia malayi* | | Fish tapeworm infection |
| | *Onchocerca volvulus* | | |
| | *Diphyllobothrium* spp. | | Hydatid disease |
| | *Echinococcus granulosus* | | |
| | Hymenolepis spp. | | Hymenolepiasis |
| | Strongyloides spp. | Strongyloidosis of sheep and pig Equine lungworm disease | |
| | *Dictyocaulus arnfieldi* | Stomach worm disease of cattle, sheep and horses | |
| | *Trichostrongylus axei* | "twisted" stomach worm disease in sheep and other ruminants | |
| | *Haemonchus contortus* | | |
| | *Metastrongylus apri* | Swine lungworm disease | |
| Nematode | *Protosrongylus rutescens* | Red lungworm disease in sheep and goats | |
| | *Dirofilaria immitis* | Heartworm disease of dogs and cats | |

5.6.3. Macrophage Targeting in Various Diseases

A variety of diseases, including infectious disease, autoimmune disease, and cancer involve host macrophage responses. Macrophages are ideal targets of phosphoaminoglycosides because of their relatively high rate of membrane turnover during phagocytosis. The phosphate groups of phosphoaminoglycosides present a barrier to crossing cell membranes. However, cells undergoing rapid membrane turnover, particularly through phagocytosis, can preferentially take up phosphoaminoglycosides. Thus, macrophages can be targeted for phosphoaminoglycoside-mediated disruption of nucleic acid metabolism. Diseases which can be treated by such targeting of affected macrophages include, but are not limited to, arthritis, infections of protozoic organisms living in macrophages (e.g., Leishmania, metatastes in which macrophages occur in lymph nodes, and AIDS (increased infected host cell death). In the case of AIDS, decreased DNA repair resulting from phosphoaminoglycoside treatment can increase the efficacy of standard DNA damaging agents such as azidothymidine, dideoxyinosine, etc.

Targeting of macrophages would also produce immunosuppression for facilitating organ or graft rejection.

5.7. Dosages and Treatment Modes

The identified compounds that inhibit nucleic acid metabolism can be administered to a patient at therapeutically effective doses to treat or ameliorate disease. A therapeutically effective dose refers to that amount of the compound sufficient to result in amelioration of symptoms of disease.

5.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to normal or uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

In an alternative embodiment of oral administration for treating or preventing infectious disease (e.g. protozoan infection), for example, in animals (e.g., livestock), the phosphoaminoglycoside compounds described herein above may be added to food in the form of bacterial preparations. More specifically, cultures of bacteria that are resistant to a given aminoglycoside accumulate the phosphoaminoglycoside derivative when grown in the presence of the aminoglycoside. Such bacterial cultures can be harvested, inactivated (e.g., through exposure to ultraviolet light or radioactivity) and added to food supplies, such as livestock feed.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The compositions may be delivered by the using an appropriate route of administration. For example, and not by way of limitation, an enteric coating can be used, for example, for delivery to lower GI system. The compositions can be injected directly as appropriate into cavities or masses. For example, and not by way of limitation, the compositions can be injected intraperitoneally (e.g. ovarian metastases); intrathecally (e.g. brain tumors, lymphomas); intramuscularly (e.g. for clearance by the lymphatic system to target metastatic cells; into a lymph duct (intraluminally; e.g. to target metastatic cells); into a tumor or other unwanted cellular mass; into a blood vessel (intraarterially) which supplies a tumor or unwanted cellular mass such as uterine fibroids; intratesticular—testicular cancer; intraarticular—injection into a joint or bursa (in a fashion similar to steroids) to provide a locally high concentration of the active compound that would serve to destroy invading macrophages and other cells that lead to aggravation of the arthritic condition.

Injections could be less frequent than for other agents such as steroids, since the clearance rate of phosphoaminoglycosides should be slow.

The compositions can also be applied, in accordance with the invention, topically. For such topical administration, for example, the compositions may include a cell permeabilizing agent such as DMSO; a cell fusion system—such as liposomes; or, for treatment of plants or insects, a cell wall destroying agent—such as chitinase.

For localized application and release and also timed released, the compositions may include a collodion.

5.8. Use of Phosphoaminoglycosides as Delivery System for Other Therapeutic Agents The parent aminoglycoside binds to the phospholipid membrane as a result of the positive charge on the aminoglycosides. Turnover of the phospholipid membrane (e.g. endocytosis, pinocytosis, phagocytosis, membrane recycling) then leads to internalization of the aminoglycoside. In the case of the phosphoaminoglycoside derivatives, the internalized compound now has a target (DNA-dependent ATPase) and thus the aminoglycoside parent has functioned as a delivery system for the 3'-phosphate. The aminoglycosides can be useful for delivery of many other molecules and drugs which could be coupled through the various chemical moieties (e.g. hydroxyl and amine groups). Such new derivatives can include drugs, particularly nucleoside analogs such as, for example, azidothymidine (AZT), dideoxyinosine (ddI), dideoxycytosine (ddC), which could be phosphorylated (to yield a corresponding nucleotide analog) and attached to the aminoglycoside by a condensation yielding, for example, 5'-azidothymidine monophosphate-4'-aminoglycoside. Alternatively, the nucleotide moiety can be coupled to the aminoglycoside at other positions, including, for example, the hydroxyl group at the 2" position. In additional embodiments, the nucleotide moiety can be coupled to a corresponding phosphoaminoglycoside.

Such molecules could be specifically targeted towards cells undergoing active endocytosis such as macrophages (host cells for the nucleoside/nucleotide analog target enzyme known as HIV reverse transcriptase) where hydrolysis would release a phosphorylated nucleoside molecule (i.e., the corresponding nucleotide). Cell types that can be targeted include, but are not limited to, those of the lymphatic system (macrophages and monocytes), those of the nervous system (neurons), and others having higher rates of membrane turnover than normal cells. Thus, in accordance with the invention, phosphaminoglycoside are used to treat diseases known to be the direct result of colonization of these cell types by viruses, including but not limited to HIV for macrophages and varicella-zoster virus or polio for neurons.

The advantages of administering such nucleoside analogs coupled to either aminoglycosides or, alternatively, phosphoaminoglycosides are: a) nucleosides such as AZT, ddI, and ddC are small molecules which enter and poison all cells to some degree, whereas the nucleotide-aminoglycoside derivative would only enter cells with active membrane turnover therefore yielding decreased toxicity to other cells; and b) phosphorylated nucleotide derivatives do not normally enter cells but a phosphorylated derivative of the nucleoside could be released within the cell by this mechanism thus eliminating a few of the phosphorylation steps required for activation.

This coupling of nucleotide to aminoglycoside is readily accomplished by using the biochemical enzymatic activity of the aminoglycoside nucleotidyl transferases which are well known in the art. These enzymes transfer nucleoside monophosphates from the nucleoside triphosphate directly to the aminoglycoside ring (Gates, C. A. and Northrop, D. B., "Substrate Specificities and Structure-Activity Relationships for the Nucleotidylation of Antibiotics Catalyzed by Aminoglycoside Nucleotidyltransferase 2"-I", Biochemistry 1988, 27, 3820–3825; Pedersen, L. C., Benning, M. M. and Holden, H. M., "Structural Investigation of the Antibiotic and ATP-Binding Sites in Kanamycin Nucleotidyltransferase", Biochemistry 1995, 34, 13305–13311, each of which is hereby incorporated by reference in its entirety).

Such combined compositions can be formulated and administered according to the methods set forth in Section 5.7, above.

6. EXAMPLE

Isolation of the DNA-Dependent ATPase A Gene

The isolation and characterization of the novel bovine and human DNA-dependent ATPase A genes are described in detail in the following subsections.

6.1. Amino Acid Analysis of Native DNA-Dependent ATPase A

Adenosine triphosphatase A was initially isolated as a series of proteolytically derived polypeptides (Mesner et al., *Biochemistry.* 32, 7772–7778 (1993)). In order to reduce the heterogeneity so that amino acid sequencing could be performed, the immunoaffinity-purified enzyme was subjected to digestion with cyanogen bromide.

6.1.1. Cyanogen Bromide Digestion

In preparation for amino acid sequencing, 40 μg of 83-kDa DNA-dependent ATPase A was digested with 2 mg cyanogen bromide dissolved in formic acid. The reaction proceeded for sixteen hours at room temperature, after which the protein sample was brought to dryness in a Speed Vac centrifugation system. The digested peptide sample was re-dissolved and brought back to dryness five times, until the pH of a parallel myosin digestion rose to approximately pH 7. Following digestion, the samples were separated on tricine gels, and either silver-stained or transferred onto an Immobilon-P$^{SQ}$, a polyvinylidene difluoride (PVDF) membrane (Millipore).

6.1.2. Tricine Gel Electrophoresis

In order to resolve peptides smaller than 20-kDa, tricine gels were employed as described (Schagger and Von Jagow. *Anal. Biochem.* 166, 368–379 (1987)). These were based on the traditional SDS-PAGE gels as described by Laemmli (Laemmli. *Nature.* 227: 680–685 (1970)), but use tricine rather than glycine as the trailing ion. This allows for better separation of peptide fragments below 20-kDa. For the cyanogen bromide digested peptides, the standard 4% T, 3% C stacking gel was used, layered upon a 10% T, 3% C spacer gel, which in turn was layered onto a 16.5% T, 6% C separating gel. The silver-stain of cyanogen bromide digested DNA-dependent ATPase A showed peptide fragments of 25-, 18.5-, 13.5-,10-, 8-, 7-, 5-, 4.5-, 4-, and 3-kDa.

6.1.3. Peptide Transfer from Gel to Membrane

In order to perform western blots of peptide samples, it was necessary to transfer the peptides from the gel onto nitrocellulose membranes. This transfer was accomplished using an electroblotting system and a transfer solution comprised of 25 mM Tris-HCl, 192 mM glycine, 20% methanol, pH 8.3 (Towbin et al., *Proc. Natl. Acad. Sci. U.S.A.* 76, 4350–4354 (1979)). The standard transfer protocol involved sandwiching the membrane and gel between transfer solution-soaked blotter paper and applying an electric field of 0.2 V/cm$^2$ for a period of 45 minutes. Transfer success was quickly assayed by noting whether the gel running dye had migrated onto the nitrocellulose membrane.

6.1.4. Edman Degradation Peptide Sequencing

Automated Edman degradation peptide sequencing was conducted by the University of Virginia Health Sciences Center Biomolecular Research Facility. Protein sample was supplied to the facility immobilized on Immobilon-P$^{SQ}$, a polyvinylidene difluoride (PVDF) membrane (Millipore). The automated degradation process reacted the N-terminal amino acid residue with phenylisothiocyanate under basic conditions to produce a phenylthiocarbamyl derivative of the polypeptide chain. The phenylthiohydantoin derivative of the N-terminal amino acid was then generated following cleavage using gaseous trifluoroacetic acid. The products were identified by reverse phase chromatography on a C18 column using an on-line high-pressure liquid chromatograph (HPLC). The process was then repeated on the next N-terminal residue. Each cycle was approximately 92% efficient.

Three bands from the cyanogen bromide digestion of the 83-kDa form of DNA-dependent ATPase A, corresponding to masses of 4-, 7-, and 10-kDa, were analyzed by the Biomolecular Research Facility. Sequencing of the 4-kDa peptide resulted in a single reading of thirty-five amino acids. The 7- and 10-kDa bands contained multiple peptide fragments, but because the ratios of the peptides were different it was possible to resolve the overlapping readings into unique peptide sequences. The peptide sequencing results are given in Table 14. In a few cases, an individual amino acid residue could not be conclusively determined, this is represented by a dash in the sequence. The most probable cause of the undetermined residues was the fact that cyanogen bromide can react with cystine to form the oxidized cysteic acid, which is not a resolved peak in peptide sequencing determination. Cyanogen bromide can also react with basic amino acid residues, but carrying out the digestion under acidic conditions minimized this.

N-terminal analysis of the 83-kDa DNA-dependent ATPase A was also performed and the results are reported in Table 3.

TABLE 14

Peptide Sequencing Results for DNA-dependent ATPase A Fragments

| | | | |
|---|---|---|---|
| 4-kDa | SRPAELYTQI | LAVRPTFFPQ | FHAFGLRY-GAKRQP (SEQ ID NO: 10) |
| 7-kDa #1 | PLLKVAKRVI | LLSGTPA (SEQ ID NO: 11) | |
| 7-kDa #2 | ERVRGLPQVT | LQPLPK (SEQ ID NO: 12) | |
| 7-kDa #3 | KAAQRLPGIT | LQPLE (SEQ ID NO: 13) | |
| 10-kDa #1 | GLGKTIQAI- | IAAYYRKE-P | LLVVVP (SEQ ID NO: 14) |
| 10-kDa #2 | TTKDKTKQQQ | KEALILFF-R | TAEAKI (SEQ ID NO: 15) |
| 83-kDa #1 | TEGRLQQKAG | TPMHRVVGSQ | Q (SEQ ID NO: 16) |
| 83-kDa #2 | AGTPMHRVVG | SQQGRCIRNG | E (SEQ ID NO: 17) |

6.2 Cloning and Analysis of Bovine DNA-Dependent ATPase A cDNA 6.2.1. Determining the Encoding Nucleic Acid Sequence for DNA-dependent Adenosine Triphosphatase A 6.2.1.1. Primer Preparation for Cloning Information gained from peptide sequencing was used to produce oligonucleotide primers to amplify the DNA encoding DNA-dependent ATPase A. This was done by taking into account the degeneracy of the genetic code, as well as by examining the relative use of different triplet codons by mammalian species (Sharp et al., *Nucleic Acids Res.* 16, 8207–8211 (1988)). Each amino acid residue in a protein is coded for by three nucleotides in the mRNA. In the case of methionine there is only one option; ATG must be the codon used. In all other cases, one or two positions of the codons could not be positively determined, due to the intrinsic wobble of the genetic code. Two types of DNA oligonucleotides were generated depending on how this wobble was incorporated into the primer. A third type of oligomer was derived from nucleic acid sequencing information, and as such was an exact primer.

The first type of primer was termed a "degenerate" primer. In this case, the primer is actually a mixture of many different oligonucleotides. At each of the wobble nucleotide positions in the primer, each possible coding nucleotide was included during the synthesis. For example, the DNA triplets ATT, ATC, and ATA code for isoleucine. In the primer synthesis, the automated synthesizer randomly added one of the three possible nucleotides (T, C, or A) to each growing oligomer chain. In the case where a nucleotide was certain, as in the first two positions of the isoleucine codon, only that nucleotide was available in the synthesis. At the end of the synthesis the primer mixture contained all possible primers. The degeneracy of these primers is calculated based on the total number of wobble positions in the primer and the number of possible nucleotides at each wobble position. Typically, the degeneracy was on the order of 128- or 256-fold. Thus, a primer with a 256-fold degeneracy contains 256 different oligonucleotide species, only one of which is an exact match to the coding sequence. In addition, a small number of oligomers contain one error in the coding sequence, a larger number contain two errors, and so on. Obviously, some primer syntheses could have a very large degeneracy, and thus a very large number of incorrect primers, especially if they were designed in regions containing amino acids with multiple codons. Regions leading to very high levels of degeneracy were generally avoided.

The second type of primer designed was termed a "guessmer" primer. In this case, a best guess was made based on the human codon usage (Sharp et al., *Nucleic Acids Res.* 16, 8207–8211 (1988)). For each wobble position, only a single nucleotide was inserted. Each guessmer contains only a single oligonucleotide that in theory should be an exact match to the DNA coding sequence. If an error was made in designing the sequence it could not be overcome by brute force as in the degenerate primer example. On the other hand, the total concentration of the guessmer would be much higher than any individual primer found in the degenerate primer mixture.

The third type of primer is an "exact" primer. These primers are generated directly from the DNA sequence after a portion of the DNA-dependent ATPase A gene is cloned. These primers are the most useful, and the vast majority of primers were made in this fashion. Other than by using a stretch of methionine residues, it is impossible to make an exact primer from the protein sequence information directly, so the initial primers were generated as degenerate primers or guessmers. As regions of DNA-dependent ATPase A were amplified and cloned, it was possible to make exact primers within the known regions. The Biomolecular Research Facility at the University of Virginia generated all primers used, and quality was checked via spectrophotometric analysis and gas chromatography. A complete list of primers is shown in Table 15.

TABLE 15

Primers Made during DNA-dependent ATPase A Cloning

| Primer and Type | | DNA Sequence (5' -> 3') | Comments | Position |
|---|---|---|---|---|
| 008 | G | TTCTTCCCcC AGTTCCAT (SEQ ID NO:18) | Forward | 1809 |
| 009 | G | AAAGGCATGG AACTG (SEQ ID NO:19) | Reverse | 1801 |
| 037 | E | TCCCTGACTT AGAAGGATCT (SEQ ID NO:20) | Reverse | 167 |
| 038 | E | CCCTGCTTGG ACTGGGCAG (SEQ ID NO:21) | Reverse | 128 |
| 043 | E | TTGGGGTTGT GAGTTAGGTC A (SEQ ID NO:22) | Forward | 443 |
| 044 | E | CTTCCAGGAG AAAGCTCCAC (SEQ ID NO:23) | Reverse | 1110 |
| 080 | E | AGATATCATA TGAGCATCTC CCCATTAAAA (SEQ ID NO:24) | Forward | 20 |
| 082 | E | TCTTCCAAAG GCTGCAGGG (SEQ ID NO:25) | Reverse | 884 |
| 083 | E | CCAGCAGAAG TTACGATCCT G (SEQ ID NO:26) | Forward | 808 |
| 170 | E | GTTTTCCCAG TCACGAC (SEQ ID NO:27) | Forward | /// |
| 171 | E | CAGGAAACAG CTATGAC (SEQ ID NO:28) | Reverse | /// |
| 178 | E | AGGAGGCTGT CCAGAGGAAG (SEQ ID NO:29) | Reverse | 545 |
| 179 | E | CAGGCTGTGG GCATCTCTTC (SEQ ID NO:30) | Reverse | 313 |
| 193 | D | TCGAATTCTA tTAccGgAAg GA (SEQ ID NO:31) | Forward | 1427 |
| 230 | D | GAgcTcTAcA CgCAgAT (SEQ ID NO:32) | Forward | 1772 |
| 380 | — | GACTCGAGTC GACATCGAGG (G) (SEQ ID NO:33) | Linker | /// |
| 384 | E | AGGGAAGAAG GTCGGCCTGA C (SEQ ID NO:34) | Reverse | 1780 |
| 385 | E | CTCGCCGTCA GGCCGACCTT (SEQ ID NO:35) | Forward | 1793 |
| 386 | E | ATGGGCCTGG GCAAGACCAT (SEQ ID NO:36) | Forward | 1391 |
| 389 | — | GACTCGAGTC GACATCG (SEQ ID NO:37) | Linker | /// |
| 390 | — | GACTCGAGTC GACATCGATT (T)$_{15}$ (SEQ ID NO:38) | Linker | /// |
| 430 | — | GGGCTTAAAT TGGTCAACGA (SEQ ID NO:39) | Forward | /// |
| 431 | — | GAGTCCCGTC CTTTGCTGAC (SEQ ID NO:40) | Reverse | /// |
| 497 | E | AGGAGATGAC CACCAAGGAC A (SEQ ID NO:41) | Forward | 2056 |
| 502 | E | GCTCGAATTC TTATAGAGGA GAGGTAAAGC T (SEQ ID NO:42) | Reverse | 2806 |
| 503 | E | TATACCATGG CAGGGACCCC GATGCACAGA (SEQ ID NO:43) | Forward | 687 |
| 504 | E | AGTCCTTTGA TCCAGGTTCC C (SEQ ID NO:44) | Forward | 2719 |
| 505 | E | TCGAAGGACT TCTGGAATAG G (SEQ ID NO:45) | Reverse | 2640 |
| 507 | E | GAGGAGAGGT AAAGCTGTCC C (SEQ ID NO:46) | Reverse | 2801 |
| 563 | E | GCTCCCAGGT GAAGCGCAC (SEQ ID NO:47) | Reverse | 1459 |
| 742 | E | GCTCGAATTC ATGAGCATCT CCCCATTAAA (SEQ ID NO:48) | Forward | 20 |
| 743 | E | TTCTCAGCTT TTGCCAAGTT TCCG (SEQ ID NO:49) | Forward | −15 |
| 815R | G | ACCATCCAgG CCATCTcCAT tGCt (SEQ ID NO:50) | Forward | 1410 |
| 816 | G | GTAgTAGGCa GCaATGgAGA TGGC (SEQ ID NO:51) | Reverse | 1396 |

Key: G = guessmer primer, D = degenerate primer, E = exact primer

Lowercase letters in guessmers show an incorrectly guessed base, lowercase letters in degenerate primers show the correct base at a point of degeneracy. Position is 3' end of primer relative to start codon, where A of ATG=+1. Positions of linker primers are not determined.

A position of "///" means the primer did not anneal to DNA-dependent ATPase A sequence, but rather to a plasmid sequence or to a polynucleotide tail.

In addition to the degenerate, guessmer, and exact primer designation, each primer is described as either "forward" or "reverse." The forward primers all contain DNA sequence that corresponds to the reading frame expected in the mRNA strand. The reverse primers contain DNA sequence from the DNA strand that is the template for mRNA synthesis. Generation of cDNA from mRNA requires a reverse primer to anneal to the mRNA.

6.2.1.2. DNA Templates for PCR Cloning

In order to clone DNA-dependent ATPase A several different DNA templates were used. One template was simply genomic bovine DNA (Sigma). In addition, cDNA generated from fetal calf thymus poly(A)$^+$ RNA was used (see below). A third template was a bovine aorta endothelial cell (BAEC) cDNA bacteriophage library that was prepared and kindly supplied by the laboratory of Dr. Michael Peach (University of Virginia). While the sequence data presented below consists of reports of cDNA from calf thymus mRNA, the sequence was also confirmed using DNA-dependent ATPase A specific primers to amplify sequences from the BAEC library as well. Amplified regions of the BAEC library were ligated into PGEM-T and transformed as described below.

6.2.1.3. mRNA Extraction

RNA from calf thymus tissue was prepared using the guanidine HCl method as described in *Molecular Cloning* (Sambrook et al, 1989, supra). Ten volumes of 8 M guanidine HCl, 0.1 M sodium acetate (pH 5.2), 5 mM dithiothreitol and 0.5% sodium lauryl sarcosinate were added to a fragment of calf thymus tissue. The resulting solution was homogenized with a Dounce homogenizer for one minute at room temperature. The homogenate was clarified by centrifugation at 5000×g for 10 minutes at room temperature. The resulting supernatant was transferred to a new tube and 0.1 volumes of 3 M sodium acetate (pH 5.2) was added. Following mixing, 0.5 volumes of ice-cold ethanol was added and mixed thoroughly. The solution was stored for at least 2 hours at 0° C. The nucleic acids were recovered by centrifugation at 5000×g for 10 minutes at 0° C. The supernatant was discarded and the pellet allowed to dry at room temperature. The pellet was dissolved in 8 M guanidine HCl, 0.1 M sodium acetate (pH 5.2), 1 mM dithiothreitol and 20 mM EDTA. Approximately 10–15 ml of buffer should be used for every gram of original tissue. The nucleic acids were precipitated by adding 0.5 volumes of ice-cold ethanol and the solution was immediately mixed. The solution was stored at −20° C. for at least 2 hours. The nucleic acids were recovered by centrifugation at 5000×g for 10 minutes. Following discarding of the supernatant, the nucleic acids were precipitated twice more (total of three precipitations). The resulting pellet was then dissolved in a minimal volume of 0.02 M EDTA, pH 8.0. An equal volume of chloroform:1-butanol (4:1) was added and vortexed. Following centrifugation at 5000×g, the aqueous phase (upper) was transferred to a new tube and the extraction repeated. The nucleic acids were then precipitated by adding 3 volumes of 4 M sodium acetate (pH 7.0) and storing for at least an hour at −20° C. Centrifugation at 5000×g for 20 minutes at 0° C. allows the DNA to remain soluble while the RNA precipitates. The supernatant was removed and the pellet washed once with 3 M sodium acetate (pH 7.0) at 4° C. Following centrifugation at 5000×g for 20 minutes (0° C.), the supernatant was removed and the pellet dissolved in a minimal volume of 0.2% sodium dodecyl sulfate and 0.05 M EDTA (pH 8.0). The RNA was precipitated once more by adding two volumes of ice-cold ethanol, storing for 2 hours at 0° C and centrifuging at 5000×g. The pellet was washed with 70% ethanol and following re-centrifugation allowed to dry.

This total RNA was passed over an oligo(dT)-cellulose column to select the poly(A)$^+$ RNA. This procedure consisted of suspending 1 g of oligo(dT)-cellulose in 0.1 N NaOH and pouring into a column that has been pretreated with diethyl pyrocarbonate (DEPC) and autoclaved. The column was then washed with three volumes of DEPC-treated water. The column was then washed with 20 mM Tris-HCl pH 7.6, 0.5 M NaCl, 1 mM EDTA and 0.1% sodium lauryl sarcosinate in DEPC-treated water. The RNA pellet was dissolved in DEPC-treated water and heated to 65° C. for five minutes. Following rapid cooling to room temperature, the RNA was diluted with an equal amount of 40 mM Tris-HCl pH 7.6, 1.0 M NaCl, 2 mM EDTA and 0.2% sodium lauryl sarcosinate in DEPC-treated water. This solution was applied to the column and the eluate was collected. The column was then washed with one column volume of 20 mM Tris-HCl pH 7.6, 0.5 M NaCl, 1 mM EDTA and 0.1% sodium lauryl sarcosinate in DEPC-treated water. When all the solution had eluted, the eluate was heated again to 65° C. for five minutes, cooled to room temperature and loaded onto the column. Following loading, the column was washed with 20 mM Tris-HCl pH 7.6, 0.5 M NaCl, 1 mM EDTA and 0.1% sodium lauryl sarcosinate in DEPC-treated water until the $OD_{260}$ was very low. The poly(A)$^+$ RNA was eluted from the oligo(dT)-cellulose with 2–3 column volumes of 10 mM Tris-HCl pH 7.6, 1 mM EDTA and 0.05% SDS in DEPC-treated water. The fractions containing the RNA were identified by their characteristic $OD_{260/280}$ ratio. After collection, aliquots of total RNA and mRNA were stored at −80° C. until needed.

6.2.1.4. cDNA Generation from mRNA

The next step in the identification of the encoding DNA for DNA-dependent ATPase A was preparation of a DNA template for the polymerase chain reaction (PCR). One of the most important templates used was cDNA generated from fetal calf thymus poly(A)$^+$ RNA. The mRNA was transcribed into DNA by using one of three different reverse transcriptase procedures, employing Avian Myeloblastosis Virus Reverse Transcriptase (AMV RT) (Promega), Moloney Murine Leukemia Virus Reverse Transcriptase (M-MLV RT) (Promega), or *Thermus thermophilus* DNA polymerase (Tth) (Epicentre Technologies). Each of these reverse transcriptase enzymes has slightly different features such as allowing longer cDNAs to be generated or higher thermostability thereby allowing fewer nonspecific cDNA transcripts to be generated. All yielded the same results and 400 units of the M-MLV RT along with 2 μg of the poly(A)$^+$ RNA and 0.25 μM oligo(dT) were typically employed. The poly(A)$^+$ RNA is mixed with the oligo(dT) primer and boiled for two minutes, followed by slow cooling to room temperature. The oligo(dT)-primed poly(A)$^+$ RNA was then mixed with the M-MLV RT in 50 mM Tris-HCl pH 8.3, 75 mM KCl, 3 mM $MgCl_2$ and 10 mM dithiothreitol. The mix was incubated at 37° C. for two hours. At the end of 1 hour, 200 additional units of M-MLV RT were added to the reaction. The cDNA was purified away form the primers and enzyme using the GlassMAX DNA Isolation Spin cartridge System (GIBCO BRL). The purification was performed as described in the GIBCO BRL instruction manual. The purified cDNA was resuspended in TE buffer (10 mM Tris-HCl pH 8.0, 1 mM EDTA).

6.2.1.5. Polymerase Chain Reaction (PCR) Techniques and Cloning

Amplification of specific DNA sequences from a larger DNA template was achieved using the polymerase chain reaction (PCR) technique. PCR involved three phases: denaturing, annealing, and extending. In the first step, the dsDNA template was denatured by heating the reaction tube to a very high temperature, usually 95° C. In the second phase the reactants were cooled and specific DNA oligomers, or primers, bound to the ssDNA template. In the last phase the primers were extended by a polymerase, following which the dsDNA product was heat denatured again to form two ssDNA molecules. In each successive round of amplification, the newly synthesized DNA was then available to act as a template in the next round. This process was repeated for N cycles, with the desired DNA product theoretically amplified $2^N$ times.

Standard PCR conditions: The reactants were mixed in a 0.5 ml eppendorf tube. Usually, a "master mix" containing all the reactants except the primers and DNA template was made and placed in aliquots into the individual reaction tubes. On occasion, the reaction tubes remained on ice without enzyme for up to two hours before PCR was initiated, but usually the reactants were assembled immediately prior to PCR amplification. DNA template was added in a small volume, typically no more than 10% of the final 50 μl reaction volume. Since PCR enables such a large amplification of the DNA, nanogram amounts of DNA were sufficient to act as the template. Each 50 μl reaction contained a buffer of the following composition: 50 mM Tris-HCl pH 9.0, 50 mM NaCl, and 10 mM $MgCl_2$. Each of the two primers was added to final concentrations of 0.1 μM nucleotides. The dNTPs (DATP, dTTP, dCTP, dGTP) were added to a final concentration of 0.5 mM each. The reaction volume was adjusted to 50 μl with the addition of $dH_2O$. Finally, 2 units of heat stable Taq polymerase (Promega) were added. An equal volume of mineral oil was layered on top of the reaction mixture to prevent evaporation during the heating cycles.

The standard PCR reaction cycle was as follows: denaturation at 94° C. for 1 minute, annealing at 55° C. for 2 minutes, and extension at 72° C. for 3 minutes. The standard reaction contained 35 cycles of denaturation, annealing, and extension. Following the final extension step, the reaction tubes were maintained at 72° C. for 10 minutes, and then held at 4° C. for up to 12 hours.

Precycling PCR conditions: In some reactions that involved the potential for primers that did not anneal perfectly to the template DNA, several rounds of "precycling" were performed before the standard PCR conditions were used. The reaction components were the same as for the standard PCR, but a lower annealing temperature was used. The precycling PCR conditions were: denaturation at 94° C. for 1 minute, annealing at 37° C. for 2 minutes, and extension at 72° C. for three minutes. Three rounds of precycling were typically used, followed immediately by the standard PCR cycle.

Secondary PCR: In some instances, a second PCR reaction was performed. These "secondary" PCR reactions were used to confirm the results of the primary PCR reaction, which could give a number of amplified bands, only one of which was the desired product. Secondary PCR reactions required a DNA template associated with a standard PCR reaction. Either 1 µl of a 20-fold dilution of primary PCR was used as the template, or 1 µl of a GELase-treated IMP agarose DNA band was used (see below). The secondary PCR employed two distinct oligonucleotide primers that annealed internally to the primary PCR primers. Thus, secondary PCR could only be used in a region of which some sequenced information had been confirmed and some specific primers had been synthesized. The secondary PCR reaction cycles were performed in the same manner as the standard PCR reactions.

Low Melting Point (LMP) Agarose Gel Electrophoresis: IMP agarose gel electrophoresis allowed separation of DNA species by their size differences (as did "standard" agarose gel electrophoresis), but in addition LMP agarose allowed simple extraction of the desired DNA (see below). Typically 1% (w/v) LMP agarose gels were used. The standard buffer was 1×TBE diluted from a 10×stock solution. Electrophoresis was carried out at up to 80 V until the visualization dye migrated to the desired distance in the gel, typically 1 or 2 hours. Bands were visualized under UV light after staining in a solution of ethidium bromide (EtBr) 0.5 µg/ml $H_2O$ for 20 minutes.

IMP Agarose Digestion (GELase): In some instances a sample contained many different DNA species, but only one was the desired product. It was possible to physically remove the DNA by excising the band from the gel, followed by digesting the agarose away from the DNA using GELase (Epicentre Technologies). The digestions were carried out as described in the instruction manual, with the following changes. Two separate lanes containing the sample to be digested were electrophoresed. Following electrophoresis, one lane was stained in a solution of EtBr in $dH_2O$ (0.5 µg/ml), and the other lane was held in $dH_2O$ only. The stained band was removed from its gel lane, and the lane was used as a template to excise a slightly larger band from the unstained lane. This unstained band was digested using the GELase protocol.

PCR Cloning: The cloning process from mRNA was broken down into three phases. First, an attempt was made to amplify a specific DNA sequence within one of the previously determined peptide regions (Table 3). Next, an attempt was made to clone a region of DNA-dependent ATPase A between two of the sequenced peptides, since the DNA sequence could easily be translated and compared to the peptide sequence to ensure that the correct product was being cloned. Once this anchor region was elucidated, it was used to clone the rest of DNA-dependent ATPase A. The second phase determined the 3' region of DNA-dependent ATPase A by using a primer within the known region of DNA-dependent ATPase A and the poly(T) tail of cDNA generated from poly(A)$^+$ mRNA. The third phase completed the cloning of DNA-dependent ATPase A by determining the 5' region. This involved using the rapid amplification of cDNA ends (RACE) procedure, a variation of the technique used to sequence the 3' end.

In addition to the cloning attempts from mRNA, the BAEC phage library was also used as a source of template DNA. A specific primer from the DNA-dependent ATPase A sequence was used along with a primer that annealed to vector DNA. These amplifications yielded a large number of bands, each of which was ligated into PGEM-T and sequenced. Many of these inserts did not contain DNA-dependent ATPase A sequence, but several bands were found to correspond to DNA-dependent ATPase A. In the case where new DNA-dependent ATPase A sequence was cloned, primers were created and a confirming amplification was done using cDNA generated from mRNA.

Depending on the DNA template utilized for the amplification (genomic DNA, cDNA, etc.), different primers were used in the PCR reaction. When oligo(dT)-primed cDNA was generated from poly(A)$^+$ RNA, it was possible to use an oligo(dA)-containing primer during the PCR reaction. If such a poly(dT) tract was not present, such as in genomic DNA, this oligo(da) primer was not useful. If the template used was the BAEC library DNA, it was possible to use an internal DNA-dependent ATPase A primer and a vector-specific DNA primer. Obviously, this vector-specific DNA primer would be useless when using cDNA as a DNA template. Regardless of which template was used, it was always possible to amplify DNA-dependent ATPase A sequence using one forward and one reverse primer specific for DNA-dependent ATPase A sequence.

As the various PCR reactions yielded DNA-dependent ATPase A sequence information, it was possible to synthesize other exact primers. These could be used in turn to amplify unknown regions of the DNA-dependent ATPase A sequence. Often the new primers developed from PCR on one type of DNA template were used to amplify regions of DNA-dependent ATPase A from a second DNA template.

Rapid Amplification of cDNA Ends (RACE) PCR: To clone the 5' end of DNA-dependent ATPase A, a modified RACE procedure was used. The procedure is basically a variation of the one in the standard PCR cloning reactions, and included a unique cDNA tailing step as previously described. The steps that required alteration for the RACE procedure were the cDNA synthesis and the PCR amplification procedure.

cDNA generation for RACE PCR: cDNA was generated using 1.5 micrograms of poly(A)$^+$ calf thymus RNA, with 3.6 micrograms of random hexamers (Gibco) acting as the primer. The RNA and primers in a total volume of 10 µl were heated to 100° C. and allowed to cool slowly to approximately 45° C. over a 30 minute period, at which point RT buffer (50 mM Tris-HCl pH 8.3, 75 mM KCl, 3 mM $MgCl_2$ and 10 mM dithiothreitol) (Promega) was added. In addition, the reaction mixture was supplemented to a final concentration of 10 mM DTT, and 0.25 mM of each dNTP were added. 400 units of M-MLV RT were added and the reaction was run at 37° C. for two hours. Following the reverse transcription, the cDNA was purified using the GlassMAX procedure.

cDNA Tailing with Terminal Transferase: For the RACE procedure, a tail of dC residues was added to the cDNA. Terminal deoxynucleotidyl transferase (TdT) (Promega) acted as a template-independent polymerase, and added deoxynucleotides to the 3' end of an initiator DNA chain, usually cDNA. The initiator DNA is required, as TdT will not polymerize isolated deoxynucleotides. The enzyme, when presented with only one deoxynucleotide, produced a polynucleotide "tail" on the initiator DNA. This allowed cloning as described in the RACE PCR procedure. The tailing reaction proceeded as described in the literature accompanying the enzyme, except that the reaction was run for 20 minutes at room temperature.

RACE PCR: The tailed cDNA was used in a series of PCR reactions. The first reaction involved a primer that annealed to the dC tail, and an DNA-dependent ATPase A specific primer. This reaction involved three precycling steps at 37° C., followed by thirty-five cycles at 55° C. Following this amplification, the PCR product was diluted twenty-fold and one μl was used as a template for a second PCR reaction. This second reaction contained two different primers than the first reaction. In this second reaction no precycling step was performed. A schematic diagram of the RACE procedure is shown below.

Removal of Oligonucleotide Primers: Often it was necessary to remove excess oligonucleotide primers from one step of a protocol before continuing on with the next phase of the experiment. To accomplish this task, the GlassMAX DNA Isolation Spin Cartridge System (GIBCO BRL) was used. This procedure involved a silica-based membrane that selectively binds DNA. However, binding to the resin was related to the size of the DNA, and DNA smaller than 200 bp essentially pass through the column without binding. The DNA was bound by first mixing it with a NaI based binding solution, oligonucleotides and proteins were then washed away using the ethanol-containing wash buffer, and the desired DNA was eluted using warm elution buffer, typically 10 mM Tris-HCl pH 8.0, 0.1 mM EDTA. The protocol was followed as described in the instruction manual, except that the elution buffer was boiled in a microwave before elution.

Ligation: The PCR products were ligated to vector DNA in order to form stable plasmid constructs. The ligation protocol was followed as described in the pGEM-T technical bulletin (Promega), with the following alterations. The reaction was run overnight instead of for three hours. In addition to the supplied reaction buffer, the reaction was supplemented with an additional 1 mM ATP. While in some instances the DNA produced in a PCR reaction was used directly in the ligation reaction, in most instances the DNA was first electrophoresed in an LMP agarose gel, followed by excision and agarose digestion using GELase. This DNA was then used in the ligation reaction. In some cases, a vector other than pGEM-T was used, this is noted in the text of this dissertation.

Transformation of plasmid DNA into PGEM-T vector: Transformation involved the uptake of plasmid DNA by competent bacterial cells. Once a successful transformant was created it allowed the stable storage and amplification of different DNA-dependent ATPase A clones in a bacterial cell line. The ligated PCR product: pGEM-T vector reaction mix was used to transform High Efficiency JM109 Competent Cells (Promega) as described in the PGEM-T technical bulletin (Promega) with the following modifications. Five μl of ligation mix was used to transform 50 μl of competent cells instead of 2 μl. Following the heat shock and ice incubations, 1 ml Luria-Bertani (LB) (10 g tryptone, 5 g yeast extract, 10 g NaCl, adjust the pH to 7.0 by the addition of HCl, and bring the final volume to 1 L) was added to the cells. The LB (10 g tryptone, 5 g yeast extract, 10 g NaCl, adjust the pH to 7.0 by the addition of HCl, and bring the final volume to 1 L)/Ampicillin/IPTG/X-Gal plates were spread with 300 μl of cells instead of 50 μl.

Plasmid DNA Extraction from *E. coli*: DNA plasmids were used to conveniently store and produce partial and complete clones of the DNA-dependent ATPase A coding sequence. simply growing the selected cell line overnight in 100 ml of LB (10 g tryptone, 5 g yeast extract, 10 g NaCl, adjust the pH to 7.0 by the addition of HCl, and bring the final volume to 1 L) media containing an antibiotic produced several hundred micrograms of plasmid DNA. Once purified away from the bacterial cell proteins and genomic DNA, the plasmid DNA was available for a number of procedures, including DNA dideoxy sequencing, PCR, and restriction digestion. Midiprep plasmid kits (Qiagen) were used for plasmid purification. This alkaline lysis procedure involves a DNA-binding resin, and was used as described in the Qiagen Plasmid Handbook, with the following conditions. The standard growth conditions used were 100 ml of LB medium (10 g tryptone, 5 g yeast extract, 10 g NaCl, adjust the pH to 7.0 by the addition of HCl, and bring the final volume to 1 L), inoculated with a bacterial line from either a 1.5% agar LB (10 g tryptone, 5 g yeast extract, 10 g NaCl, adjust the pH to 7.0 by the addition of HCl, and bring the final volume to 1 L) plate or glycerol stock. In the case of PGEM-T vector, ampicillin was added to a final concentration of 60 μg/ml. These cultures were grown overnight in a shaker bath held at 37° C. Following the purification protocol, the plasmid DNA was mixed with an equal volume of $TE_8$-saturated phenol, pH>7:chloroform (1:1) and centrifuged in a microfuge for ten minutes. The aqueous layer was removed and to it 0.1 volumes of 3M NaOAc, pH 5.2 and 3.0 volumes of ethanol were added. The plasmid DNA was isolated via centrifugation for fifteen minutes in a microfuge. The resulting pellet was then washed three times with ice-cold 70% ethanol. The DNA was stored in either $ddH_2O$ or TE pH 8.

Dideoxynucleotide Sequencing: In order to determine the nucleotide sequence of selected clones, the chain-termination sequencing method was used. This involved the synthesis of a DNA strand in vitro using a dsDNA template, oligonucleotide primer, and the Sequenase Version 2.0 T7 DNA polymerase (United States Biochemical). Synthesis was initiated only at the site where the primer anneals to the plasmid DNA template, and the reaction was terminated by the incorporation of a nucleotide analog that prevents continued DNA elongation.

The procedure was carried out using the instructions in the Sequenase Version 2.0 DNA Sequencing Kit, 6th edition, amended as follows. The dsDNA template preparation method was used. Both 6% and 8% polyacrylamide gels were used, and the gels were run from 2 hours to 8 hours depending on the region of DNA that was being sequenced. Gels were soaked following electrophoresis one or two at a time in 2.5 L of 5% acetic acid/15% methanol solution. The solution was replaced after a total of six gels had been soaked in any given batch of solution.

PCR Amplification within the 4-kDa Peptide Region: The first successful reaction involved genomic DNA as the template. One primer used was a 256-fold degenerate primer (230) (see Table 15) corresponding to a sequence from the 4-kDa peptide (ELYTQI) (SEQ ID NO:52). The second primer (009) was a guessmer that corresponded to a different region within in the 4-kDa peptide (QFHAF) (SEQ ID NO:53). The peptide sequence between these two primers was established via the Edman degradation peptide sequencing, and predicted a size of sixty base pairs for the correct DNA clone. The sequence is shown in FIG. 13.

PCR Amplification Between the 4-kDa and 10-kDa #1 Peptide Regions

Once an exact sequence corresponding to part of the 4-kDa peptide was elucidated, two primers were made within the region, one forward (Primer 385) and one reverse (Primer 384). Using information from a PCR amplification of the BAEC library, an exact primer (Primer 386) was synthesized to a region of the 10 kDa #1 peptide (Table 14). Primer 384 was used to prime poly(A)+RNA, which was reverse as described. Oligonucleotides and polymerase were separated from the cDNA using the GlassMAX DNA purification system as described. This purified cDNA acted as a template in a PCR reaction, using primers 384 and 386. The PCR reaction included a "precycle" followed by the standard reaction. The reaction products were separated by electrophoresis on a 1.5% LMP-agarose gel, and six bands were seen, ranging in size from 100 to 400 bp. The four largest fragments were excised from unstained lanes, and these bands were digested with GELase (Epicentre). A second PCR reaction was performed on these purified DNA bands with primers 193 and 384 to determine the correct product, since the 384/193 product should be slightly smaller than the 384/386 product.

The secondary PCR reactions were electrophoresed in a 3% agarose gel. The approximately 400 bp 384/386 band resulted in a slightly smaller 384/193 band. Both the initial 384/386 and the 384/193 bands were excised from LMP-Agarose gels and the DNA was ligated into PGEM-T vector and transformed into competent JM109 cells. Plasmid DNA was isolated from five 384/386 transformants and the nucleotide sequence of the fragments was elucidated using dideoxy sequencing of three separate sequencing reactions. A translation of this sequence yields a single open reading frame containing peptide sequence from both the 4-kDa and 10-kDa #1 peptide sequencing reactions. The sequence determined and its translation (SEQ ID NO:60) are shown in FIG. 14.

3' End Cloning: Elucidation of the 384/386 region of DNA-dependent ATPase A allowed the construction of several distinct primers that were useful in cloning the 3' end of the sequence. A linker primer (Primer 390) was also constructed to generate a cDNA template from calf thymus poly(A)$^+$ mRNA. Primer 390 contained a run of seventeen T residues at its 3' end, which were designed to anneal to the poly(A)$^+$ tail of the mRNA. In addition, primer 390 contained a multi-restriction site (MRS) sequence at the 5' end. Primer 389 contained only the MRS sequence. The cDNA template was generated using Moloney-Murine Leukemia Virus reverse transcriptase (M-MLV RT). Following cDNA synthesis, the mRNA was removed using RNase A and the unincorporated primers were removed using GlassMAX (Gibco). The cDNA acted as a template for PCR, with an MRS-only primer (Primer 389) and an DNA-dependent ATPase A specific primer (504) used in the standard PCR amplification as described. A schematic representation is shown in FIG. 15. Eventually, it was possible to produce a clone from primer 386 to the MRS in the poly(da) tail of the cDNA. Following the stop codon was a poly(A)$^+$ tail addition sequence (AATAAT) that was followed by the poly(da) tract of bases (Wickens. *TIBS.* 15, 277–281 (1990)).

5' End Cloning: The final region of DNA-dependent ATPase A that was elucidated was the 5' end extending into the noncoding region. The method that was used to clone this region involved the RACE procedure. A number of different primers were used to generate cDNA, including priming mRNA with DNA-dependent ATPase A specific primers 37, 38, and 82, and long extensions using oligo(dT) priming. In addition, several different tailing mechanisms were used, including tailing with dA and dG, and also a single-stranded ligation of a linker oligonucleotide to the cDNA. However, despite multiple attempts, none of these cDNA templates produced the desired DNA band after tailing, PCR, cloning, and sequencing. The procedure that succeeded involved using 1.5 micrograms of poly(A)$^+$ calf thymus RNA, with 3.6 micrograms of random hexamers (Gibco) acting as the primer. It was thought that the random hexamers would anneal along the mRNA and perhaps disrupt secondary structures that interfered with extension of cDNA from the specific primers. Following the cDNA synthesis, a terminal transferase reaction was attempted using dG nucleotides as described. The tailed cDNA acted as the template for the first of two PCR reactions. The first PCR amplification involved DNA-dependent ATPase A specific primer 37, and the linker-primer 380, that contained the MRS sequence and a dC tail. The amplification began with a precycling step as previously described, followed by the standard amplification. The PCR reaction products were treated with GlassMAX, and diluted 1:20. The second PCR reaction used primers 389 and 38, with the dilution of the first PCR reaction as the template DNA. This second reaction generated a single band on an LMP-agarose gel, and the PCR product was ligated into pGEM-T. The plasmid was sequenced and showed a possible ATG start site, which was preceded by stop codons in all three potential reading frames. A diagram of the procedure can be seen in FIG. 16. The 5' end was also amplified using the BAEC library, using the vector specific primer (Primer 430) and an DNA-dependent ATPase A specific primer (Primer 37). The sequence of the library clone matched that of the cDNA clone. The cloned 5' end contains stop codons in all three frames upstream of the proposed ATG start site.

Complete DNA-dePendent ATPase A Clone from mRNA: Following the success of the RACE and 3' cloning procedures, specific primers were made at each of the cloned ends. This made it possible to generate the complete DNA-dependent ATPase A clone from calf thymus mRNA. cDNA was generated from CT mRNA using the oligo(dT) primer as described above. The excess oligo(dT) primers were removed by the GlassMAX procedure, and one tenth of the total volume of cDNA was used as a template in a PCR reaction. The primers for the complete clone were 502, which annealed to the 5' end of the cDNA (3' end of the mRNA), and 742, which annealed to the 3' end of the cDNA (5' end of the mRNA). Control reactions containing primers 384 and 386 were also attempted at the same time. Both reactions produced a single band of the desired size when electrophoresed on an agarose gel. The PCR products were used directly as the DNA insert for a ligation into pGEM-T vector.

The complete clone of DNA-dependent ATPase A was amplified from cDNA generated from calf thymus mRNA. Regions of DNA-dependent ATPase A were also amplified from genomic bovine DNA and BAEC library DNA. As more of the DNA-dependent ATPase A sequence was elucidated, new primers were synthesized to be used for amplifying and sequencing the DNA-dependent ATPase A clone. The amplification occurred in an overlapping fashion, which ensured that no incorrect sequence was mistakenly incorporated into the growing sequence.

A cDNA containing the complete DNA-dependent ATPase A coding sequence (as shown in FIG. 1) obtained from calf thymus, was isolated as an NdeI-EcoRI restriction fragment and inserted into pET-24a(+) to form plasmid pAT411. The complete DNA sequence is shown in FIG. 1, and the encoded amino acid sequence of the full-length DNA-dependent ATPase protein is shown in FIG. 2.

6.3. Northern Analysis of Bovine DNA-Dependent ATPase A mRNA

Primers 179 (5' probe) and 507 (3' probe) were radiolabeled and used to probe a Northern blot containing two samples of calf thymus mRNA. The mRNA was electrophoresed and transferred to nylon membrane as described in Sambrook, et al. 1989, supra, at pages 7.43–7.46. The nylon membrane was prehybridized with a formamide containing buffer as described in Sambrook et al., 1989, supra, at page 7.58, for 1 hour at 42° C., then hybridized overnight with probe at 42° C. Following hybridization, the membrane was washed as described in Sambrook et al., 1989, supra, at page 7.58, and exposed to film.

A single band containing an mRNA of approximately 3.2 kb in length was detected in each of the two samples of calf thymus mRNA.

6.4. Southern Analysis of Human, Murine, and Bovine DNA-Dependent ATPase A Gene

The human, murine, and bovine DNA-dependent ATPase A genes were detected and analyzed by Southern analysis.

Genomic DNA samples from each species were digested to completion using a single restriction enzyme. Buffer conditions and incubation temperatures were as described in the literature accompanying the enzyme. Typically, 50 μg of DNA was digested, using 100 units of enzyme. After incubation for 1 hour another 50 units of enzyme was added, and the incubation was carried out for an additional 3 hours. At this point an aliquot of approximately 3 μg DNA was removed and separated on an agarose gel to determine the success of the digest. If it appeared that the digest had gone to completion, which was determined by a lack of very high molecular weight species DNA (greater than 25 kb) and the presence of distinct bands caused by digestion of repetitive DNA, then the DNA was separated on a vertical gel in preparation for hybridization. If there was still high molecular weight DNA remaining, additional restriction enzyme was added and the reaction proceeded for another two hours. The gel was loaded so that the lanes on the right half of the gel contained identical samples to the lanes on the left half of the gel. Following electrophoresis, the DNA was transferred to Hybond-N membrane. When the membrane was cut in half, each half contained one lane of each of the digested DNA species, along with a marker lane of BstEI digested lambda DNA.

Two different DNA probes were generated to be used in a Southern hybridization, both from digested pPAT411. The first probe, termed the 5' probe, contained DNA from an NdeI/BamH I double restriction digest of pPAT411. This probe contained DNA from the 5' insertion site to base 1179 of the coding sequence. The second probe, termed the 3' probe, was a HindIII digest of pPAT411, and contained DNA from base 1285 through the end of the pPAT411 coding sequence, including approximately 20 bases into the multi-restriction site in the pET-24a(+) vector. The 3' probe contained all of the 7 helicase domain regions found in the SNF2 family proteins, while the 5' probe contained sequence unique to DNA-dependent ATPase A. Following digestion, the plasmid DNA was separated on a LMP agarose gel, and the proper DNA bands were excised for probe synthesis as described in the materials and methods section.

Hybridization was carried out for 36 hours at 65° C., following which the membrane was washed as described in the materials and methods section. The membrane was exposed to Kodak X-AR film and is shown in FIG. 21.

Lanes 1 and 5 contain bovine genomic DNA. Lanes 2 and 6 contain genomic murine DNA. Lanes 3 and 7 contain human genomic DNA. Lane 4 contains BstEII-digested λ DNA markers (New England Biolabs), which nonspecifically hybridize with the pPAT411 probe. Lanes 1 through 3 were hybridized to the 5, probe, lanes 4 through 7 were hybridized to the 3' probe. The sizes of the hybridized bands in kilobases are as follows, with matching bands underlined.

Bovine:
    Lane 1: 10.6, 9.5, 7.2, 4.2, 3.8, 3.4
    Lane 5: 10.6, 9.5, 8.3, 7.2, 4.7, 4.4, 3.8, 2.0
Murine:
    Lane 2: 14.2, 8.9, 5.2, 4.9, 3.9, 3.3
    Lane 6: 14.2, 8.9, 5.2, 4.9, 3.9, 3.3
Human:
    Lane 3: 13.2, 12.8, 8.7, 5.8, 2.5, 1.5
    Lane 7: 14.0, 13.2, 12.8, 8.7, 5.8

These results indicate that for each identical band in both the 5' and 3' lane there exists in the genome one copy of DNA-dependent ATPase A, or DNA-dependent ATPase A homologue, with at least a region of very high identity. Bands that appeared in only one of the two blots could not be specifically determined as unique copies. These results indicate, therefore, that the bovine genome contains 5 copies of DNA-dependent ATPase A, the murine genome contains 5 copies, and the human genome contains 4. The probe used was based on the bovine sequence, so deviations from the murine and human sequences could lead to underrepresentation in these two species.

6.5 Isolation of Human DNA-Dependent ATPase A cDNA

A cDNA was prepared using mRNA isolated from BT20 (human breast cancer) cells. Primer 390 was used for cDNA preparation. The cDNA was purified and amplified by PCR. Primers 505 and 385 from the bovine DNA-dependent ATPase gene were used for the amplification of the human cDNA. The amplified product was ligated into PGEM vector (Promega, Madison, Wis.) and transformed into JM109 *E. coli* cells. Plasmid DNA was purified from the transformants and sequenced using standard techniques. The DNA sequence of one human DNA-dependent ATPase cDNA, contained in one of these plasmids designated pAK505, is shown in FIG. 19. A comparison of the nucleotide sequence of the human and bovine genes is shown in FIG. 20 and demonstrates the high degree of homology between the bovine and human genes. A comparison of the amino acid sequence of the human and bovine polypeptides is shown in FIG. 21 and illustrates the high degree of homology between the bovine and human proteins.

7. EXAMPLE

Preparation and Analysis of the 82 kDa Active DNA-Dependent Adenosine Triphosphatase A Domain (ADAAD)

DNA-dependent ATPase A is the most abundant DNA-dependent ATPase from rapidly proliferating fetal calf thymus tissue (Hockensmith et al., Biochemistry. 25, 7812–7821 (1986)). A bank of monoclonal antibodies (MAbs) against proteolytically derived domain of native DNA-dependent ATPase A (bovine) and subsequently generated an immunoaffinity purification protocol which yields an enzyme of very high specific activity (Mesner et al., Biochemistry. 32, 7772–7778 (1993); Mesner et al., Biochemistry. 30, 11490–11494 (1991)). The monoclonal antibodies described in these references are available from the University of Virginia Lymphocyte Culture Center.

The immunoaffinity purified native DNA-dependent ATPase A polypeptide was cleaved and the amino acid sequences of seven different peptides were obtained by Edman degradation. The amino acid sequence information was used to derive a successful cloning strategy and to confirm subsequent nucleic acid sequencing results (FIG. 1). The calculated molecular mass of 104,800 (941 amino acids) (FIG. 2) for the polypeptide encoded by the clone is virtually identical to the previously reported observation of 105-kDa for immunoaffinity-purified DNA-dependent ATPase A (Mesner et al., Biochemistry. 32, 7772–7778 (1993)).

Two amino acid sequences derived from the N-terminus of the 83-kDa polypeptide are consistent with proteolytic cleavage following positions 214 and 222 of the sequence. The residues at these two positions are an arginine and a lysine suggesting cleavage by trypsin. More importantly, cleavage at these residues would yield polypeptides of nearly 83-kDa based on sequence analysis and stop site.

The amino acid sequence of DNA-dependent ATPase A contains a number of motifs, the most striking of which is the putative helicase domain that contains seven conserved boxes (Bork and Koonin. Nucleic Acids Res. 21, 751–752 (1993)). The seven conserved boxes represent the "molecular motor" upon which cloning, biochemical and chemotherapeutic strategies have been focused.

Homology searches using BLASTP (National Center for Biotechnology Information) demonstrate a high similarity of the DNA-dependent ATPase A sequence to that of the S. cerevisiae STH1 (NPS1) and Snf2 proteins (P(N)=1.2e-20 and 7.3e-19). Both of these proteins are currently considered to be in the same family (Eisen et al., Nucleic Acids Res. 23, 2715–2723 (1995); Tsuchiya et al., EMBO J. 11, 4017–4026 (1992); Steinmetz and Platt. Proc. Natl. Acad. Sci. U.S.A. 91, 1401–1405 (1994); Bork and Koonin. Nucleic Acids Res. 21, 751–752 (1993)). Use of the FASTA search program (Pearson and Lipman. Proc. Natl. Acad. Sci. U.S.A. 85, 2444–2448 (1988)) identifies an internal region of the S. cerevisiae MOT1 protein as having the highest similarity to DNA-dependent ATPase A; with Snf2, and STH1 (NPS1) ranked slightly lower. The MOT1 protein is a member of the SNF2 family and has approximately 28% identity with the sequence of DNA-dependent ATPase A over a region of the C-terminal 490 amino acids (aa 452 to aa 941), which includes all seven putative helicase motifs. The members of the SNF2 family are mostly divergent outside of the putative helicase motifs (Auble et al., Genes Dev. 8, 1920–1934 (1994)) and the peptide sequence from the N-terminus to amino acid 452 does not show significant homology to any known sequence (the sequence is correct since the N-terminal clone overlaps with another clone and the peptide sequences following positions 217, 285, 382 and 458 are all contained within the overlapping clone and have been confirmed by amino acid sequencing).

The homologous regions which define the SNF2 family have been identified as putative helicase domains. The genes from many members (SNF2, STH1, YAL001, MOT1, RAD54, RAD16, RAD5, etc.) of this family have been identified in Saccharomyces cerevisiae through direct genetic manipulations, while additional members have been identified from humans and Drosophila by amino acid sequence comparisons. Searches of recently released yeast sequences do not reveal any likely yeast homologs of DNA-dependent ATPase A, although a novel human homolog was identified by both southern blotting and sequence analysis, as detailed in Section 6.5, above.

The SNF2 family of proteins has been named after the yeast gene known as SNF2 or SWI2. The Snf2 protein appears to be a component of a large multi-subunit complex (Peterson et al., Proc. Natl. Acad. Sci. U.S.A. 91, 2905–2908 (1994); Kwon et al., Nature. 370, 477–481 (1994); Cote et al., Science. 265, 53–60 (1994); Cairns et al., Proc. Natl. Acad. Sci. U.S.A. 91, 1950–1954 (1994)) and may serve as a bridge (or molecular matchmaker; (Sancar and Hearst. Science. 259, 1415–1420 (1993))) between specific DNA-binding proteins and the transcriptional apparatus (Okabe et al., Nucleic Acids Res. 20, 4649–4655 (1992); Peterson and Herskowitz. Cell. 68, 573–583 (1992)). The similarity of ATPase domains (molecular motor) has been the main criteria for grouping proteins into the SNF2 family. It is clear that the peptide sequence outside the ATPase domain contributes to function and that not all of the members of this family have similar metabolic functions (Carlson and Laurent. Curr. Opin. Cell Biol. 6, 396–402 (1994)). Studies of SNF2 family members have led to proposed metabolic functions for proteins in this family including: DNA repair; transcriptional regulation (positive and negative); and chromatin remodeling. Putative links to DNA repair activities in the SNF2 family include transcription-coupled repair (ERCC6, RAD26), recombination repair (RAD54), nucleotide excision repair of silent genes (RAD16), post-replication repair (RAD5), and repair of UV and gamma irradiation (RAD8) (Eisen et al., Nucleic Acids Res. 23, 2715–2723 (1995)). Thus, targeting of the molecular motor domains with chemotherapeutic agents should lead to inhibition of a variety of DNA metabolic processes.

The complicated nature of the SNF2 family is not unprecedented. The DNA-dependent ATPase of the E. coli UvrABC complex has putative helicase domains but fails to show unwinding with all but the very shortest of substrates (Oh and Grossman. J. Biol. Chem. 264, 1336–1343 (1989)). The function of the UvrAB complex seems to be a melting into the DNA rather than exhibiting a true unwinding and thus yields partitioning of the DNA effector into supercoiled domains (Koo et al., Proc. Natl. Acad. Sci. U.S.A. 88, 1212–1216 (1991)). Similarly, the transcription-repair coupling factor (TRCF) from E. coli has helicase motifs with no apparent helicase activity (Drapkin et al., Cell. 77, 9–12 (1994)). Yet, TRCF plays a role in coupling transcription with DNA repair (two of the processes implicated for proteins in the SNF2 family) (Selby and Sancar. Science. 260, 53–58 (1993); Drapkin et al., Cell. 77, 9–12 (1994)).

7.1. Bacterial Expression of DNA-dependent ATPase A

In light of initial difficulties in expressing full-length recombinant DNA-dependent ATPase A protein having high activity, alternative expression constructs were made. Previous biochemical studies had identified sites of proteolytic cleavage of bovine DNA-dependent ATPase A yielding polypeptides with DNA binding and ATP hydrolytic activities. Thus, a plasmid construct was chosen that would express a peptide analogous to one of these proteolytic products containing the molecular motor domain. The bacterial expression vector pET24d(+) from Novagen (Madison, Wis.) was used for expressing the ADAAD polypeptide. The recommended kanamycin antibiotic resistance marker was used for selection. This novel DNA construct used NcoI and EcoRI restriction enzymes to construct a plasmid, designated pRM102, that carried the DNA-dependent ATPase A cDNA sequence starting at nucleotide 643 and ending at nucleotide 2826 (FIG. 1). After expression in E. coli BL21(DE3) (Novagen), the construct yielded a polypeptide which started with amino acid 215 of DNA-dependent ATPase A (see FIG. 3—underlining as in FIG. 2). The polypeptide has a calculated molecular mass of 81,525 and a calculated pI of 9.56. Expression of the polypeptide in this vector was quite good except that the protein was inactive. Unexpectedly, expression of the polypeptide in the absence of kanamycin yielded a fully functional polypeptide. The level of kanamycin used in the selective media was then determined to correlate directly with the loss of enzymatic activity of recombinantly expressed ATPase. Apparently, the inhibition of ATPase activity only occurs after the drug concentration exceeds a level high enough to yield modification of the drug (McKay et al., Biochemistry. 33, 6936–6944 (1994); McKay and Wright. J Biol Chem. 270, 24686–24692 (1995)), because the kanamycin itself is a poor inhibitor of the ATPase activity in vitro (see below).

E. coli BL21(DE3) containing the plasmid pRM102 was typically prepared as an overnight culture in LB medium (10 g tryptone, 5 g yeast extract, 10 g NaCl, adjust the pH to 7.0 by the addition of HCl, and bring the final volume to 1 L) plus kanamycin (30 µg/mL). The overnight culture may be subsequently diluted with an equal volume of sterile glycerol to yield a 50% glycerol stock which was stored at −80° C. For preparation of the 82 kDa polypeptide, an overnight culture was started from this stock of cells using LB medium (10 g tryptone, 5 g yeast extract, 10 g NaCl, adjust the pH to 7.0 by the addition of HCl, and bring the final volume to 1 L) without kanamycin. The bacterial resistance marker (aminophosphotransferase (3′)-IIIa) that has been used to construct and select the pRM102 clone results in phosphorylation of the kanamycin. The phosphokanamycin is an inhibitor of the 82 kDa polypeptide adenosine triphosphatase (ATPase) activity. Small amounts of kanamycin can be used in the overnight cultures if the dilution into subsequent cultures is sufficiently large to result in negligible concentrations of phosphokanamycin. It must be recognized that there is a minimal concentration of kanamycin that is required for bacterial selection and that concentration is sufficient to lead to significant inhibition of the 82 kDa polypeptide adenosinetriphosphatase activity. It is essential that any kanamycin be diluted such that phosphokanamycin concentrations will be negligible.

The cells grown overnight were diluted into fresh LB (10 g tryptone, 5 g yeast extract, 10 g NaCl, adjust the pH to 7.0 by the addition of HCl, and bring the final volume to 1 L) medium without kanamycin next day. Typical dilutions were 1:50 (1 mL of overnight grown culture was inoculated per 50 mL medium). Cells were grown at 25° C. to 1.0 O.D. measured at 600 nm. Isopropyl β-D-thioglactopyranoside (IPTG) was added to a final concentration of 0.5 mM. The cells were grown for two more hours and harvested in a low speed centrifuge (10,000×g—15 min) (5,000 rpm—Sorvall GS-3 rotor). The wet weight of the cells was measured. The cells were typically stored as a frozen pellet at −80° C.

7.2. Purification of the 82 kDa Polypeptide (ADAAD)

Frozen pellets of IPTG-induced E. coli BL21(DE3) containing the plasmid pRM102 were thawed at 4° C. and resuspended in 20 mL of 20 mM Tris-HCl pH 7.5, 5 mM EDTA, 5 mM EGTA, 5% (w/v) glycerol, 50 mM NaCl, 5 mM β-mercaptoethanol, and 0.5 mM phenyl methyl sulfonyl fluoride (PMSF) per gram of wet weight of cells. The cells were homogenized using five (5) passes in a Dounce homogenizer. Following homogenization, the cells were lysed using the French press. Two cycles of 1000–1500 psi pressure were used to lyse the cells.

The lysed cells were centrifuged at 12,000×g (10,000 rpm—Sorvall SS-34 rotor) for 30 minutes and the resulting pellet of cellular debris was discarded. Solid NaCl (2M) was added to the supernatant and the solution was centrifuged at 40,000 rpm for 2 hours in the ultracentrifuge (Beckman XL-90, 50.2 Ti, 145,000×g). Again, the debris in the pellet was discarded. The resulting supernatant was desalted by loading it onto a 900 mL BioRad P-60 (gel filtration) column (~17×8 cm). Generally a bed volume that was three (3) times the total volume of cell lysate was used. The column was loaded at a flow rate of 1440 mL/hr (gravity) with no fractions being collected initially. The absorbance of the eluate was monitored at 280 nm using a continuous flow cell in an ultraviolet monitor.

As the protein starts eluting from the column (based on the UV absorbance), the column was coupled to a BioRad Affigel-HZ guard column (2.5×2 cm), that was subsequently coupled to a monoclonal antibody 6E12-Affigel-HZ column (immunoaffinity column) (5×2 cm). The flow rate on these coupled columns was reduced to 20 mL/hr using a peristaltic pump and fractions of 30–50 drops/tube were collected. When the cellular supernatant was completely loaded, the P-60 column was washed further with 20 mM Tris-HCl pH 7.5, 5 mM EDTA, 5 mM EGTA, 20% (w/v) glycerol, and 50 mM NaCl. Fractions of 30–50 drops/tube were typically collected at this stage.

The P-60 column was uncoupled from the guard column at a stage when most of the protein has been eluted from the column but well before the salt and β-mercaptoethanol start to elute. (This step was believed to be critically important since the β-mercaptoethanol will be damaging to the immunoaffinity column.) After the P-60 column has been uncoupled, the guard column was washed with 20 mM Tris-HCl pH 7.5, 5 mM EDTA, 5 mM EGTA, 20% (w/v) glycerol, and 50 mM NaCl until the absorbance base-line was reached. Subsequently, the guard column and the 6E12 column were washed with 20 mM Tris-HCl pH 7.5, 5 mM EDTA, 5 mM EGTA, 20% (w/v) glycerol, and 550 mM NaCl. The columns were uncoupled at this stage.

The 82 kDa polypeptide adenosine triphosphatase protein was eluted from the 6E12 column using 20 mM Tris-HCl pH 7.5, 1 mM EDTA, 20% (w/v) glycerol, 2 M NaCl, and 1.4 M $MgCl_2$ at the rate of 20 mL/hr. When this wash was started, the column was typically disconnected from the fraction collector and fractions were collected manually (~10 minutes/fraction). The eluate continued to be monitored by UV absorbance.

The protein eluate was dialyzed against 1 L of 20 mM Tris-HCl pH 7.5, 5 mM EDTA, 5 mM EGTA, and 20% (w/v) glycerol containing phenyl methyl sulfonyl fluoride (PMSF) (0.5 mM). This step was limited to three hours with a change in the buffer after each hour. The protein may be concentrated prior to storage using Centricon concentrators. Subsequently, the protein was frozen using liquid nitrogen and stored at −80° C.

7.3. DNA-dependent ATPase A Assays 7.3.1. Colorimetric Assay

Enzyme (0.2 units (one unit is the amount of enzyme required to hydrolyze 1 µmole of adenosine triphosphate per min)) was mixed with 50 mM Tris-$SO_4$, pH 7.5, 1 mM $MgCl_2$, 5 mM β-mercaptoethanol, 0.5 mg/mL bovine serum albumin, 2 mM phosphoenol pyruvate, 0.03 mg/mL pyruvate kinase, 10 nM of stem-loop DNA, and 2 mM adenosine triphosphate in a total volume of 100 µL. The reaction was typically incubated at 37° C. for 10–60 minutes. At the end of the designated time, 225 µL of 10% sodium dodecyl sulfate and 350 µL of water were added to stop the reaction. Color development requires the addition of two reagents: 180 µL of reagent A (prepared by mixing equal volumes of 60 to 70% perchloric acid and 5% ammonium molybdate in water) and 45 µL of reagent B (0.2 g 1:2:4 aminonaphthol sulfonic acid, 12.0 g sodium metabisulfite, and 2.4 g sodium sulfite dissolved in 100 mL of water) was added. The reaction was incubated at room temperature for 10 minutes and the absorbance was read at 720 nm. The color development was time-dependent and therefore samples must be read at exactly 10 minutes.

7.3.2. NADH Oxidation Assay

Enzyme (0.2 units (one unit is the amount of enzyme required to hydrolyze 1 μmole of adenosine triphosphate per min)) was mixed with 25 mM Tris-acetate pH 7.5, 6 mM Mg(acetate)$_2$, 60 mM KCl, 5 mM β-mercaptoethanol, 3 mM phosphoenol pyruvate, 10 units/mL pyruvate kinase, 10 units/mL lactate dehydrogenase 10 nM DNA, 2 mM adenosine triphosphate, and 0.1 mg/mL NADH in a final volume of 1 mL. The progress of the reaction at 37° C. was monitored at 340 nm using an HP8452 spectrophotometer.

7.3.3. Radioactive Assay

Enzyme (0.2 U) was mixed with 50 mM Tris-SO$_4$, pH 7.5, 1 mM MgCl$_2$, 5 mM β-mercaptoethanol, 0.5 mg/mL bovine serum albumin, 2 mM phosphoenol pyruvate, 0.03 mg/mL pyruvate kinase, 10 nM of stem-loop DNA, and 2 mM adenosine triphosphate in a total volume of 50 μL. Three (3) μCi of [$^{32}$P]-γ-adenosine triphosphate was added to the reaction and typical incubation was for 60 minutes 37° C. EDTA (25 mM) was added to stop the reaction. 10 μL of the reaction was spotted on a poly(ethylenimine)-cellulose plate. The plate was developed using 0.9M LiCl and 7M urea as solvent system. The plate was allowed to dry and autoradiographed either using X-OMAT film or a phosphorimager.

7.4. DNA Effector Specificity for DNA-dependent ATPase A

A specific stem-loop structure was designed to resemble the double-stranded:single-stranded junctions such as those found in DNA replication forks, areas of DNA damage with disrupted base pairing, or transcription bubbles. Table 16, below, summarizes the results from tests of this structure along with a number of other oligonucleotides (17 different DNA constructs which fall within the descriptive classes in the table) for their ability to effect ATP hydrolysis.

FIG. 16
DNA Effector Specificity

| | Structure | Description | ΔG | Rel. Act. |
|---|---|---|---|---|
| 1 | 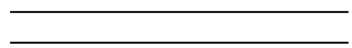 | Blunt-ended duplex | 23.7 | None |
| 2 | 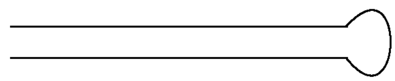 | Blunt-ended stem-loop (hairpin) | 18.4 | 90 |
| 3 | | Single-stranded, no hairpins, no self-complementarity | — | None |
| 4 | 5'—, —5' | Single-stranded, no hairpins, 5'-ends self complementary | 10.8 | None |
| 5 | —3', 3'— | Single-stranded, no hairpins, 3'-ends self-complementary | <5 / 7.3 / 7.3 / 10.8 / 12 | 10 / 15.5 / 16.6 / 40.8 / 69.0 |
| 6 | TATAA / ATATT | Blunt-ended duplex, AT-rich | 46.7 / — | 49.0 |
| 7 | XXXX | Blunt-ended duplex, 4 base mismatch | 41.9 | 66.5 |
| 8 | XXXXXXXXXXXX | Blunt-ended duplex, 10 base mismatch | 39.4 | 83.7 |

Since the thermodynamic stability of the secondary structure appears to be the parameter which is relevant to ATP hydrolytic activity, specific nucleotide sequences have not been listed. The stem-loop structure is a highly specific effector of ATP hydrolysis for ATPase A at concentrations 10,000-fold lower than those required for denatured, calf thymus DNA. While denatured, calf thymus DNA undoubtedly has secondary structure, it is anticipated that the largely single-stranded character of such DNA will result in competition for protein binding (albeit at lower affinity). Thus, heterogeneous DNAs may yield less than optimal levels of DNA-stimulated ATP hydrolysis (7-fold for HIP116, an SNF2 family member (Sheridan et al., *J. Biol. Chem.* 270, 4575–4587 (1995))) when compared with specific structures which can raise ATP hydrolysis more than 90-fold (Table 16).

A double-reciprocal analysis was employed to give characterize the binding affinity of ATPase A, through analysis of ADAAD, for the stem-loop structure. It was assumed that the DNA-protein interaction is in a rapid equilibrium and is not rate limiting. Under this condition and using a loop size of 12 bases, the association constant ($K_a$) is calculated to be ~1.3×10$^8$ M$^{-1}$ oligomer. Control oligonucleotides of the blunt-ended stem or the loop structure alone failed to effect ATP hydrolysis. Competition with the stem-loop structure using an equal concentration of single-stranded DNA failed to yield any inhibition of ATP hydrolysis. Finally, reduction of the loop size to 9, 6 and 3 bases leads to decreases in the apparent binding constant to 0.8×10$^8$, 0.5×10$^8$, and 0.2×10$^8$ M$^{-1}$, respectively. Thus, ATPase A has a high specificity for a unique structure but does not have a specific DNA primary base sequence which it recognizes.

The experiments summarized in Table 16 and the preceding paragraph demonstrate that DNA-dependent ATPase. A shows sequence-independent recognition of specific DNA structural elements, which are transitional regions of double-stranded to single-stranded DNA (these elements are found in DNA replication, DNA repair, transcription, etc.). The calculated association constant of $1.3 \times 10^8$ M$^{-1}$ is unusual for non-sequence specific DNA binding proteins but not unprecedented (TFIIIA binds to 5S RNA in a structure-specific fashion with a $K_a$ of $1 \times 10^9$ M$^{-1}$ (Romaniuk. *Nucleic Acids Res.* 13, 5369–5387 (1985))). That is, DNA-dependent ATPase A does not appear to recognize specific nucleotides and thus would not derive free energy of binding through bond formation with the edges of the planar bases. There is no reported precedence for such high binding energy being derived from protein interactions with the phosphate backbone of the DNA unless proteins bind cooperatively to that backbone. Cooperative behavior does occur in single-stranded binding proteins but DNA-dependent ATPase A does not use single-stranded DNA as an effector. One explanation is that the protein is conformationally or topologically linked to the phosphodiester backbone of the DNA in conjunction with either the binding or hydrolysis of ATP.

These results indicate that for a non-sequence-dependent binding protein, DNA-dependent ATPase A has an unusually high binding constant. DNA-dependent ATPase A hydrolyzes ATP only in the presence of DNA. This experimental result indicates that DNA-dependent ATPase A does not detectably modify the DNA; and, thus, DNA is an essential effector of the enzyme rather than a true substrate. DNA-dependent ATPase A shows specificity with respect to the DNA effector. The interaction between DNA-dependent ATPase A and DNA is not dependent upon the sequence of the DNA. The interaction appears to be solely dependent upon the structure of the DNA effector. Thus, the enzyme is maximally active only in the presence of a DNA molecule possessing a double-stranded to single-stranded transition region. DNA molecules lacking this structure do not affect ATP hydrolysis by DNA-dependent ATPase A. In addition, to the double-stranded to single-stranded transition region, our results also demonstrate that the presence of a hydroxyl group at the 3' position enhances the interaction between DNA-dependent ATPase A and DNA.

Our results further demonstrate that for optimal effectors, the double-stranded region of the DNA molecule should be longer that 11 base-pairs and the single-stranded region of the DNA molecule longer that 8 bases. DNA molecules containing double-stranded and single-stranded regions smaller than. the above specified criteria can function as an effector of DNA-dependent ATPase A, however, the interaction between the enzyme and the DNA does not lead to optimal ATP hydrolysis.

These data are consistent with the putative helicase motifs that occur in DNA-dependent ATPase A (and the SNF2 family in general) playing a role in "melting" into the DNA but without the strand displacement characteristic of helicases. Based on the above findings, the reports of SNF2 family members disassembling protein-DNA complexes in an ATP-dependent manner (Auble et al., *Genes Dev.* 8, 1920–1934 (1994); Kwon et al., *Nature.* 370, 477–481 (1994)) could be interpreted as a disruption of the DNA duplex structure by the ATPase with consequent disruption of other less stable protein-DNA complexes. Alternatively, certain protein-DNA interactions such as histone-DNA or TATA binding protein-DNA interactions could result in distortion of the DNA duplex thereby facilitating DNA-dependent ATPase recognition of a double-stranded:single-stranded structure with subsequent ATP hydrolysis leading to histone or TATA-binding protein displacement (Auble et al., *Genes Dev.* 8, 1920–1934 (1994); Kwon et al., *Nature.* 370, 477–481 (1994)). Histone displacement might then lead to facilitated binding of proteins which had been excluded from their DNA binding site by the histones (Imbalzano et al., *Nature.* 370, 481–485 (1994)).

Regardless of the mechanism, these results demonstrate that the DNA binding domain of a nucleic acid-dependent ATPase (i.e., the molecular motor) is an excellent target for disrupting important DNA structural features and hence a variety of metabolic functions.

8. EXAMPLE

Identification of Inhibitors of DNA-Dependent ATPases

The phenomenon described in Section 7.1, above, in which recombinant DNA-dependent ATPase A was inactive when produced in cells exposed to kanamycin was analyzed further. Initial efforts to overexpress the DNA-dependent ATPase A protein in bacteria lead to the surprising observation that in the presence of the aminoglycoside antibiotic, kanamycin, the kanamycin-resistant bacteria overproduce the polypeptide but it is apparently inactive. In order to achieve resistance to kanamycin, the bacteria express an enzyme which phosphorylates the 3'-position of one of the sugar residues. As detailed below, the 3'-phosphokanamycin mimics the 3'-phosphorylated DNA which has been shown to be an inhibitor of ATP hydrolysis for this enzyme and the data reveal that 3'-phosphokanamycin is a potent competitive (with respect to DNA) inhibitor of DNA-dependent ATPase A.

In bacteria without resistance markers (plasmids carrying genes for aminoglycoside-modifying enzymes) it is well documented that aminoglycoside antibiotics (e.g. kanamycin) lead to breakdown of the peptide-chain initiation complex for protein synthesis and/or blockage of ribosomal dissociation. No synthesis of polypeptide chains clearly leads to bacterial cell death and hence the efficacious use of these antibiotics. With the advent of molecular biological techniques, a variety of aminoglycoside modifying enzymes can be introduced into bacteria via plasmids (Shaw et al., *Microbiol Rev.* 57, 138–163 (1993)). The pET vectors (Studier et al., *Methods Enzymol.* 185, 60–89 (1990)) used in construction of the novel DNA-dependent ATPase A overproducing strain contain a gene encoding an aminoglycoside phosphotransferase (APH) gene which mediates bacterial resistance by phosphorylating kanamycin in the 3'-hydroxyl position of a sugar substituent, yielding a modified antibiotic which no longer disrupts protein synthesis. Thus, if expression of the cloned gene occurs, there is no a priori reason to expect inhibition of enzymatic function of the overexpressed polypeptide. Indeed, consultations with Novagen and literature searches have not documented any reports similar to the observations disclosed herein.

Thus, the chemistry of the phosphorylated kanamycin was analyzed. This analysis, detailed below, yielded the following observations: kanamycin is a deoxy sugar antibiotic; kanamycin is composed of multiple sugar residues; and kanamycin is phosphorylated at the 3' position of one sugar ring by APH.

This information was then correlated with novel results, obtained as detailed below, regarding the enzymatic activity of DNA-dependent ATPase A which: only uses deoxyribonucleic acids as effectors of ATP hydrolysis (Hockensmith et al., Biochemistry. 25, 7812–7821 (1986)); is inhibited by 3'-phosphorylated DNA (Hockensmith et al., Biochemistry. 25, 7812–7821 (1986)); and apparently recognizes structural elements in DNA based on binding to the sugar residues of the DNA.

As detailed below, phosphoaminoglycosides are a class of potent inhibitors of DNA-dependent ATPase A.

8.1. Synthesis of Phosphorylated Aminoglycosides

Aminoglycoside phosphotransferase (APH) catalyzes the transfer of the γ-phosphate from ATP to the 3'-position of aminoglycosides (FIG. 4) yielding a 3'-phosphoaminoglycoside. An overexpression system for aminoglycoside phosphotransferase (APH) (McKay et al., Biochemistry. 33, 6936–6944 (1994); McKay and Wright. J Biol Chem. 270, 24686–24692 (1995)) was used to produce recombinant APH. The APH enzyme has been partially purified using an anion exchange resin (DEAE-cellulose) which was washed with 50 mM Tris-HCl pH 8.0, 1 mM EDTA and eluted with a gradient from 0 to 750 mM NaCl in the same buffer.

The partially purified APH enzyme was subsequently used to prepare 3'-phosphokanamycin, 3'-phosphoneomycin and 3'-phosphogeneticin according to the McKay et al. protocol (McKay et al., Biochemistry. 33, 6936–6944 (1994)). The phosphoaminoglycosides are purified using Bio-Rex 70 column chromatography with a mobile phase of 1.5% ammonium hydroxide, which resolves the ATP, parent aminoglycoside and phosphoaminoglycoside when eluted with 1.5% ammonium hydroxide. The phosphoaminoglycoside is recovered by lyophilization of the solvent phase. Identification of the phosphoaminoglycoside is based on TLC and ninhydrin visualization. Yields following purification generally amount to 1–2% (1–2 mg) of the starting material (100 mg).

A novel alternative purification protocol uses an iron:chelate column. A support matrix is derivatized with iminodiacetic acid and iron (ferric chloride) is chelated to the matrix. Chromatography of the phosphokanamycin synthesis mixture using water as the mobile phase results in phosphokanamycin flowing through the matrix with the kanamycin being retain by the matrix. The yield of phosphokanamycin using this procedure is approximately 3.3% of the starting material and it is typically contaminated with iron and ATP.

8.1.1 Preparation of Aminoglycoside Phosphotransferase (3')-IIIa (APH(3')-IIIa)

8.1.1.1. Bacterial Growth

*E. coil* BL21(DE3) containing the plasmid pETSacG1 was typically prepared as an overnight culture in LB medium (10 g tryptone, 5 g yeast extract, 10 g NaCl, adjust the pH to 7.0 by the addition of HCl, and bring the final volume to 1 L) plus ampicillin (100 µg/mL). The overnight culture may be subsequently diluted with an equal volume of sterile glycerol to yield a 50% glycerol stock which was stored at −80° C. For preparation of the APH(3')-IIIa protein, a 200 mL overnight culture was typically diluted into 4 L of LB media containing 100 µg/mL of ampicillin. Cells were grown at 37° C. to 0.5 O.D. measured at 600 nm. This typically takes several hours. Isopropyl β-D-thioglactopyranoside (IPTG) was added to a final concentration of 0.5 mM. The cells were grown for four more hours and harvested in a low speed centrifuge (10,000×g—15 min) (5,000 rpm—Sorvall GS-3 rotor). The harvested cells were divided into 4 aliquots and stored at −80° C.

8.1.1.2. Purification of the APH(3')-IIIa Protein

The aminoglycoside phosphotransferase (3')-IIIa was prepared from *E. coli* BL21(DE3) containing the plasmid pETSacG1. An aliquot of cells (see above) was thawed at 4° C. and resuspended in 10 mL of 50 mM Tris-HCl pH 8.0, 200 mM NaCl, 1 mM EDTA, 0.1 mM phenyl methyl sulfonyl fluoride (PMSF), 0.1 mM dithiothreitol. The cells were homogenized using five (5) passes in a Dounce homogenizer. Following homogenization, the cells were lysed using the French press. Two cycles of 1000–1500 psi pressure were used to lyse the cells. The lysed cells were centrifuged at 12,000×g (10,000 rpm—Sorvall SS-34 rotor) for 30 minutes and the resulting pellet of cellular debris was discarded.

The resulting supernatant was diluted in 40 mL of 50 mM Tris-HCl pH 8.0 and 1 mM EDTA. The diluted supernatant was loaded onto a 40 mL DEAE-cellulose column (13×2 cm) equilibrated in 50 mM Tris-HCl pH 8.0 and 1 mM EDTA. The column was then washed at 20 mL/hr (peristaltic pump) with 50 mM Tris-HCl pH 8.0 and 1 mM EDTA until the $A_{280}$ reaches baseline. Fractions of 50–75 drops were collected and a gradient of NaCl from 0 mM to 750 mM in 50 mM Tris-HCl pH 8.0 and 1 mM EDTA started. The fractions were assayed for activity. Fractions showing kanamycin dependent adenosine triphosphate hydrolysis were pooled together.

8.1.1.3. APH(3')-IIIa Activity Assay

Column fractions (10 µL) were mixed with 50 mM Tris-HCl pH 7.5, 40 mM KCl, 10 mM $MgCl_2$, 2.5 mM phosphoenol pyruvate, 10 units/mL pyruvate kinase, and 10 units/mL lactate dehydrogenase. NADH was added to a final concentration of 0.5 mg/mL and adenosine triphosphate was added to a final concentration of 1 mM. Kanamycin was added to yield a final concentration 0.1 mM. The progress of the reaction at 37° C. was monitored at 340 nm using an HP8452 spectrophotometer.

8.1.2. Synthesis of Phosphorylated Aminoglycosides 8.1.2.1. 3'-phosphokanamycin

Synthesis of 3'-phosphokanamycin was performed in a 250 mL reaction volume of 50 mM HEPES pH 7.5, 10 mM MgCl2, 3 mM adenosine triphosphate, and 0.68 mM kanamycin. The synthesis reaction was incubated in a watershaker bath at 37° C. and was initiated using 2 mL of the APH(3')-IIIa pooled fractions. After incubation for 24 hours, an additional 2 mL of the APH(3')-IIIa pooled fractions and an additional 3 mM ATP were added to the reactions mixture. A final addition of APH(3')-IIIa (2 mL) was made at 36 hours. Finally, the reaction was removed from the water bath and stored at 4° C. at the end of 48 hours.

8.1.2.2. 3'-phosphoneomycin

Synthesis of 3'-phosphoneomycin was performed in a 400 mL reaction volume of 50 mM HEPES pH 7.5, 10 mM $MgCl_2$, 3 mM adenosine triphosphate, and 0.265 mM neomycin. The synthesis reaction was incubated in a watershaker bath at 37° C. and was initiated using 2 mL of the APH(3')-IIIa pooled fractions. After incubation for 24 hours, an additional 2 mL of the APH(3')-IIIa pooled fractions and an additional 3 mM ATP were added to the reactions mixture. A final addition of APH(3')-IIIa (2 mL) was made at 36 hours. Finally, the reaction was removed from the water bath and stored at 4° C. at the end of 48 hours.

8.1.2.3. 3'-phosphogeneticin

Synthesis of 3'-phosphogeneticin was performed in a 400 mL reaction volume of 50 mM HEPES pH 7.5, 10 mM MgCl2, 3 mM adenosine triphosphate, and 0.265 mM neomycin. The synthesis reaction was incubated in a watershaker bath at 37° C. and was initiated using 2 mL of the APH(3')-IIIa pooled fractions. After incubation for 24 hours, an additional 2 mL of the APH(3')-IIIa pooled fractions and an additional 3 mM ATP were added to the reactions mixture. A final addition of APH(3')-IIIa (2 mL) was made at 36 hours. Finally, the reaction was removed from the water bath and stored at 4° C. at the end of 48 hours.

8.1.3. Purification of Phosphorylated Aminoglycosides 8.1.3.1. Bio-Rex 70 Column Protocol Approximately 30 g Bio-Rex 70 (BioRad) column material was mixed with the reaction solution resulting from synthesis of the phosphoaminoglycosides. A rotating mixing device was used to mix the column material with the reaction solution for two hours. The entire mix was then poured into a column (12×3 cm) and washed with deionized water at a flow rate of 50 mL/hr. The wash was extensive and generally occurred over a 12 hour period. The wash was typically collected in a single beaker.

Following the extensive water wash, the column was eluted with 1.5% ammonium hydroxide. Fractions were collected for the first 200 mL wash (150 drops/fraction). These fraction contain the unreacted aminoglycoside. The column was disconnected from the fraction collector and washed with the 1.5% ammonium hydroxide for a further 10 hours. About 500 mL of eluate was collected in a single fraction.

The initial fractions collected from the 1.5% ammonium hydroxide was were analyzed by thin layer chromatography (TLC). The TLC analysis was essential for identification of the fractions that contain the unreacted aminoglycoside. Fractions that were free of the parent aminoglycoside were then pooled with the late eluate and the combined fractions was dried using a Rotavapour-R at 37° C. The dried material was resuspended in deionized, distilled water and the pH was adjusted to pH 7.0 using 11.6 M HCl. The resulting derivative was quantitated using TLC analysis.

8.1.3.2. Thin Layer Chromatography (TLC) Analysis

Phosphoaminoglycosides were analyzed for purity and quantitated by thin layer chromatography on silica gel plates. Sample volumes of up to 40 µL were spotted and dried onto silica gel plates. The plate was then developed using a solution of 5:2 methanol:ammonium hydroxide (14.8 M). The parent aminoglycoside and/or phosphoaminoglycoside were visualized using a spray of 0.5% Ninhydrin in n-butanol. Under these conditions, the phosphoderivatives migrate faster than the parent aminoglycosides.

For quantitation of the phosphoderivatives, a standard dilution series using the parent aminoglycosides was run concurrently with the phospho-derivative. Comparison of the intensity of the color developed gives an approximation of the concentration of the drug.

8.2 Characterization of Phosphoaminoglycoside Inhibitory Effects

FIG. 5A shows the effects of kanamycin and phosphokanamycin on ATP hydrolysis by overexpressed DNA-dependent ATPase A. The addition of the 3'-phosphoryl group to the kanamycin results in a striking 1000-fold decrease in the amount of drug required to effect a given level of inhibition. Similar results have now been obtained for a number of compounds including neomycin, phosphoneomycin, geneticin and phosphogeneticin (FIGS. 5B and 5C). A more complete listing of aminoglycosides that were phosphorylated by this method in accordance with the invention is shown in Table 4, along with structures of the parent compounds, in Section 5.4.1, above.

Kinetic analysis of ATP hydrolysis, suggests that the phosphoaminoglycoside derivatives are competitive inhibitors with respect to DNA concentration (FIGS. 6A–B). The $K_i$ for phosphokanamycin is approximately 200 nM, while phosphoneomycin is considerably more potent with a $K_i$ of 10 nM.

The specificity of an inhibitor is of critical importance when considering the effect of any new drug on cellular systems. That is, drugs which bind to ATP binding pockets of enzymes are generally cytotoxic as a result of the large number of different enzymatic systems that they affect.

A number of different ATPases, both DNA-dependent and DNA-independent, were analyzed for their behavior with respect to these drugs. The results demonstrate that DNA-independent ATPases are neither affected by neomycin nor by phosphoneomycin (FIGS. 6A–B).

Furthermore, at millimolar concentrations of neomycin, all DNA-dependent ATPases show some inhibition. This inhibition is directly attributable to the positive charge that the aminoglycosides carry and thus the sequestering of the DNA (negatively charged) away from the enzyme (the binding of kanamycin directly to DNA has been confirmed—data not shown). In addition, the phosphoneomycin has differing effects on DNA-dependent ATPases from various sources and of various function. Phosphoneomycin yields a more specific inhibition of DNA-dependent ATPase A compared to either gp44/62 or helicase II. Phosphoneomycin does act as a competitive inhibitor of gp44/62 with respect to DNA but the $K_i$ is approximately 500 nM or 50-fold higher than for DNA-dependent ATPase A.

The results depicted in FIGS. 6A–B are an important milestone in understanding the inhibitory action of the phosphoaminoglycosides. For example, the phosphoaminoglycosides do not inhibit non-DNA binding ATPases, which is consistent with the fact that the phosphoaminoglycosides compete with DNA to cause inhibition of DNA-dependent ATPase A. Consequently, these drugs are excellent candidates for targeting DNA metabolic processes which rely on DNA-dependent ATPases.

The level of inhibition caused by the phosphoaminoglycoside is highest for the eukaryotic DNA-dependent ATPase A but lower sensitivity to the drug is noted for the gp44/62 and helicase II proteins. These two proteins are both known to work at junctures in a DNA molecule that exhibit a double-stranded to single-stranded transition. Further results demonstrate that eukaryotic topoisomerase II, which is a DNA-dependent ATPase using double-stranded DNA effectors, is not inhibited by phosphoaminoglycosides.

9. EXAMPLE

Isolation of Full-Length DNA-Dependent ATPase A

The following protocol can be used to express the full-length DNA-dependent ATPase A protein. Although this method is described with respect to the full-length protein, it can be applied to any desired sub-fragment of the full-length protein by selection of appropriate primers and restriction enzymes based on the nucleotide sequence disclosed in FIG. 1, for example.

The gene encoding the 105-kDa polypeptide is amplified, from pPAT411 clone, using primers specific for the 3' and the 5' end of the gene. The 3' end primer possesses the restriction site for Not I and the 5' end primer contains the EcoRI restriction site.

The PCR product is digested with EcoRI and Not I enzymes.

The vector, pPICZ (Invitrogen, Carlsbad, Calif.), is linearized by digesting with EcoRI and NotI enzymes.

The PCR product is ligated into the linearized vector.

The ligated products are restricted with KpnI enzyme. This step cleaves the vector:vector ligated products.

The vector:PCR ligated products are transformed into JM109 cells. The transformants are selected using Zeocin.

The transformants are screened for the presence of the DNA-dependent ATPase A gene. The selected transformants are linearized.

The linearized construct is transformed into *Pichia pastoris* using electroporation. The transformants are selected using Zeocin.

The transformants are screened for the expression of DNA-dependent ATPase A. The selected transformant is used for the overexpression and purification of the 105-kDa DNA-dependent ATPase A.

10. EXAMPLE

Inhibition of Cellular DNA Synthesis

The effect of phosphoaminoglycoside inhibitors on cell growth was analyzed. The most probable mode of resistance of prokaryotic cells to these drugs is likely to be a transport problem where the phosphoaminoglycosides never pass beyond the periplasmic space and thus never reach the location of the DNA metabolic machinery. Recently there have been reports of prokaryotic proteins with a high homology to the SNF2 family (Kolsto et al., *J. Mol. Biol.* 230, 684–688 (1993)). Thus, prokaryotes should be can be made sensitive to these drugs if sufficient quantities could reach the proper compartment of the cell. This may be effected by using combination therapy where one drug (e.g. penicillin derivative) facilitates entry of the second drug (phosphoaminoglycoside) into the cell.

The ability of phosphoaminoglycoside-induced inhibition of DNA-dependent ATPase A activity in eukaryotic cells to disrupt DNA synthesis was tested. The issue of aminoglycoside transport into cells was avoided by using a permeabilized cell system that is competent for DNA synthesis.

CHO non-K1 cells were used for the DNA replication assay. Cells were grown to density of $2 \times 10^7$ cells/plate in MEM medium supplemented with fetal calf serum. The cells were in log phase and unsynchronized. The plates were washed three times with cold MEM medium and cells were scraped off the plates into eppendorf tubes. The cells were centrifuged at 2000 rpm for 3 mm at 4° C. From each plate approximately 100 $\mu$l of cells were obtained. The cell pellet was resuspended in an equal volume of replication buffer [100 mM HEPES (pH 7.8), 0.2 mM dGTP, 0.2 mM DATP, 0.2 mM dTTP, 0.4 mM GTP, 0.4 mM CTP, 0.4 mM UTP, 8 mM ATP, 20 mM $MgCl_2$, 0.2 mg/ml BSA, 2 mM DTT, 30% glycerol]. The cell suspension (20 $\mu$l) was aliquoted to individual tubes. Aminoglycosides and phosphoaminoglycosides were then added to the required final concentration. The cells were permeabilized by the addition of 0.5 $\mu$l of 20% NP-40 detergent. To monitor replication, 2 $\mu$l of $\alpha[^{32}P]$ dCTP (3000–6000 Ci/mmole activity) was added. The cells were incubated at 37° C. for 10 min and the reaction was stopped by addition of 200 $\mu$l of stop buffer [50 mM TrisCl (pH 8.0), 10 mM EDTA, 400 mM NaCl, 1% SDS]. The cells were further incubated at 37° C. for 2 hours.

The DNA was sheared by passing 5–10 times through a 23 gauge needle. 20 $\mu$l of this sample was precipitated with acid [1N HCl, 1% sodium pyrophosphate] onto a GF-C filter (Whatman). The filter was washed 3 times with acid and then with ethanol. After drying, the radioactivity was measured using a liquid scintillation counter (Beckman).

The results are shown in FIG. 7. The results clearly show that the addition of phosphokanamycin and phosphoneomycin disrupted DNA synthesis.

11. EXAMPLE

Inhibition of Prostate Tumor Cell Growth

The effect of phosphoaminoglycosides on tumor cell growth was tested in cell culture inhibition studies. 5000 cells were plated in a total volume of 50 $\mu$l in a 96 well titer plate. After 24 hours, 50 $\mu$l of media and drugs, to the required final concentration, were added. The plates were incubated at 37° C. for 5 days. On the $5^{th}$ day, the fraction of surviving cells was estimated using a non-radioactive cell proliferation assay (CellTiter 96 $AQ_{ueous}$ Cell Proliferation Assay from Promega).

This is a colorimetric assay that determines the number of viable cells. The assay measures the bioreduction of a tetrazolium compound (3-(4,5-dimethylthiazol-2-yl)-5-(3-carboxymethoxyphenyl)-2-(4-sulfophenyl)-2H-tetrazolium, inner salt; MTS), via an electron coupling reagent (phenazine methosulfate; PMS), to formazan, which is soluble in the tissue culture medium. The absorbance of formazan at 490 nm can be measured from the 96 well assay plate without additional processing. The conversion of MTS into the aqueous soluble formazan is accomplished by dehydrogenase enzymes found in metabolically active cells. The quantity of formazan product as measured by the amount of 490 nm absorbance is directly proportional to the number of living cells in culture. 100 $\mu$l of the PMS reagent (Promega) was mixed with 2.0 ml of MTS solution (Promega). 20 $\mu$l of PMS/MTS solution was added to the cells and the plates were incubated at 37° C. for 2 hours before measuring the absorbance at 490 nm.

In an initial experiment, four drugs (A-kanamycin, B-phosphokanamycin, C-neomycin, and D-phosphoneomycin) were added to prostate cancer cell cultures in a blind fashion. Two prostate cancer cell lines were incubated with each of the drugs and assayed for cell survivability using the MTS assay (Promega). An LNCaP cell line did not demonstrate any sensitivity to the drugs at the concentrations used (phosphokanamycin–100 $\mu$M–8 wells yielding 109±9% cell survival or phosphoneomycin–10 $\mu$M–8 wells yielding 119±6% cell survival), while a PC3 cell line exhibited a 24% reduction in cell survival with either of the phosphorylated derivatives.

Further experimental results obtained by this method are shown in FIG. 8 for the PC3 cell line.

5000 cells were grown overnight in media and each respective drug (A-kanamycin, B-phosphokanamycin, C-neomycin, and D-phosphoneomycin) was added on the second day. On day five, the cells were incubated with MTS (Promega, Madison, Wis.) to determine the number of surviving cells. Each point is the average of readings from three wells.

The results shown in FIG. 8 demonstrate that both phosphkanamycin and phosphoneomycin were effective in killing the PC3 cells; whereas neither kanamycin nor neomycin had any effect on the cells. Concentrations of the parent aminoglycosides (kanamycin and nemomycin) in excess of 1 mM showed increased cell survival and are not shown.

12. EXAMPLE

Inhibition of Breast Cancer Cell Growth

Neomycin and phosphoneomycin were also been tested in cell cultures of two breast cancer cell lines (MCF-7 and MDA-MB-231) using the methods described in Section 11 for PC3 cells, above.

The results are shown in FIG. 9 and are very similar to those obtained with the PC3 cells. Specifically, phosphoneomycin inhibits growth of these-cell lines, whereas neomycin has no effect on either cell line.

13. EXAMPLE

Treatment of Tumors

Further experimentation demonstrates that the phosphorylated aminoglycosides can cause regression of tumors formed from implantation of human tumor cells in nude, athymic mice.

Human PC3 (prostate cancer) cells were implanted subcutaneously in nude, athymic mice. Following tumor development to a size of approximately 200 cubic millimeters, tumors were injected directly with 50 μl of 1.3 mM phosphokanamycin every Monday, Wednesday, and Friday for two weeks.

CRL: CD-lnu/nu Br mice (nude, athymic) were obtained from Charles River Animal Resources Facility. Human PC3 cells were grown in RPMI 1640 media containing 10% serum, 200 μl of this cell culture was diluted 1:1 with Matrigel (Collaborative Biomedical Products) such that the total number of cells after dilution were $2 \times 10^6$. The cells were then injected on the underside of the flank and the development of subcutaneous tumor size was monitored by measurement with Vernier calipers.

Therapy with the drugs was started when the tumor size reached 200 mm$^3$. The drugs were solubilized in PBS (0.35 g NaH$_2$PO$_4$, 1.06 g Na$_2$HPO and 8.5 g in a total volume of 1 L, pH 7.2), pH was adjusted to 7.2 using phosphoric acid and filter sterilized before injection. 50 μl of the drug (1.3 mM phosphokanamycin) was administered by direct injection into the tumor every Monday, Wednesday, and Friday for two weeks. The tumor size was monitored by measurement with Vernier calipers. The mice were euthanized when the tumor size exceeded 1000 mm$^3$ or when the weight of the mice decreased by more than 15% of their starting weight. The tumor size was calculated using the following formula:

$$volume = [length \times (width)^2]/2$$

The results are shown in FIG. 10. Average tumor size was plotted against the days following implantation.

This experiment yields four significant results: 1) Tumors regress in size and ultimately disappear, with the process of regression continuing even after treatment has been terminated; 2) although metastasis has occurred prior to start of the treatment, no remote lesions are detected following treatment with the phosphoaminoglycosides; 3) no detectable toxicity occurred with treatments that lasted as long as 8 weeks; and 4) treated mice demonstrate significant longevity relative to the untreated controls (equivalent to more than seven years of human life).

14. EXAMPLE

Inhibition of Amebic Growth

Phosphokanamycin and phosphoneomycin were used in amoebic cultures. *Entamoeba histolytica* cultures were treated with varying concentrations of either kanamycin or phosphokanamycin.

*Entamoeba histolytica* HM1-ISS strain was used for the experiment. The cells were grown in tissue culture medium TYI-S-33 containing trypticase, yeast extract, iron and serum along with 100 units/ml penicillin and 100 μl/ml streptomycin sulfate. 500,000 amoebae were incubated in 2 mls of media. The drugs were added to the required final concentration. The total number of amoebae was counted every 24 hours after the addition of drugs using light microscope. Growth was monitored over a period of 72 hours. The results are shown in FIG. 11.

The results clearly demonstrate that phosphokanamycin completely kills the cells at a concentration of 200 μM, whereas kanamycin had no effect on the cells.

These observations led to the hypothesis that the aminoglycosides are not transported efficiently into cells but that the aminoglycosides are positively charged and merely "decorate" the negatively charged phospholipid membrane of the cell. The aminoglycosides could then be taken into the cell by any mechanism that turned over the cell membrane (e.g. endocytosis, pinocytosis, etc.). In this scenario, the aminoglycoside merely becomes the carrier of the toxic 3'-phosphorylated sugar residue. Amebas undergo large amounts of membrane turnover because they use a process of endocytosis. Therefore, the susceptibility of other protozoa to these phosphoaminoglycoside inhibitors was tested, as detailed in the Example in Section 15, below.

15. EXAMPLE

Inhibition of Leishmania Growth

Experiments using phosphokanamycin and phosphoneomycin were performed with Leishmania.

*Leishmania chagasi* cells were grown in HO-MEM medium to a cell density of $1 \times 10^6$ cells/ml. 50 μl of drug were mixed with 50 μl of media in the first well of a 96 well micro titer plate. Serial, two-fold dilutions were then made by taking 50 μl of the solution in the first well and diluting it into the second well and this process was repeated through the 12 wells of an entire row of the 96 well plate. This gives a 2-fold difference in the concentration of the drug between the wells in that row. This procedure was repeated for all the inhibitors. 50 μl of *Leishmania chagasi*, at a cell density of $1 \times 10^6$ cells/ml, was then added to the wells. The micro titer plate was incubated at 30° C. under anaerobic conditions. Cells were counted under light microscope every 24 hours after addition of drugs.

The results are shown in FIGS. 12A–B. Both phosphokanamycin and phosphoneomycin were clearly effective in killing the cells, whereas both kanamycin and neomycin were not. In addition, Leishmania are much more sensitive to phosphoneomycin than either prostate or breast cancer cell lines. Furthermore, unlike the amoeba, phosphoneomycin has an even more profound effect than the phosphokanamycin on Leishmania. These differences in sensitivity and specificity can be used in designing specific treatment regimens using these compounds.

16. EXAMPLE

Inhibition of DNA Repair Through Inhibition of DNA-Dependent ATPase A

The following experiment demonstrates the disruption of DNA repair through inhibition of DNA-dependent ATPase A. *Xenopus laevis* oocytes have been used by Ackerman and his colleagues as a model system to study nucleotide excision repair (NER) of UV-damaged plasmid DNA (Saxena et al., *Nucleic Acids Res.* 18, 7425–7432 (1990)). The Ackerman system was used to examine the effect of MAbs specific for DNA-dependent ATPase A on DNA repair by co-injecting Xenopus oocytes with MAbs and plasmids containing random pyrimidine dimers. The MAbs are described in Section 7, above.

In the absence of MAb, ~$10^{10}$ dimers can be repaired per oocyte (Saxena et al., *Nucleic Acids Res.* 18, 7425–7432 (1990)). A number of the anti-ATPase A MAbs recognize antigens from Xenopus and upon microinjection into the nuclei of oocytes result in the inhibition of DNA repair. The mechanism of inhibition of DNA repair is not simply an inhibition of ATP hydrolysis since none of the MAbs demonstrate inhibition of DNA-dependent ATP hydrolysis in vitro, which suggests that the MAbs occlude neither the DNA binding nor the ATP binding site of the ATPase. Thus, disruption of or steric exclusion in a multiple protein complex can account for the observed antibody induced inhibition of DNA repair. In addition to the inhibition of DNA repair, at least six of the MAbs also result in the inhibition of DNA synthesis that is responsible for conversion of single-stranded to double-stranded DNA.

The importance of these observations lies in the idea that the ATPase as a molecular motor will play a vital role in a variety of DNA metabolic processes that use different proteins "driven" by a common motor. A simple analogy would be a toy engine which runs an airplane, a car and a boat. All three vehicles perform different functions driven by the same energy consuming process. In the case of eukaryotic DNA-dependent ATPases, targeting of the molecular motor effectively shuts down the DNA metabolic processes.

17. DEPOSIT OF PLASMID-CONTAINING MICROORGANISMS

On Apr. 14, 1998, the following plasmids were deposited with the American Type Culture Collection, 10801 University Boulevard, Manassas, Va. 20110–2209:

| Plasmid | Host | Accession No. |
|---|---|---|
| pPAT411 | E. coli BL21 (DE3) | 98732 |
| pRM102 | E. coli BL21 (DE3) | 98731 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An assay for identifying a compound that inhibits nucleic acid metabolism, comprising:
   (a) contacting a test compound with a human DNA-dependent ATPase A comprising SEQ ID NO:66 that is encoded by a nucleotide sequence that hybridizes to SEQ ID NO: 54 under highly stringent conditions comprising washing in 0.1×SSC/0.1% SDS at 68° C., and an effector of ATP hydrolysis, wherein said effector is a polynucleotide or oligonucleotide that forms a structure having a double stranded/single stranded junction;
   (b) measuring the level of DNA-dependent ATPase A activity; and
   (c) comparing the level of obtained in (b) to the DNA-dependent ATPase A activity obtained in the absence of the test compound; such that if the level obtained in (b) is lower than that obtained in the absence of test compound, a compound that inhibits nucleic acid metabolism has been identified.

2. The method of claim 1 wherein the compound inhibits DNA replication.

3. The method of claim 1 wherein the compound inhibits transcription.

4. The method of claim 1 wherein the compound inhibits recombination.

5. The method of claim 1 wherein the compound inhibits chromatin remodeling.

6. The method of claim 1 wherein the compound inhibits DNA repair.

7. The method of claim 1 wherein the structure has as stem and a loop.

8. The method of claim 7 wherein the stem has at least 11 base pairs.

9. The method of claim 7 wherein the loop has at least 8 nucleotides.

10. The method of claim 1 wherein the test compound is a phosphorylated aminoglycoside.

11. The method of claim 10 wherein the aminoglycoside that is phosphorylated is amikacin, butirosin, geneticin, gentamicin, kanamycin, lividomycin, neomycin, or paromomycin.

12. A method of identifying a compound that inhibits nucleic acid metabolism, comprising:
   (a) contacting a DNA-dependent ATPase A, selected from the group consisting of SEQ ID NO: 55 and a human DNA-dependent ATPase A comprising SEQ ID NO: 66, with a phosphorylated aminoglycoside;
   (b) measuring the level of the activity of the DNA-dependent ATPase A; and
   (c) comparing the level obtained in (b) to the DNA-dependent ATPase A activity obtained in absence of the phosphorylated aminoglycoside, such that if the level obtained in (b) is lower than that obtained in the absence of the phosphorylated aminoglycoside, a compound that inhibits nucleic acid metabolism has been identified.

* * * * *

UNITED STATES PATENT AND TRADEMARK OFFICE
CERTIFICATE OF CORRECTION

PATENT NO. : 6,573,060 B1  
APPLICATION NO. : 09/722708  
DATED : June 3, 2003  
INVENTOR(S) : Hockensmith et al.

Page 1 of 1

It is certified that error appears in the above-identified patent and that said Letters Patent is hereby corrected as shown below:

In The Specification  
In column 1, line 12-13, delete "partially made with government support under grant number R29GM43569" and insert --made with government support under GM043569--, therefor Signed and Sealed this  
Twenty-eighth Day of June, 2016

Michelle K. Lee  
*Director of the United States Patent and Trademark Office*